(12) United States Patent
Wilson et al.

(10) Patent No.: US 6,875,229 B2
(45) Date of Patent: Apr. 5, 2005

(54) STENT AND CATHETER ASSEMBLY AND METHOD FOR TREATING BIFURCATIONS

(75) Inventors: W. Stan Wilson, Missoula, MT (US); Kevin M. Mauch, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 249 days.

(21) Appl. No.: 10/353,116

(22) Filed: Jan. 27, 2003

(65) Prior Publication Data

US 2004/0054404 A1 Mar. 18, 2004

Related U.S. Application Data

(63) Continuation of application No. 09/882,989, filed on Jun. 14, 2001, now Pat. No. 6,579,312, which is a continuation of application No. 09/412,113, filed on Oct. 5, 1999, now Pat. No. 6,264,682, which is a continuation of application No. 08/910,857, filed on Aug. 13, 1997, now Pat. No. 6,165,195.

(51) Int. Cl.$^7$ .................................................. A61F 2/06
(52) U.S. Cl. ....................................................... 623/1.35
(58) Field of Search ............................... 623/1.35, 1.36, 623/1.11; 606/191, 192, 194, 195, 198

(56) References Cited

U.S. PATENT DOCUMENTS

| 2,701,559 A | 2/1955 | Cooper |
| 2,845,959 A | 8/1958 | Sidebotham |
| 2,978,787 A | 4/1961 | Liebig |
| 2,990,605 A | 7/1961 | Demsyk |
| 3,029,819 A | 4/1962 | Starks |

(Continued)

FOREIGN PATENT DOCUMENTS

| DE | 3640745 A1 | 6/1987 |
| DE | 3823060 A1 | 1/1989 |
| EP | 0 062 300 A2 | 10/1982 |
| EP | 0 221 570 A2 | 5/1987 |
| EP | 0 338 816 A2 | 10/1989 |

(Continued)

OTHER PUBLICATIONS

Dotter, Charles T. *Transluminally Placed Coilspring Endarterial Tube Grafts*, Investigative Radiology, pp. 329–332, Sep./Oct. 1969.

Dotter, Charles T., *Transluminal Expandable Nitinol Coil Stent Grafting: Preliminary Report*, Radiology Journal, pp. 259–260, Apr. 1983.

Cragg et al., *Non–Surgical Placement of Arterial Endoprostheses: A New Technique Using Nitinol Wire*, Radiology Journal, pp. 261–263, Apr. 1983.

Maass, et al., *Radiological Follow–Up of Transluminally Inserted Vascular Endoprostheses: An Experimental Study Using Expanding Spirals*, Radiology Journal, pp. 659–663, 1984.

(Continued)

*Primary Examiner*—Kevin T. Truong
(74) *Attorney, Agent, or Firm*—Fulwider Patton Lee & Utecht, LLP

(57) ABSTRACT

An apparatus and method is provided for stenting bifurcated vessels. A proximal angled stent is configured for implanting in a side-branch vessel wherein the proximal angled stent has an angulated portion that corresponds to the angle formed by the intersection of the side-branch vessel and the main vessel so that all portions of the side-branch vessel at the bifurcation are covered by the proximal angled stent. A main-vessel stent is provided for implanting in the main vessel, wherein the main-vessel stent has an aperture or stent cell that aligns with the opening to the side-branch vessel to permit unobstructed blood flow between the main vessel and the side-branch vessel. Side-branch and main-vessel catheter assemblies are advanced over a pair of guide wires for delivering, appropriately orienting, and implanting the proximal angled stent and the apertured stent.

5 Claims, 36 Drawing Sheets

U.S. PATENT DOCUMENTS

| | | |
|---|---|---|
| 3,096,560 A | 7/1963 | Liebig |
| 3,105,492 A | 10/1963 | Jeckel |
| 3,142,067 A | 7/1964 | Liebig |
| 3,657,744 A | 4/1972 | Ersek |
| 3,868,956 A | 3/1975 | Alfidi et al. |
| 3,908,662 A | 9/1975 | Razgulov et al. |
| 3,945,052 A | 3/1976 | Liebig |
| 3,993,078 A | 11/1976 | Bergentz et al. |
| 4,041,931 A | 8/1977 | Elliott et al. |
| 4,047,252 A | 9/1977 | Liebig et al. |
| 4,061,134 A | 12/1977 | Samuels et al. |
| 4,108,161 A | 8/1978 | Samuels et al. |
| 4,130,904 A | 12/1978 | Whalen |
| 4,140,126 A | 2/1979 | Choudhury |
| 4,159,719 A | 7/1979 | Haerr |
| 4,193,137 A | 3/1980 | Heck |
| 4,202,349 A | 5/1980 | Jones |
| 4,214,587 A | 7/1980 | Sakura, Jr. |
| 4,323,071 A | 4/1982 | Simpson |
| 4,387,952 A | 6/1983 | Slusher |
| 4,503,569 A | 3/1985 | Dotter |
| 4,504,354 A | 3/1985 | George et al. |
| 4,512,338 A | 4/1985 | Balko et al. |
| 4,516,972 A | 5/1985 | Samson |
| 4,517,687 A | 5/1985 | Liebig et al. |
| 4,531,933 A | 7/1985 | Norton et al. |
| 4,553,545 A | 11/1985 | Maass et al. |
| 4,560,374 A | 12/1985 | Hammerslag |
| 4,562,596 A | 1/1986 | Kornberg |
| 4,577,631 A | 3/1986 | Kreamer |
| 4,580,568 A | 4/1986 | Gianturco |
| 4,616,652 A | 10/1986 | Simpson |
| 4,617,932 A | 10/1986 | Kornberg |
| 4,619,246 A | 10/1986 | Molgaard-Nielsen et al. |
| 4,649,922 A | 3/1987 | Wiktor |
| 4,650,466 A | 3/1987 | Luther |
| 4,652,263 A | 3/1987 | Herweck et al. |
| 4,655,771 A | 4/1987 | Wallsten |
| 4,665,918 A | 5/1987 | Garza et al. |
| 4,681,110 A | 7/1987 | Wiktor |
| 4,693,249 A | 9/1987 | Schenck et al. |
| 4,706,671 A | 11/1987 | Weinrib |
| 4,728,328 A | 3/1988 | Hughes et al. |
| 4,732,152 A | 3/1988 | Wallsten et al. |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,760,849 A | 8/1988 | Kropf |
| 4,762,128 A | 8/1988 | Rosenbluth |
| 4,767,418 A | 8/1988 | Deininger et al. |
| 4,768,507 A | 9/1988 | Fischell et al. |
| 4,774,949 A | 10/1988 | Fogarty |
| 4,776,337 A | 10/1988 | Palmaz |
| 4,787,899 A | 11/1988 | Lazarus |
| 4,793,348 A | 12/1988 | Palmaz |
| 4,795,458 A | 1/1989 | Regan |
| 4,795,465 A | 1/1989 | Marten |
| 4,800,882 A | 1/1989 | Gianturco |
| 4,817,624 A | 4/1989 | Newbower |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,872,874 A | 10/1989 | Taheri |
| 4,877,030 A | 10/1989 | Beck et al. |
| 4,878,906 A | 11/1989 | Lindemann et al. |
| 4,886,062 A | 12/1989 | Wiktor |
| 4,887,997 A | 12/1989 | Okada |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,921,479 A | 5/1990 | Grayzel |
| 4,922,905 A | 5/1990 | Strecker |
| 4,923,464 A | 5/1990 | DiPisa, Jr. |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,969,896 A | 11/1990 | Shors |
| 4,986,831 A | 1/1991 | King et al. |
| 4,988,356 A | 1/1991 | Crittenden et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,047,050 A | 9/1991 | Arpesdani |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,877 A | 3/1992 | Pinchuk |
| 5,100,429 A | 3/1992 | Sinofsky et al. |
| 5,102,417 A | 4/1992 | Palmaz |
| 5,104,399 A | 4/1992 | Lazarus |
| 5,104,404 A | 4/1992 | Wolff |
| 5,108,416 A | 4/1992 | Ryan et al. |
| 5,108,417 A | 4/1992 | Sawyer |
| 5,108,424 A | 4/1992 | Hoffman, Jr. et al. |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,127,919 A | 7/1992 | Ibrahim et al. |
| 5,133,732 A | 7/1992 | Wiktor |
| 5,135,536 A | 8/1992 | Hillstead |
| 5,156,619 A | 10/1992 | Ehrenfeld |
| 5,158,548 A | 10/1992 | Lau et al. |
| 5,161,547 A | 11/1992 | Tower |
| 5,163,951 A | 11/1992 | Pinchuk et al. |
| 5,163,952 A | 11/1992 | Froix |
| 5,163,958 A | 11/1992 | Pinchuk |
| 5,171,262 A | 12/1992 | MacGregor |
| 5,178,630 A | 1/1993 | Schmitt |
| 5,178,634 A | 1/1993 | Ramos Martinez |
| 5,180,368 A | 1/1993 | Garrison |
| 5,183,085 A | 2/1993 | Timmermans |
| 5,192,297 A | 3/1993 | Hull |

| Patent Number | Date | Inventor |
|---|---|---|
| 5,192,307 A | 3/1993 | Wall |
| 5,192,311 A | 3/1993 | King et al. |
| 5,195,984 A | 3/1993 | Schatz |
| 5,197,976 A | 3/1993 | Herweck et al. |
| 5,197,977 A | 3/1993 | Hoffman, Jr. et al. |
| 5,197,978 A | 3/1993 | Hess |
| 5,217,482 A | 6/1993 | Keith |
| 5,222,971 A | 6/1993 | Willard et al. |
| 5,226,913 A | 7/1993 | Pinchuk |
| 5,234,456 A | 8/1993 | Silvestrini |
| 5,242,394 A | 9/1993 | Tremulis |
| 5,242,399 A | 9/1993 | Lau et al. |
| 5,242,452 A | 9/1993 | Inoue |
| 5,282,823 A | 2/1994 | Schwartz et al. |
| 5,282,824 A | 2/1994 | Gianturco |
| 5,290,295 A | 3/1994 | Querals et al. |
| 5,290,305 A | 3/1994 | Inoue |
| 5,292,331 A | 3/1994 | Boneau |
| 5,304,200 A | 4/1994 | Spaulding |
| 5,304,220 A | 4/1994 | Maginot |
| 5,314,444 A | 5/1994 | Gianturco |
| 5,314,472 A | 5/1994 | Fontaine |
| 5,316,023 A | 5/1994 | Palmaz et al. |
| 5,330,500 A | 7/1994 | Song |
| 5,344,426 A | 9/1994 | Lau et al. |
| 5,354,308 A | 10/1994 | Simon et al. |
| 5,356,433 A | 10/1994 | Rowland et al. |
| 5,360,401 A | 11/1994 | Turnland et al. |
| 5,360,443 A | 11/1994 | Barone et al. |
| 5,368,566 A | 11/1994 | Crocker |
| 5,372,600 A | 12/1994 | Beyar et al. |
| 5,378,239 A | 1/1995 | Termin et al. |
| 5,383,892 A | 1/1995 | Cardon et al. |
| 5,405,378 A | 4/1995 | Strecker |
| 5,421,955 A | 6/1995 | Lau et al. |
| 5,423,745 A | 6/1995 | Todd et al. |
| 5,423,885 A | 6/1995 | Williams |
| 5,443,497 A | 8/1995 | Venbrux |
| 5,443,498 A | 8/1995 | Fontaine |
| 5,445,646 A | 8/1995 | Euteneuer et al. |
| 5,449,373 A | 9/1995 | Pinchasik et al. |
| 5,456,694 A | 10/1995 | Marin et al. |
| 5,456,712 A | 10/1995 | Maginot |
| 5,458,615 A | 10/1995 | Klemm et al. |
| 5,476,476 A | 12/1995 | Hillstead |
| 5,484,449 A | 1/1996 | Amundson et al. |
| 5,507,768 A | 4/1996 | Lau et al. |
| 5,514,154 A | 5/1996 | Lau et al. |
| 5,522,880 A | 6/1996 | Barone et al. |
| 5,527,355 A | 6/1996 | Ahn |
| 5,545,132 A | 8/1996 | Fagan et al. |
| 5,562,724 A | 10/1996 | Vorwerk et al. |
| D376,011 S | 11/1996 | Nunokawa |
| 5,571,135 A | 11/1996 | Fraser et al. |
| 5,571,170 A | 11/1996 | Palmaz et al. |
| 5,571,171 A | 11/1996 | Barone et al. |
| 5,571,173 A | 11/1996 | Parodi |
| 5,575,817 A | 11/1996 | Martin |
| 5,578,072 A | 11/1996 | Barone et al. |
| 5,591,228 A | 1/1997 | Edoga |
| 5,591,229 A | 1/1997 | Parodi |
| 5,603,721 A | 2/1997 | Lau et al. |
| 5,609,627 A | 3/1997 | Goicoechea et al. |
| 5,613,980 A | 3/1997 | Chauhan |
| 5,617,878 A | 4/1997 | Taheri |
| 5,626,604 A | 5/1997 | Cottone, Jr. |
| 5,632,763 A | 5/1997 | Glastra |
| 5,639,278 A | 6/1997 | Dereume et al. |
| 5,643,340 A | 7/1997 | Nunokawa |
| 5,653,690 A | 8/1997 | Booth et al. |
| 5,653,691 A | 8/1997 | Rupp et al. |
| 5,653,727 A | 8/1997 | Wiktor |
| 5,669,924 A | 9/1997 | Shaknovich |
| 5,676,696 A | 10/1997 | Marcade |
| 5,676,697 A | 10/1997 | McDonald |
| 5,683,450 A | 11/1997 | Goicoechea et al. |
| 5,683,452 A | 11/1997 | Barone et al. |
| 5,683,453 A | 11/1997 | Palmaz |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,517 A | 12/1997 | Marin et al. |
| 5,709,713 A | 1/1998 | Evans et al. |
| 5,713,363 A | 2/1998 | Seward et al. |
| 5,713,917 A | 2/1998 | Leonhardt et al. |
| 5,716,396 A | 2/1998 | Williams, Jr. |
| 5,720,726 A | 2/1998 | Marcadis et al. |
| 5,733,303 A | 3/1998 | Israel et al. |
| 5,733,325 A | 3/1998 | Robinson et al. |
| 5,735,893 A | 4/1998 | Lau et al. |
| 5,749,825 A | 5/1998 | Fischell et al. |
| 5,755,734 A | 5/1998 | Richter et al. |
| 5,755,735 A | 5/1998 | Richter et al. |
| 5,776,180 A | 7/1998 | Goicoechea et al. |
| 5,782,855 A | 7/1998 | Lau et al. |
| 5,782,906 A | 7/1998 | Marshall et al. |
| 5,800,508 A | 9/1998 | Goicoechea et al. |
| 5,800,520 A | 9/1998 | Fogarty et al. |
| 5,800,521 A | 9/1998 | Orth |
| 5,810,871 A | 9/1998 | Tuckey et al. |
| 5,817,152 A | 10/1998 | Birdsall et al. |
| 5,830,217 A | 11/1998 | Ryan |
| 5,836,965 A | 11/1998 | Jendersee et al. |
| 5,893,852 A | 4/1999 | Morales |
| 5,893,887 A | 4/1999 | Jayaraman |
| 5,895,407 A | 4/1999 | Jayaraman |
| 5,902,332 A | 5/1999 | Schatz |
| 5,913,895 A | 6/1999 | Burpee et al. |
| 5,916,234 A | 6/1999 | Lam |
| 5,984,964 A | 11/1999 | Roberts et al. |
| 5,997,468 A | 12/1999 | Wolff et al. |
| 6,030,413 A | 2/2000 | Lazarus |
| 6,066,168 A | 5/2000 | Lau et al. |
| 6,086,604 A | 7/2000 | Fischell et al. |
| 6,096,073 A | 8/2000 | Webster |
| 6,146,358 A | 11/2000 | Rowe |
| 6,165,195 A | 12/2000 | Wilson et al. |
| 6,179,868 B1 | 1/2001 | Burpee et al. |
| 6,183,506 B1 | 2/2001 | Penn et al. |
| 6,190,403 B1 | 2/2001 | Fischell et al. |
| 6,217,608 B1 | 4/2001 | Penn et al. |
| 6,749,628 B1 * | 6/2004 | Callol et al. ............... 623/1.35 |
| 6,780,174 B2 * | 8/2004 | Mauch ............... 623/1.35 |
| 2002/0058988 A1 | 5/2002 | Fischell et al. |
| 2002/0058989 A1 | 5/2002 | Chen et al. |

FOREIGN PATENT DOCUMENTS

| | | |
|---|---|---|
| EP | 0 361 192 A3 | 4/1990 |
| EP | 0 364 787 A1 | 4/1990 |
| EP | 0 372 789 A3 | 6/1990 |
| EP | 0 380 668 A1 | 8/1990 |
| EP | 0 407 951 A3 | 1/1991 |
| EP | 9 408 245 A1 | 1/1991 |
| EP | 0 421 729 A2 | 4/1991 |
| EP | 0 423 916 A1 | 4/1991 |
| EP | 0 428 479 A1 | 5/1991 |
| EP | 0 461 791 A1 | 12/1991 |
| EP | 0 466 518 A3 | 1/1992 |
| EP | 0466 518 A3 | 1/1992 |
| EP | 0 517 075 B1 | 12/1992 |
| EP | 0 540 290 A2 | 5/1993 |

| | | | |
|---|---|---|---|
| EP | 0 541 443 A1 | 5/1993 | |
| EP | 0 747 020 A2 | 12/1996 | |
| EP | 0 804 907 A | 11/1997 | |
| EP | 0 807 424 A2 | 11/1997 | |
| FR | 2 677 872 | 12/1992 | |
| FR | 2 737 969 A | 2/1997 | |
| GB | 2 070 490 A | 9/1981 | |
| GB | 2 135 585 A | 11/1983 | |
| JP | 58-501458 | 9/1983 | |
| JP | 62-213762 | 9/1987 | |
| JP | 62-231657 | 10/1987 | |
| JP | 62-235496 A | 10/1987 | |
| JP | 63-214264 | 9/1988 | |
| JP | 63-246178 | 10/1988 | |
| JP | 01083685 A | 3/1989 | |
| JP | 64-83685 | 3/1989 | |
| JP | 1-299550 | 12/1989 | |
| JP | 2-174859 | 7/1990 | |
| JP | 2 255157 | 10/1990 | |
| JP | 03009745 A | 1/1991 | |
| JP | 03009746 A | 1/1991 | |
| JP | 3-57465 | 3/1991 | |
| JP | 3-151983 | 6/1991 | |
| JP | 4-25755 | 2/1992 | |
| SU | 1217402 A | 3/1986 | |
| SU | 1318235 A1 | 6/1987 | |
| SU | 1389778 A2 | 4/1988 | |
| SU | 1457921 A1 | 2/1989 | |
| SU | 1482714 A2 | 5/1989 | |
| WO | WO 89/01798 | 3/1989 | |
| WO | WO 89/08433 | 9/1989 | |
| WO | WO 91/07139 | 5/1991 | |
| WO | WO 92/06734 | 4/1992 | |
| WO | WO 92/09246 | 6/1992 | |
| WO | WO 95/16406 | 6/1995 | |
| WO | WO 95/21592 | 8/1995 | |
| WO | WO 96/13455 | 8/1996 | |
| WO | WO 96/24306 | 8/1996 | |
| WO | WO 96/24308 | 8/1996 | |
| WO | WO 96/34580 A | 11/1996 | |
| WO | WO 98/19628 | 10/1997 | |
| WO | WO 97/41803 | 11/1997 | |
| WO | WO 97/45073 | 12/1997 | |
| WO | WO 98/36709 | 2/1998 | |
| WO | WO 99/34749 | 7/1999 | |

OTHER PUBLICATIONS

C.R. Bard, *PE Plus Peripheral Balloon Dilation Catheter,* C.R. Bard, Inc., Aug. 1985.

Wright, et al., *Percutaneous Endovascular Stents: An Experimental Evaluation,* Radiology Journal, pp. 69–72, 1985.

Palmaz et al., *Expandable Intraluminal Graft: A Preliminary Study,* Radiology Journal, pp. 73–77, 1985.

Duprat et al., *Flexible Balloon–Expanded Stent for Small Vessels,* Radiology Journal, pp. 276–278 (1987).

Yoshioka et al., *Self–Expanding Endovascular Graft: An Experimental Study in Dogs,* American Journal of Roentgeriology, pp. 673–676, vol. 151, Oct. 1988.

Rosch, Jr., M.D. et al., *Transjugular Intrahepatic Portacaval Shunt: An Experimental Work,* The American Journal of Surgery, pp. 588–592, vol. 121, May 1971.

70th *Scientific Assembly and Annual Meeting: Scientific Program,* Radiology, Washington, D.C., Nov. 25–30, 1984, special Edition, vol. 153(P).

Charnsangavej, D., M.D. et al., *Endovascular Stent for Use in Aortic Dissection: An In Vitro Experiment,* Radiology, pp. 323–324. vol. 157. No. 2, Nov. 1985.

72nd *Scientific Assembly and Annual Meeting: RSNA Scientific Program,* Radiology, Chicago: Nov. 30–Dec. 5, 1986, Special Edition, vol. 161(P).

Wallace, Michael J., et al., *Tracheobronchia Tree: Expandable Metallic Stents Used in Experimental and Clinical Applications (Work in Progess),* Radiology, pp. 309–312, vol. 158, Feb. 1986.

*Program: Day 2* (Nov. 18) The Radiological Society of North America, Radiology, Chicago: Nov. 30–Dec. 5, 1986, Special Edition, vol. 161(P).

Charnsangavej, Chusilp, M.D., et al., *Stenosis of the Vena Cava: Preliminary Assessment of Treatment with Expandable Metallic Stents,* Radiology, pp. 295–298, vol. 161, Nov. 1986.

Rosch, Josef, M.D., et al., *Experimental Intrahepatic Portacaval Anastomosis: Use of Expandable Gianturco Stents,* Radiology, pp. 481–485, vol. 162, Feb. 1987.

Rosch, Josef, M.D., et al., *Gianturco Expandable Stents in Experimental and Clinical Use,* paper presented at The Twelfth Annual Course on "Diagnostic Angiography and Interventional Radiology" Mar. 23–26, 1987 (Pittsburgh, Pennsylvania).

Finci, Leo, M.D., et al., *Percutaneous Transluminal Coronary Angioplasty of a Bifurcation Narrowing Using the Kissing Wire Monorail Balloon Technique,* The American Journal of Cardiology, pp. 375–376, vol. 60, Aug. 1987.

Lawrence, David D., Jr., M.D., et al., *Percutaneous Endovascular Graft: Experimental Evaluation,* Radiology, pp. 357–360, vol. 163, May 1987.

Rosch, Josef, M.D., et al., *Gianturco Expandable Wire Stents in the Treatment of Superior Vena Cava Syndrome Recurring after Maximum–Tolerance Radiation,* Cancer, pp. 1243–1246, vol. 60, Sep. 1987.

Bonzel, T., et al., *The Sliding Rail System (Monorail): Descriptionof a New Technique for Intravascular Instumentation and Its Application to Coronary Angioplasty,* Kardiologie, Supplement 6, pp. 119–122, 1987.

Rosch, Josef, M.D., et al., *Modified Gianturco Expandable Wire Stents in Experimental and Clinical Use,* Annales de Radiologie, pp. 100–103, vol. 31, No. 2, 1988.

Yoshioka et al., *Development and Clinical Application of Biliary Endoprosthesis Using Expandable Metallic Stents,* Japan Radiological Society, 1988, vol. 48, No. 9, pp. 1183–1185 (with translation).

Mirich, et al., *Percutaneously Placed Endovascular Grafts for Aoertic Aneurysms: Feasibility Study,* Radiology, 1989, part 2, pp. 1033–1037.

Furui, Shigeru, M.D., et al., *Hepatic Inferior Vena Cava Obstruction: Treatment of Two Types with Gianturco Expandable Metallic Stents,* Radiology, pp. 665–670, Sep. 1990.

Kaltenbach, M., Prof. Dr., Abstracts, Zeitschrift fur Kardiologie, Apr. 3, 1991 (German only).

van der Geissen, Willem J., et al., *Coronary Stenting with a New, Radiopaque Balloon–Expandable Endoprosthesis in Pigs,* Circulation, vol. 83, No. 5, pp. 93–149, May 1991.

Strupp, G., et al., *Clinical and Angiographic Short and Medium Term Results after Coronary Stenting,* Zietschrift fur Kardiologie, Sep. 9, 1992 (German with English language summary).

Harrington, J.D., et al., *The Palmaz–Schatz Stent,* Handbook of Cardiovascular Interventions/Vascular Internventions, pp. 563–572 (undated).

Parodi, J.C., MD et al., *Transfemoral Intraluminal Graft Implantation for Abdominal Aortic Aneurysms*, Dept. of Vascular Surgery, Instituto Cardiovascular de Buenos Aires, Buenos Aires, Argentina and the Dept. of Radiology, University of Texas, San Antonio, Texas.

Chuter, Timothy A.M., et al., *Transfemoral Endovascular Aortic Graft Placement*, Section of Vaqscular Surgery, University of Rochester, Rochester, NY, 1992.

* cited by examiner

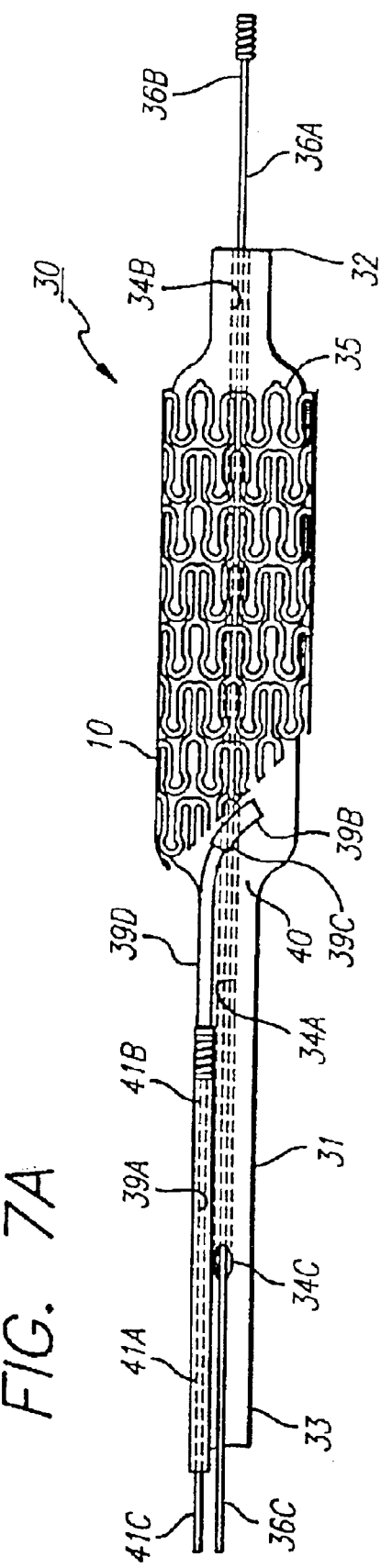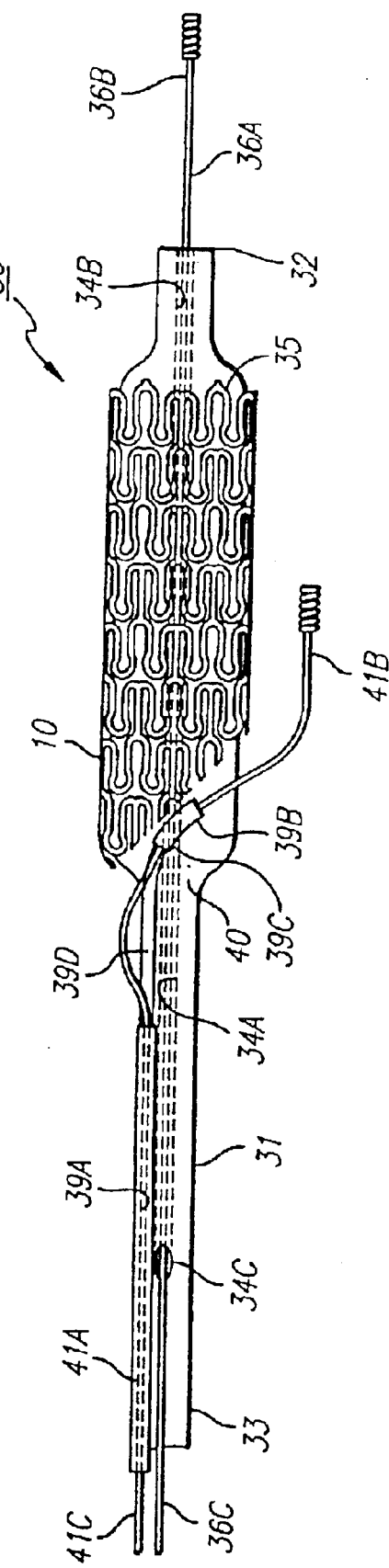
FIG. 7A
FIG. 7B

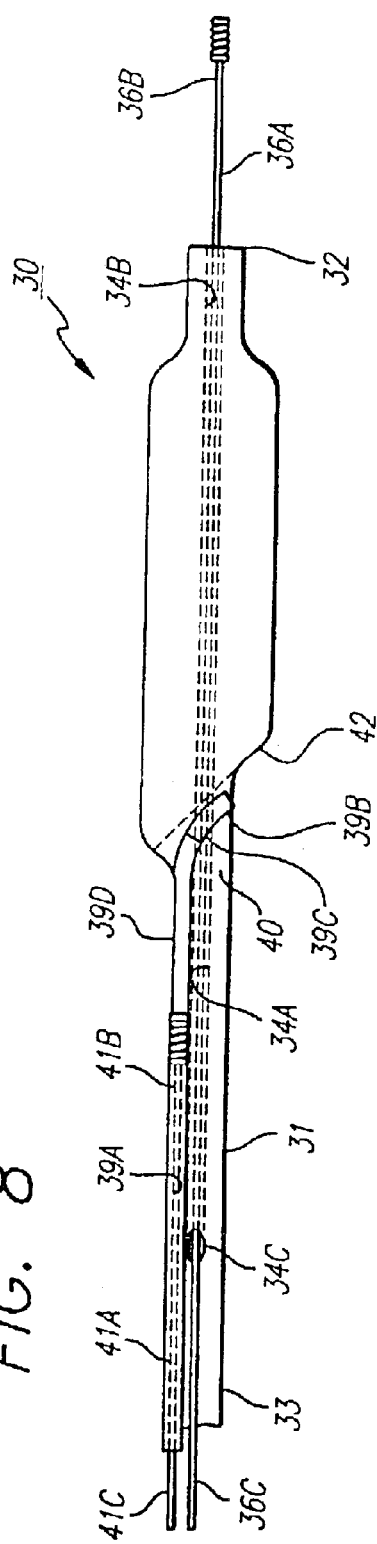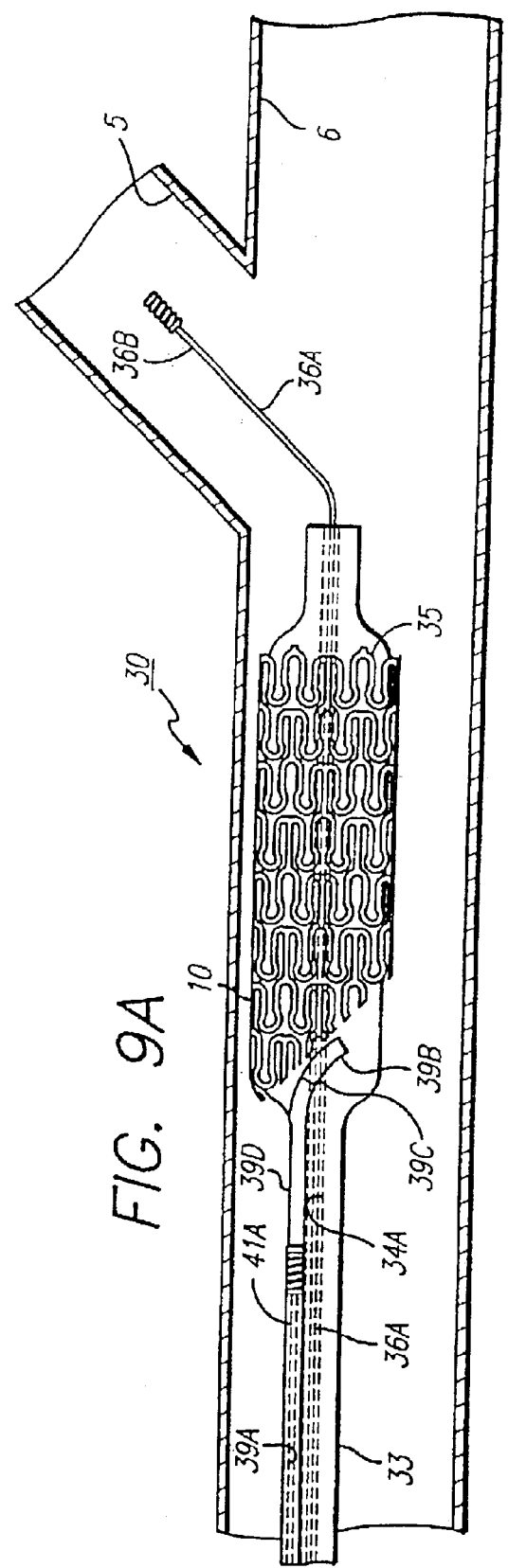

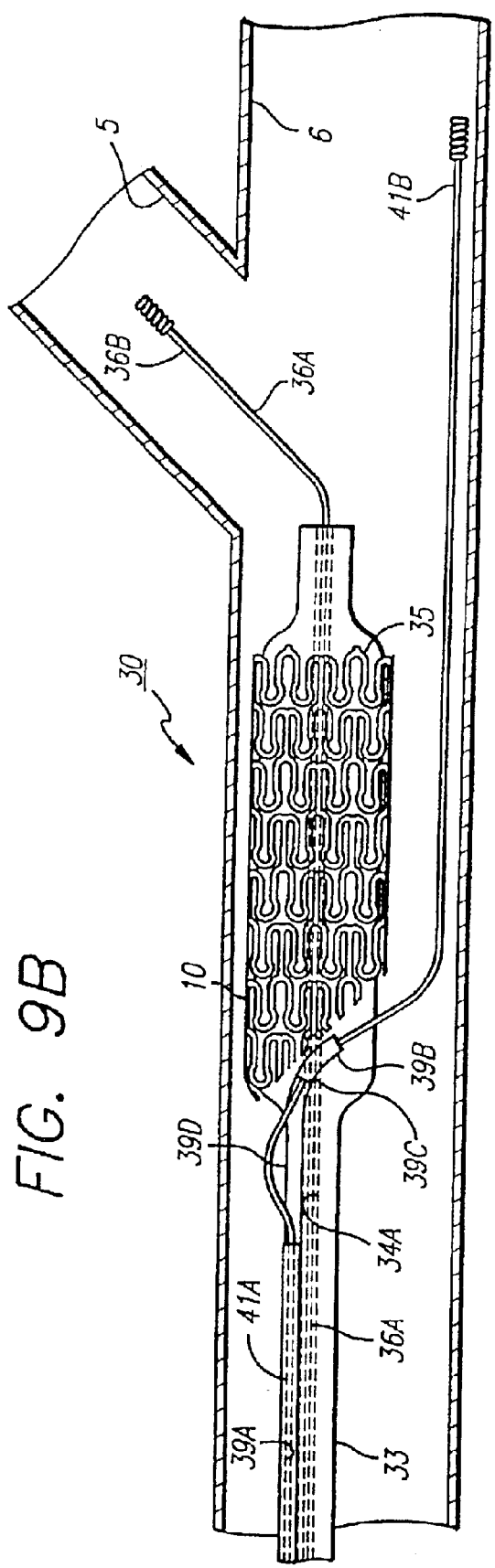

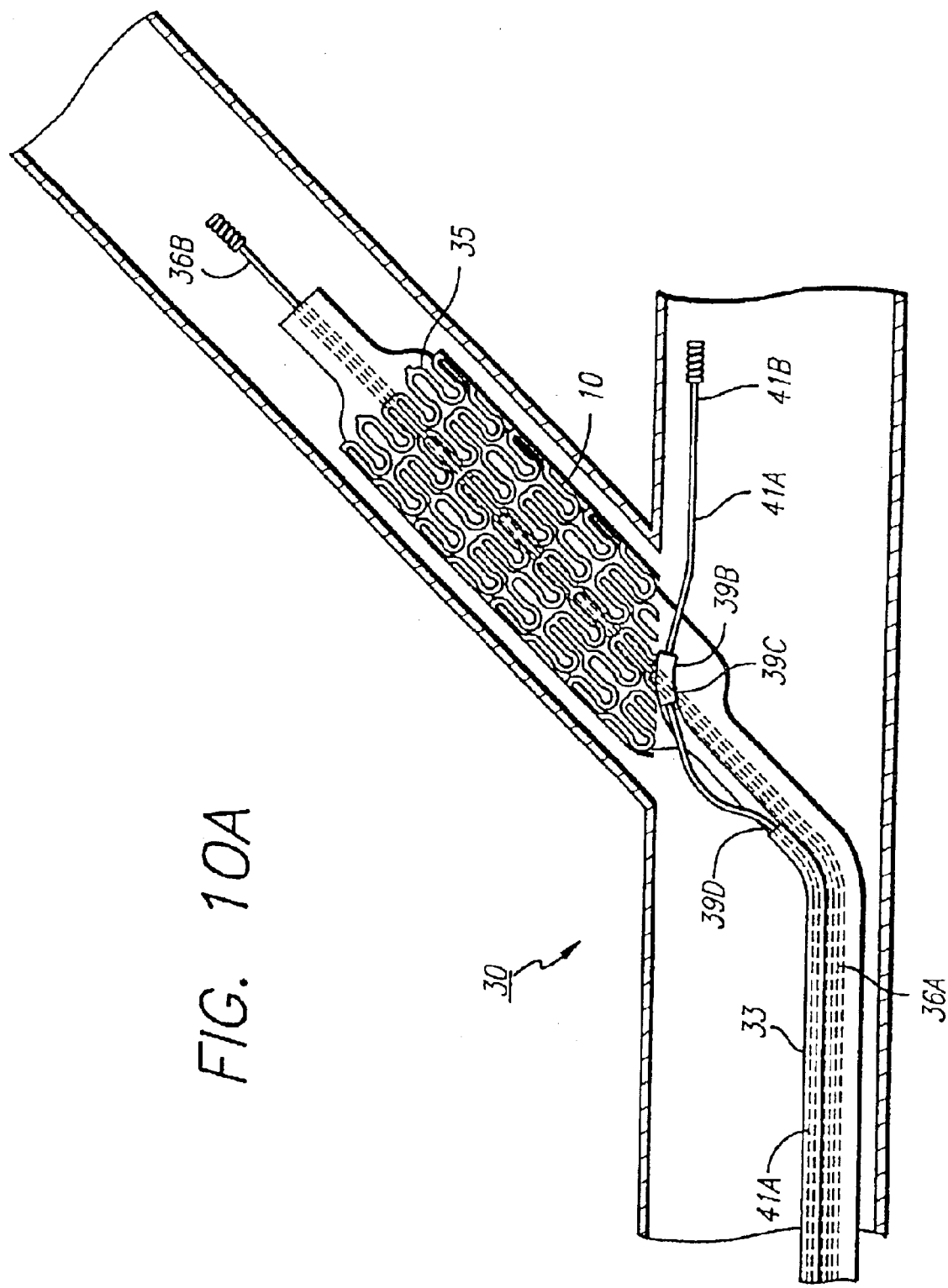

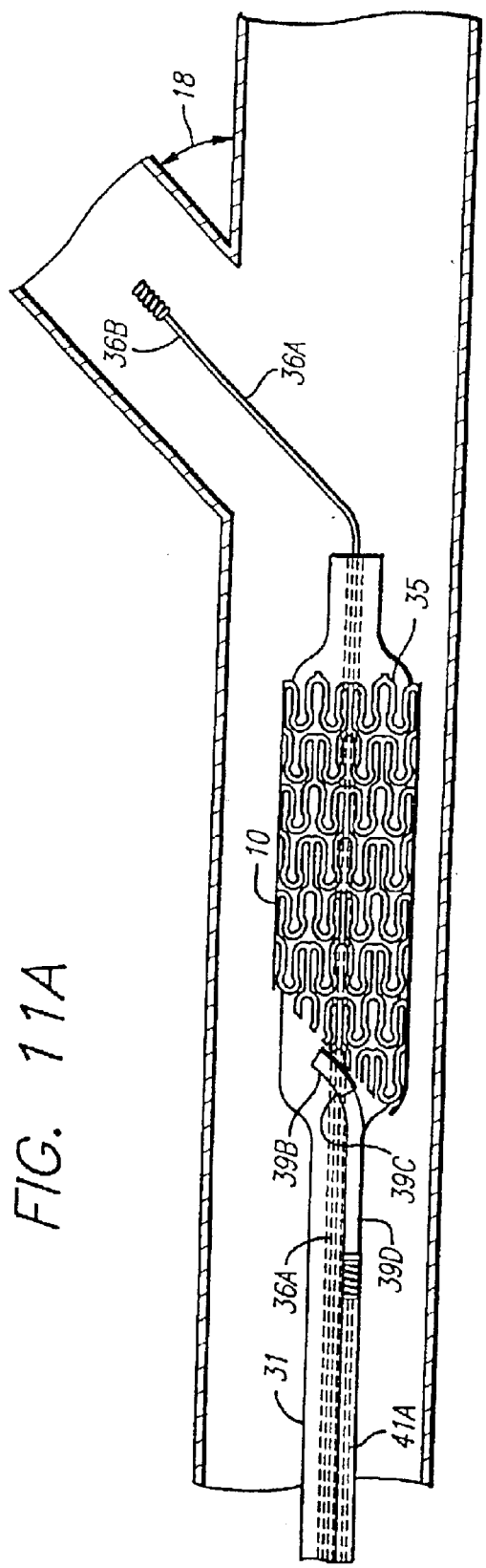
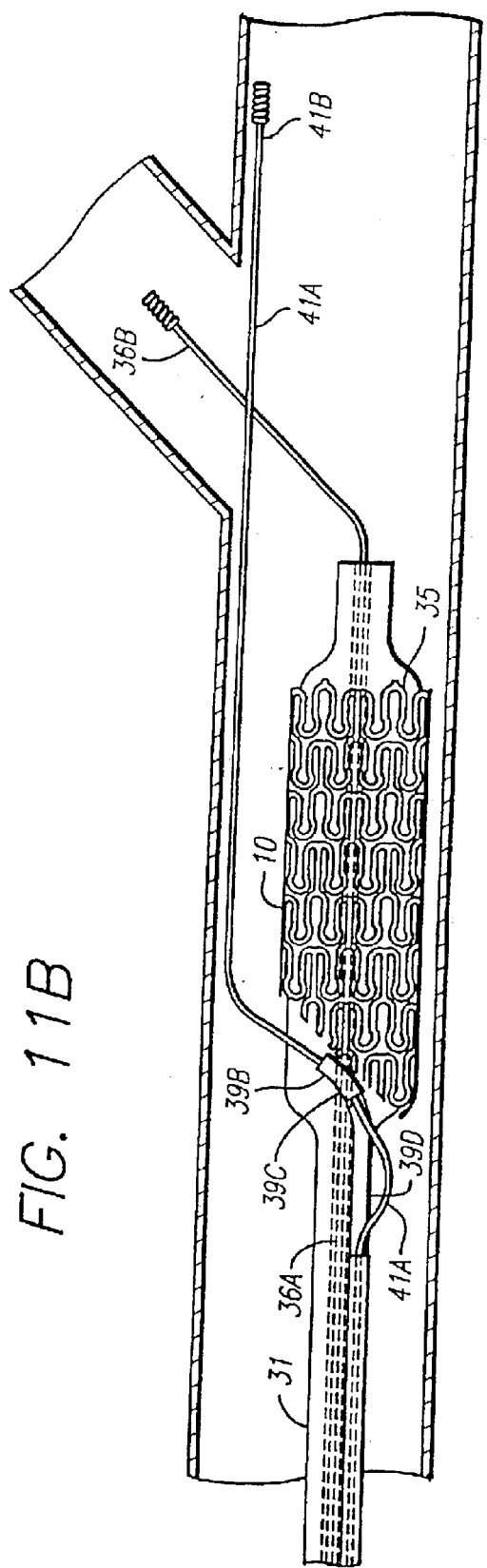
FIG. 11A
FIG. 11B

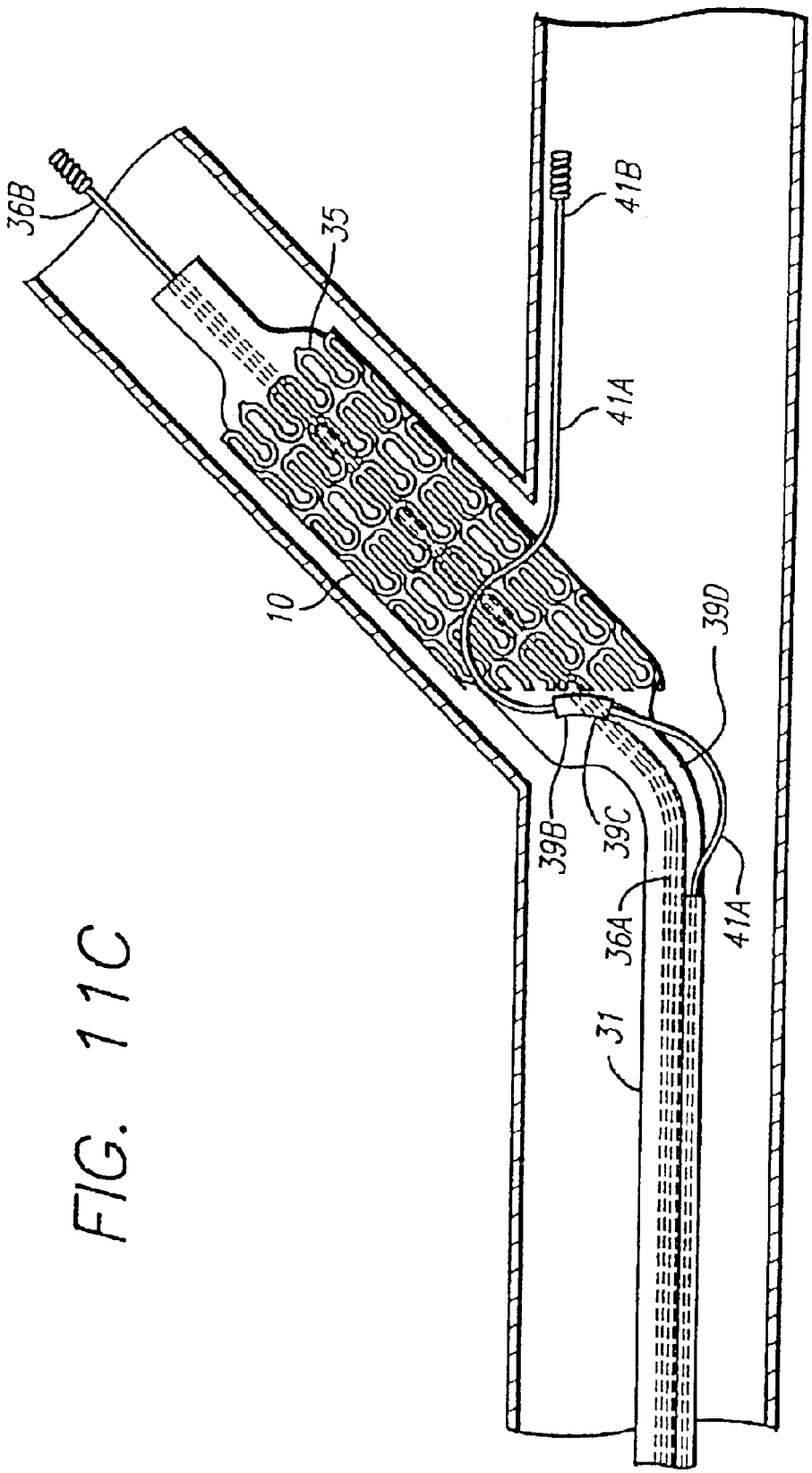

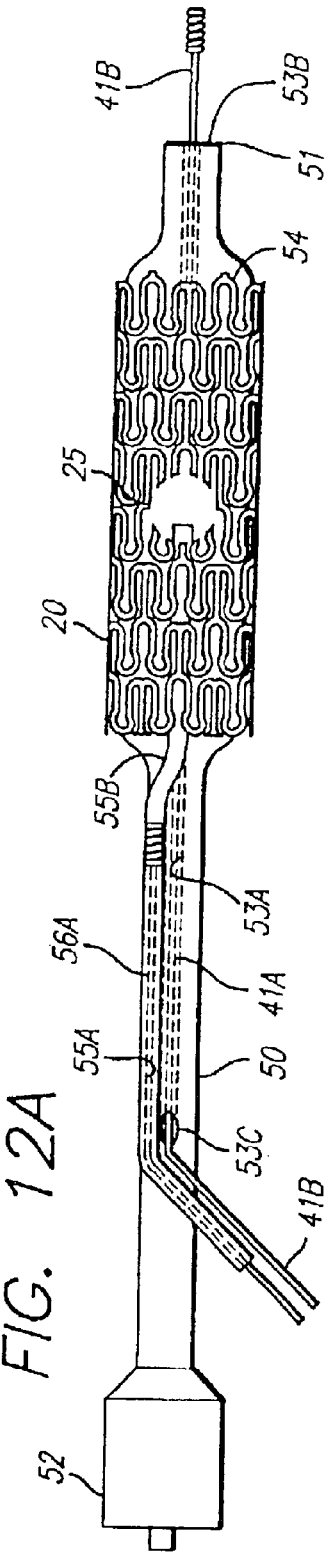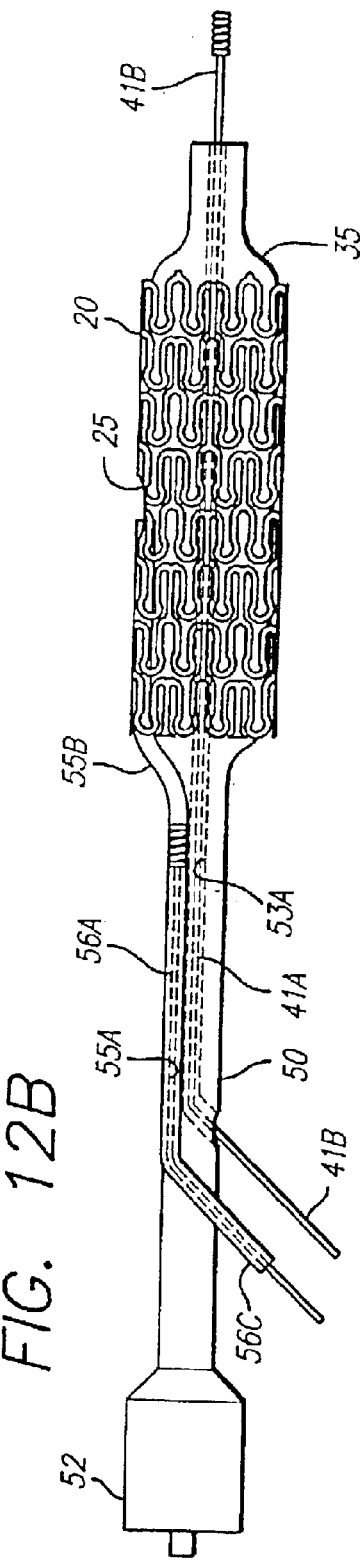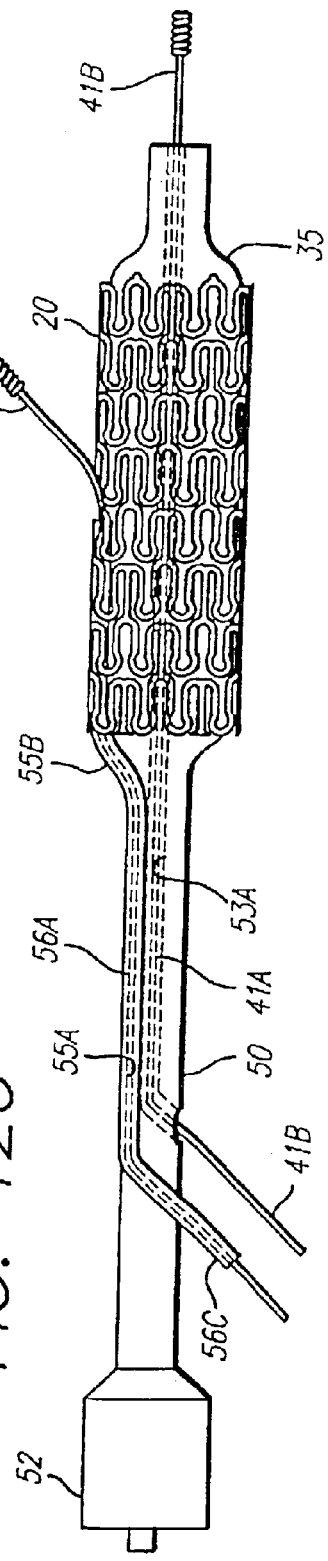

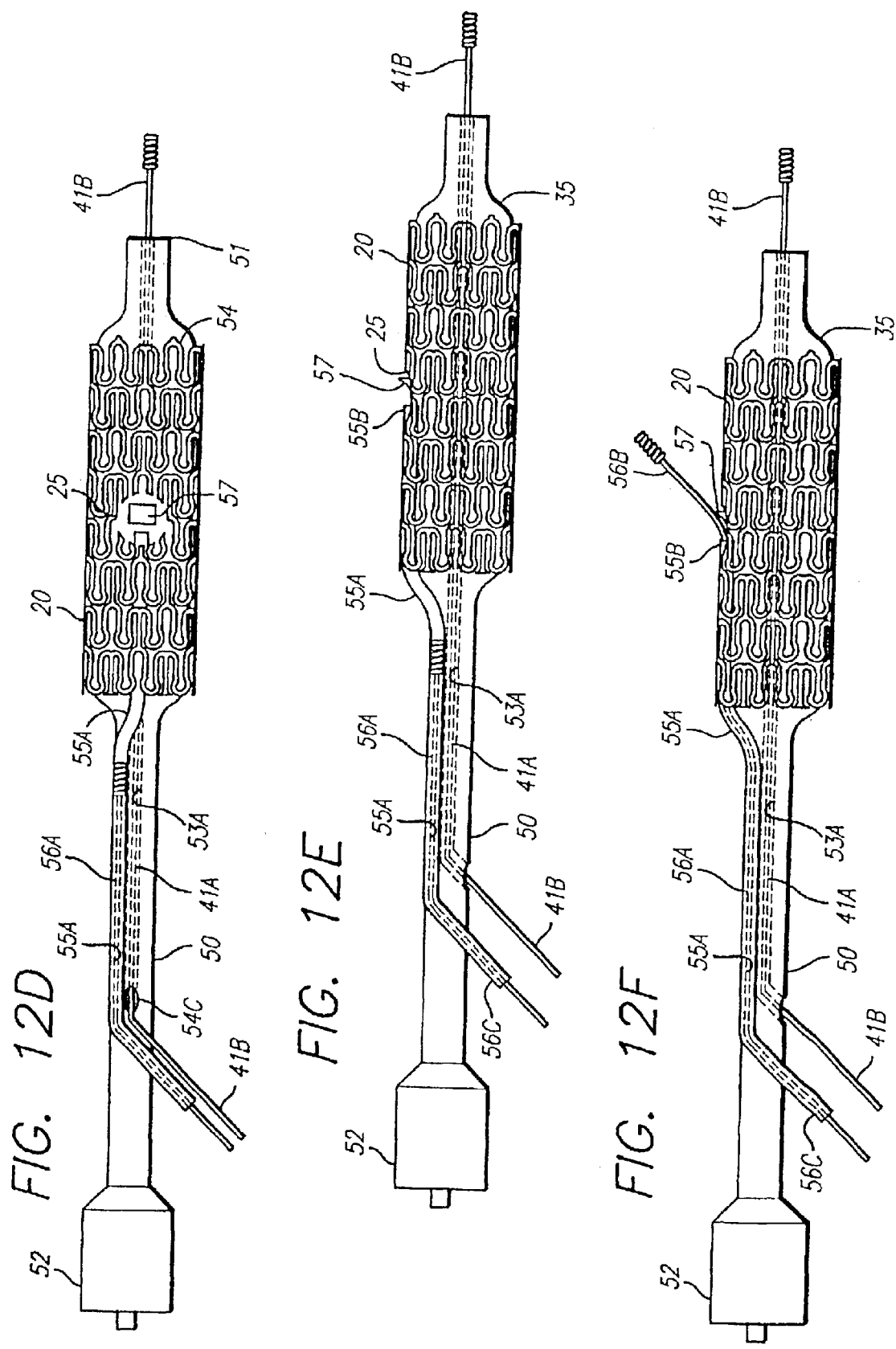

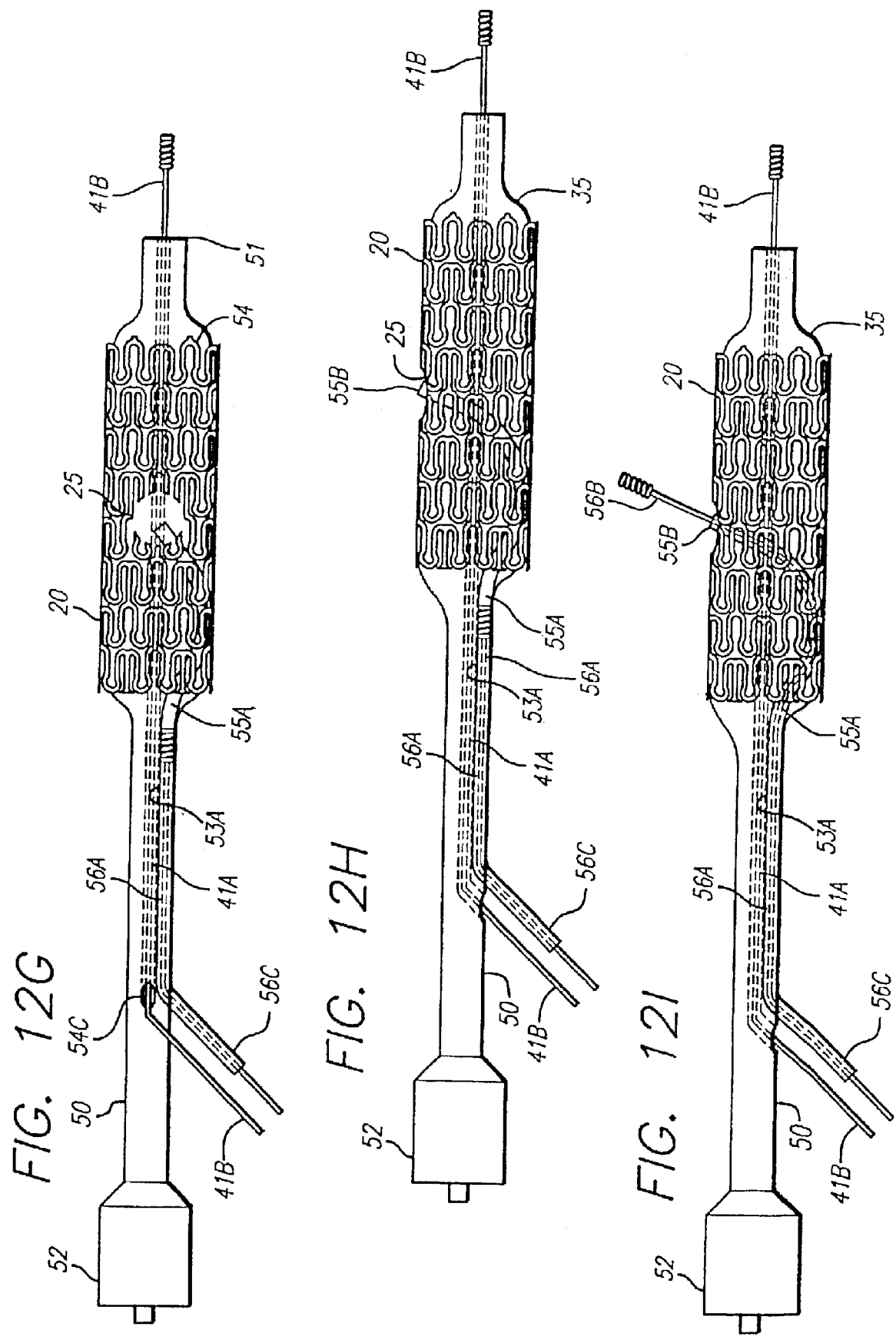

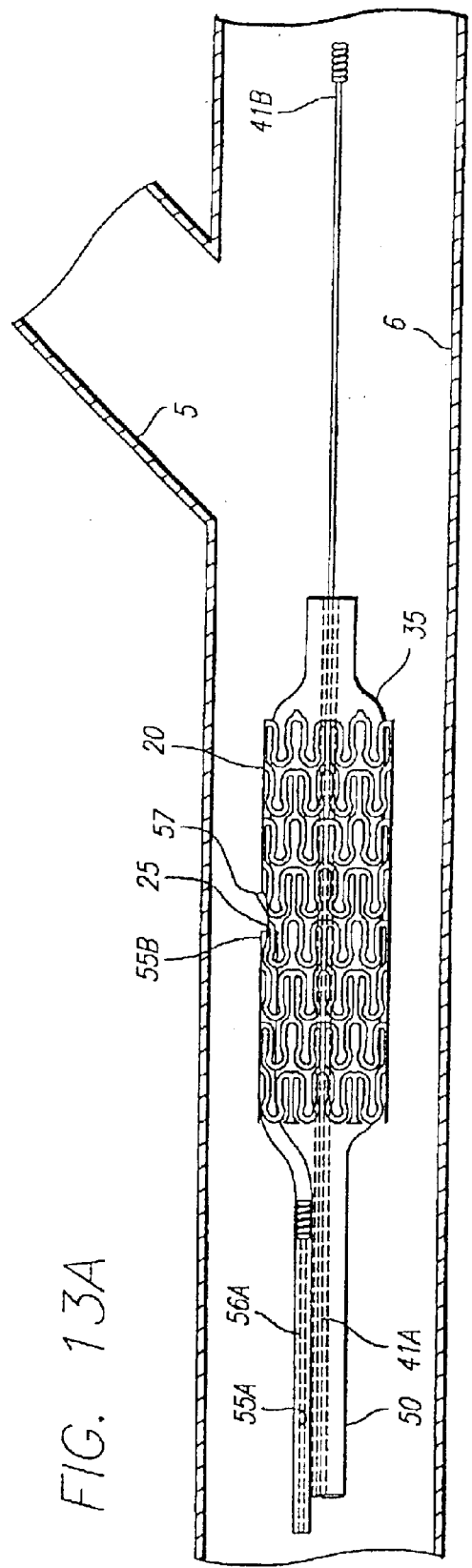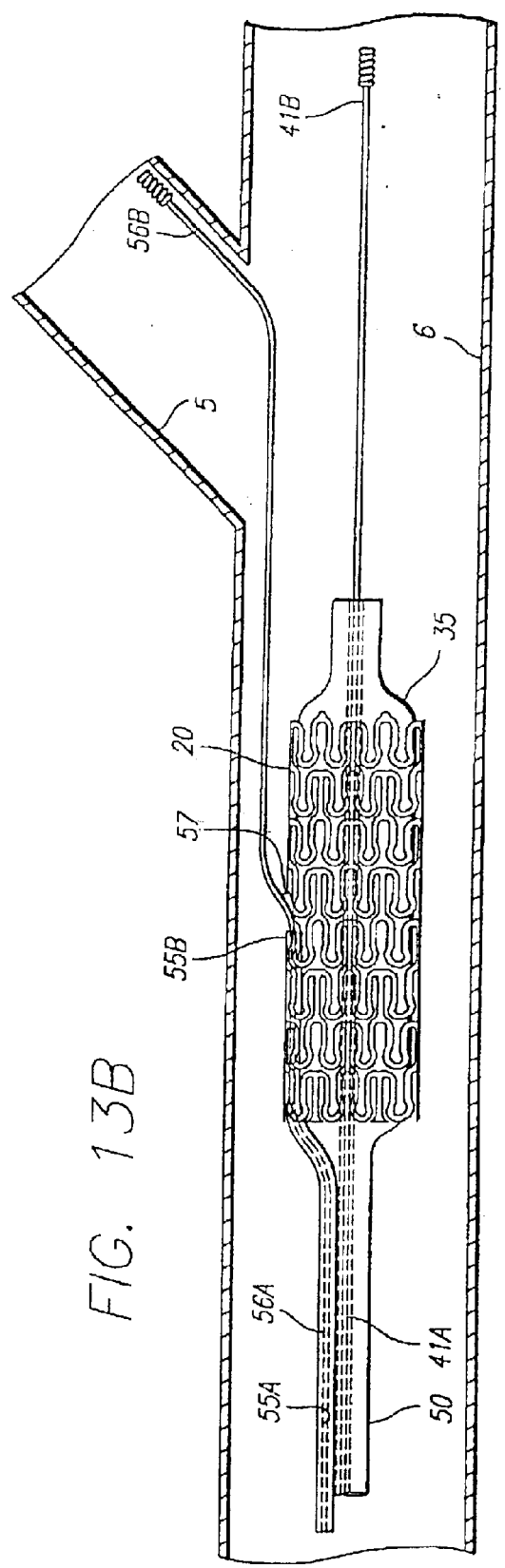

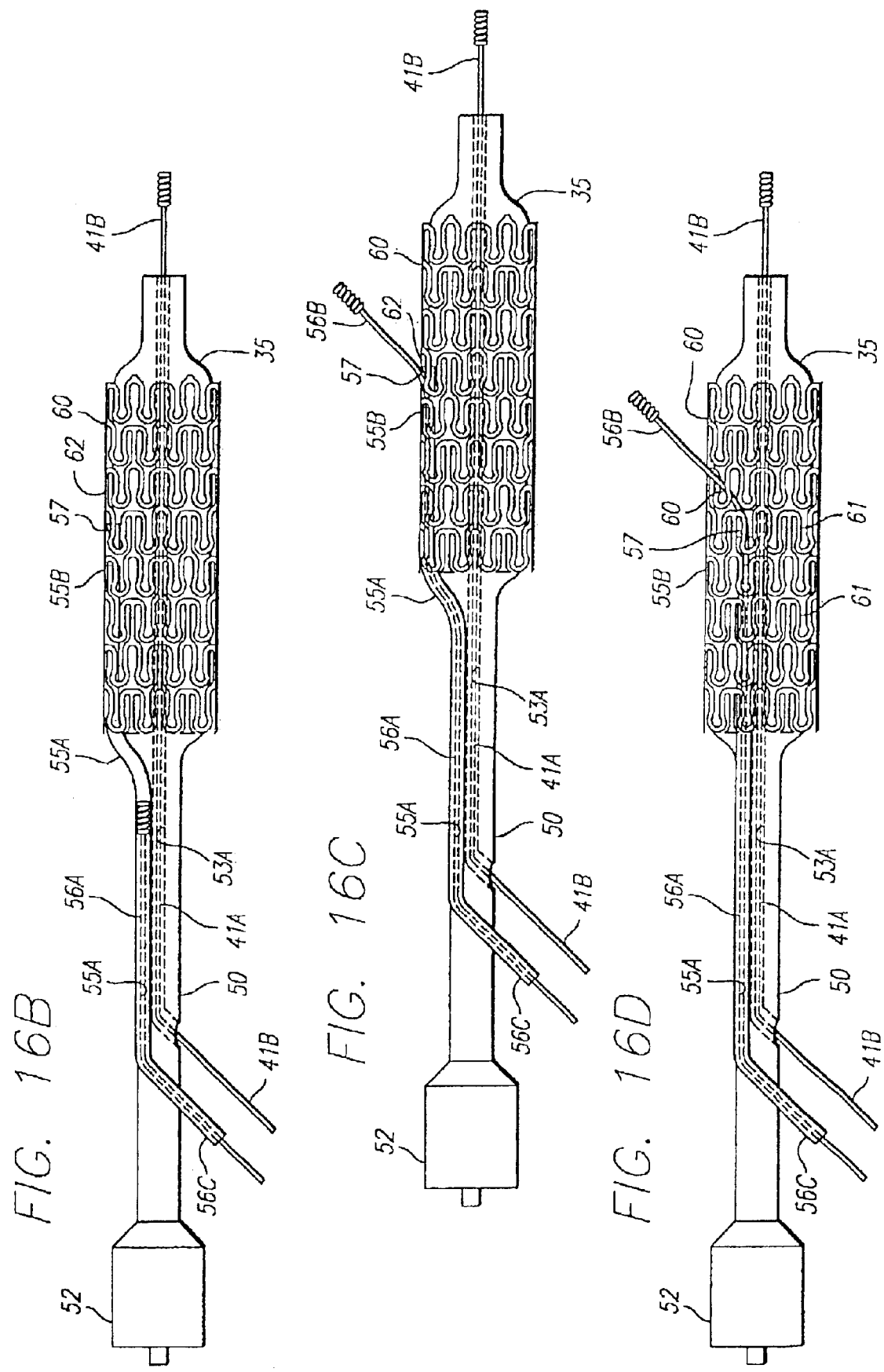

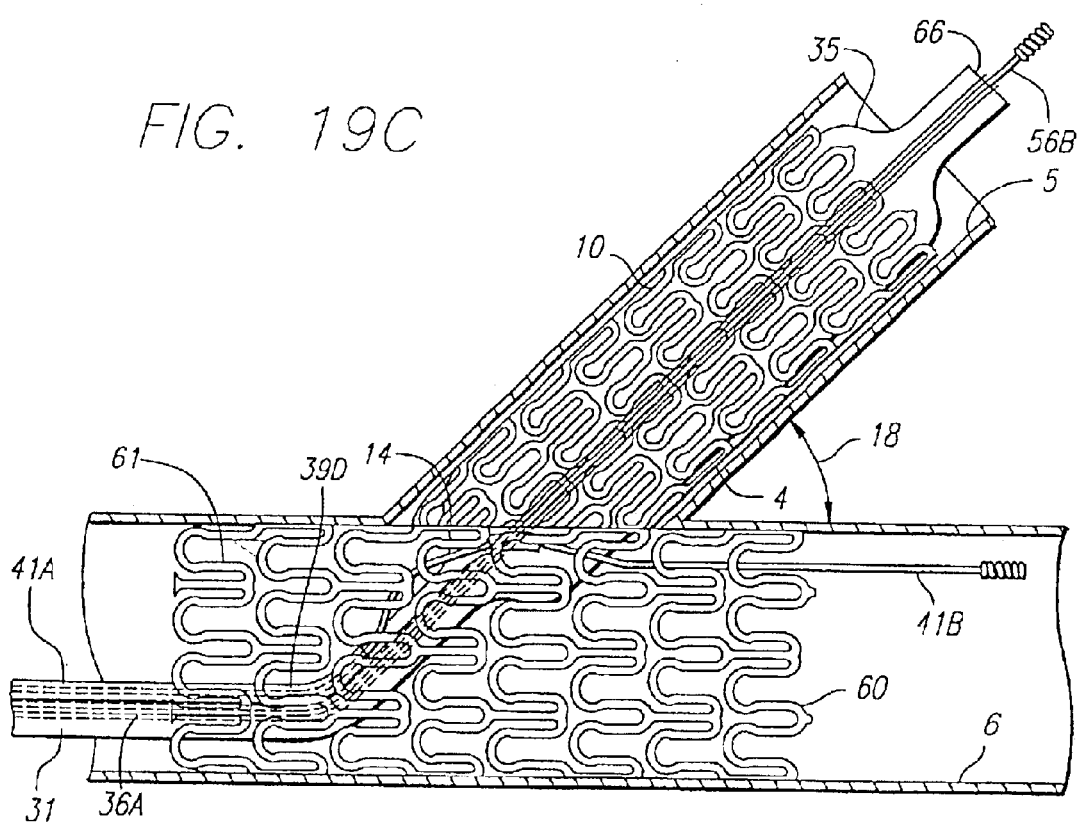
FIG. 19C
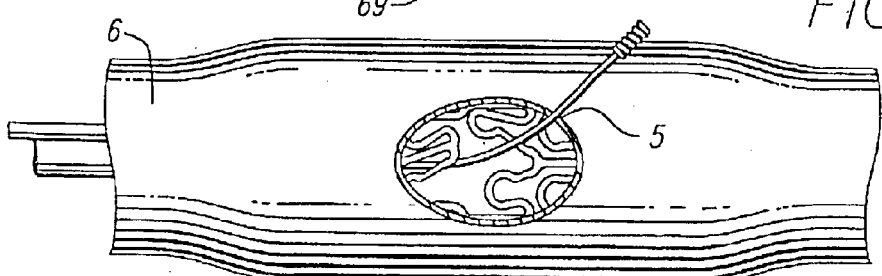
FIG. 19D
FIG. 19E
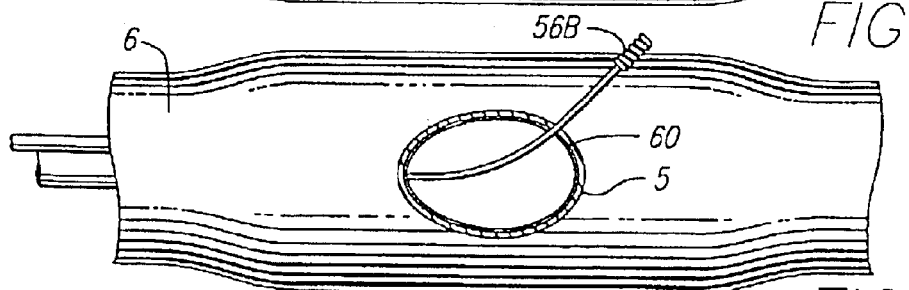
FIG. 19F
PRIOR ART

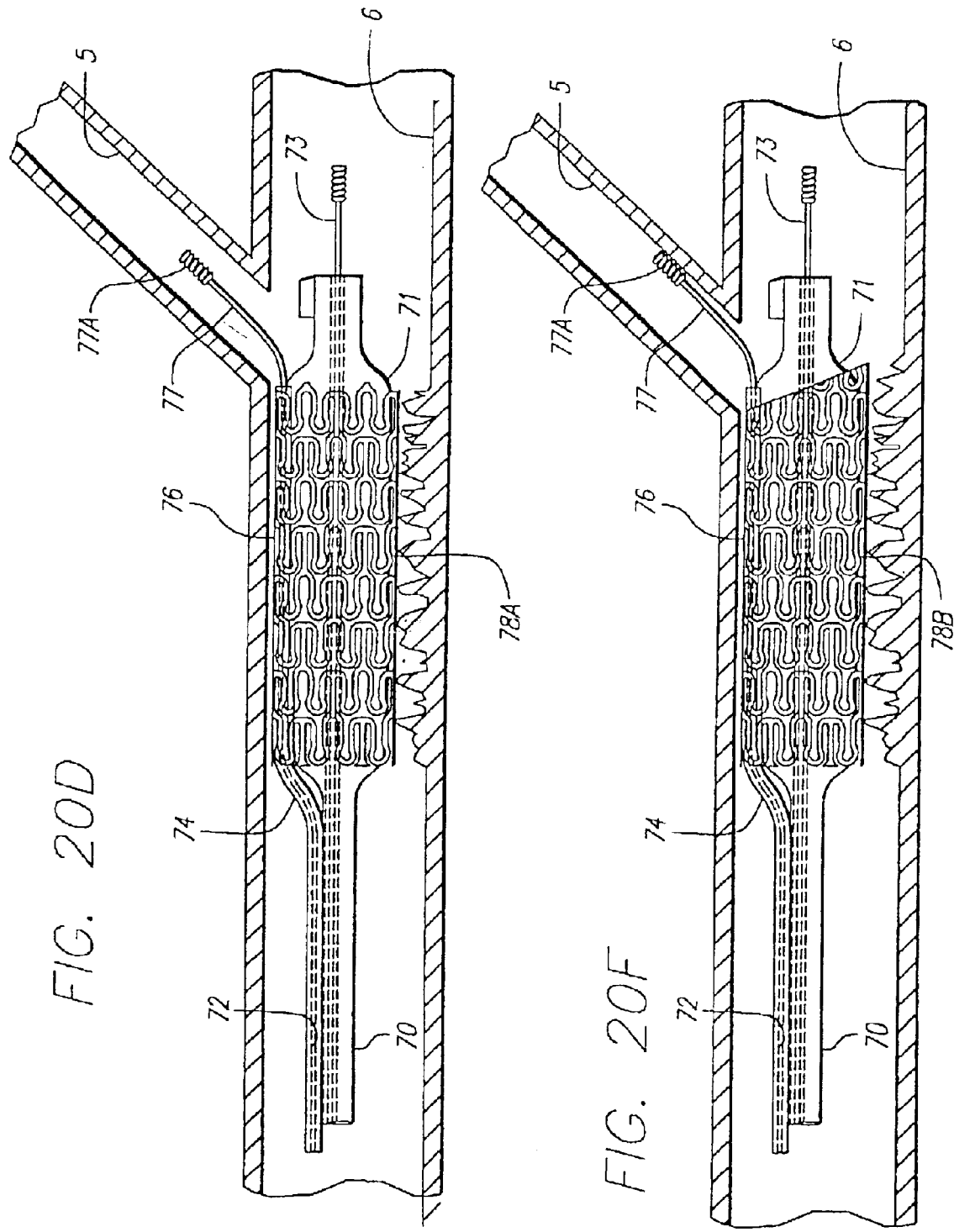

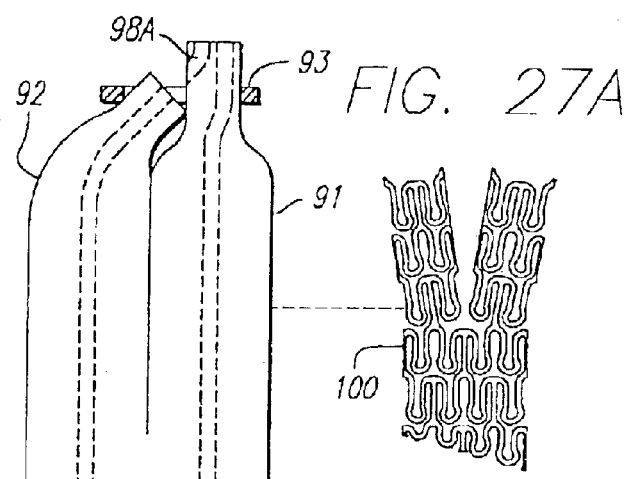
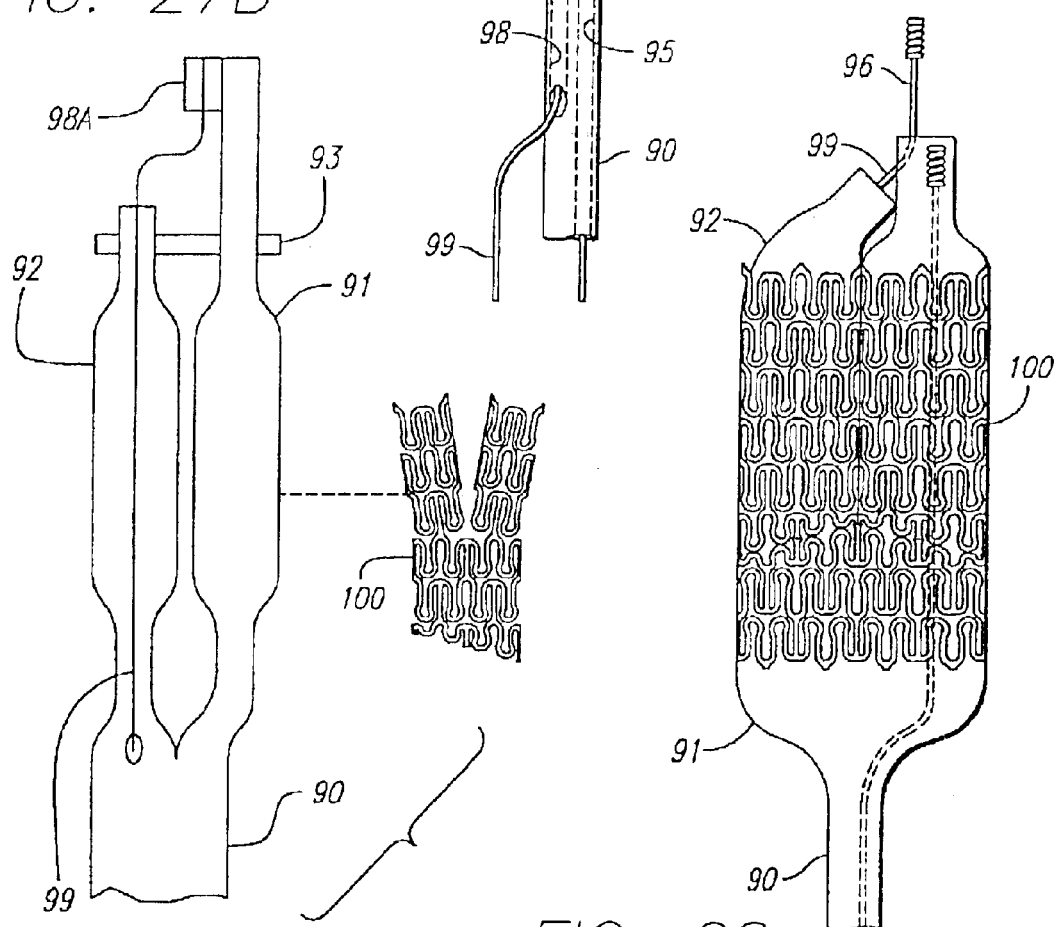
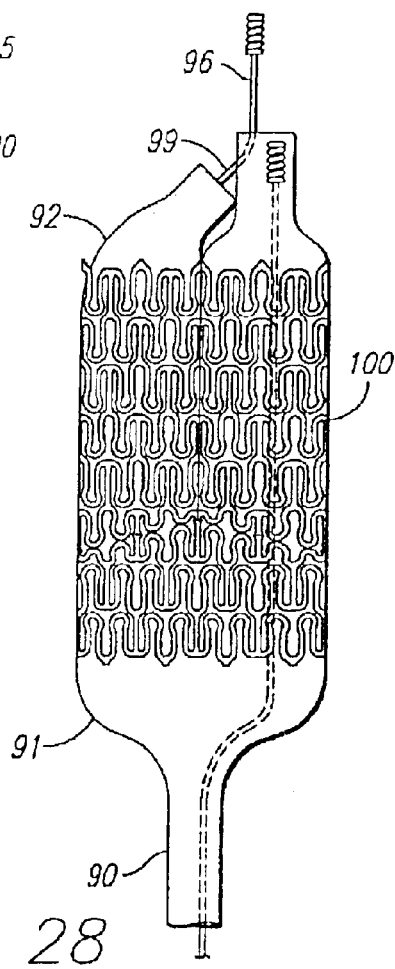

STENT AND CATHETER ASSEMBLY AND METHOD FOR TREATING BIFURCATIONS

This application is a continuation of U.S. Ser. No. 09/882,989 filed Jun. 14, 2001, now U.S. Pat. No. 6,579,312 which is a continuation application of U.S. Ser. No. 09/412,113 filed Oct. 5, 1999 now U.S. Pat. No. 6,264,682, which is a continuation of U.S. Ser. No. 08/910,857 filed Aug. 13, 1997 now U.S. Pat. No. 6,165,195.

BACKGROUND OF THE INVENTION

1. Field of the Invention

The invention relates to stent deployment assemblies for use at a bifurcation and, more particularly, a catheter assembly for implanting one or more stents for repairing bifurcations, the aorto-ostium, and bifurcated blood vessels that are diseased, and a method and apparatus for delivery and implantation.

2. Prior Art

Stents conventionally repair blood vessels that are diseased and are generally hollow and cylindrical in shape and have terminal ends that are generally perpendicular to its longitudinal axis. In use, the conventional stent is positioned at the diseased area of a vessel and, after placement, the stent provides an unobstructed pathway for blood flow.

Repair of vessels that are diseased at a bifurcation is particularly challenging since the stent must overlay the entire diseased area at the bifurcation, yet not itself compromise blood flow. Therefore, the stent must, without compromising blood flow, overlay the entire circumference of the ostium to a diseased portion and extend to a point within and beyond the diseased portion. Where the stent does not overlay the entire circumference of the ostium to the diseased portion, the stent fails to completely repair the bifurcated vessel. Where the stent overlays the entire circumference of the ostium to the diseased portion, yet extends into the junction comprising the bifurcation, the diseased area is repaired, but blood flow may be compromised in other portions of the bifurcation. Unapposed stent elements may promote lumen compromise during neointimalization and healing, producing restenosis and requiring further procedures. Moreover, by extending into the junction comprising the bifurcation, the stent may block access to portions of the bifurcated vessel that require performance of further interventional procedures. Similar problems are encountered when vessels are diseased at their angled origin from the aorta as in the ostium of a right coronary or a vein graft. In this circumstance, a stent overlying the entire circumference of the ostium extends back into the aorta, creating problems, including those for repeat catheter access to the vessel involved in further interventional procedures.

Conventional stents are designed to repair areas of blood vessels that are removed from bifurcations and, since a conventional stent generally terminates at right angles to its longitudinal axis, the use of conventional stents in the region of a vessel bifurcation may result in blocking blood flow of a side branch or fail to repair the bifurcation to the fullest extent necessary. The conventional stent might be placed so that a portion of the stent extends into the pathway of blood flow to a side branch of the bifurcation or extend so far as to completely cover the path of blood flow in a side branch. The conventional stent might alternatively be placed proximal to, but not entirely overlaying the circumference of the ostium to the diseased portion. Such a position of the conventional stent results in a bifurcation that is not completely repaired. The only conceivable situation that the conventional stent, having right-angled terminal ends, could be placed where the entire circumference of the ostium is repaired without compromising blood flow, is where the bifurcation is formed of right angles. In such scenarios, extremely precise positioning of the conventional stent is required. This extremely precise positioning of the conventional stent may result with the right-angled terminal ends of the conventional stent overlying the entire circumference of the ostium to the diseased portion without extending into a side branch, thereby completely repairing the right-angled bifurcation.

To circumvent or overcome the problems and limitations associated with conventional stents in the context of repairing diseased bifurcated vessels, a stent that consistently overlays the entire circumference of the ostium to a diseased portion, yet does not extend into the junction comprising the bifurcation, may be employed. Such a stent would have the advantage of completely repairing the vessel at the bifurcation without obstructing blood flow in other portions of the bifurcation. In addition, such a stent would allow access to all portions of the bifurcated vessel should further interventional treatment be necessary. In a situation involving disease in the origin of an angulated aorto-ostial vessel, such a stent would have the advantage of completely repairing the vessel origin without protruding into the aorta or complicating repeat access.

In addition to the problems encountered by using the prior art stents to treat bifurcations, the delivery platform for implanting such stents has presented numerous problems. For example, a conventional stent is implanted in the main vessel so that a portion of the stent is across the side branch, so that stenting of the side branch must occur through the main-vessel stent struts. In this method, commonly referred to in the art as the "monoclonal antibody" approach, the main-vessel stent struts must be spread apart to form an opening to the side-branch vessel and then a catheter with a stent is delivered through the opening. The cell to be spread apart must be randomly and blindly selected by recrossing the deployed stent with a wire. The drawback with this approach is there is no way to determine or guarantee that the main-vessel stent struts are properly oriented with respect to the side branch or that the appropriate cell has been selected by the wire for dilatation. The aperture created often does not provide a clear opening and creates a major distortion in the surrounding stent struts. The drawback with this approach is that there is no way to tell if the main-vessel stent struts have been properly oriented and spread apart to provide a clear opening for stenting the side-branch vessel.

In another prior art method for treating bifurcated vessels, commonly referred to as the "Culotte technique," the side-branch vessel is first stented so that the stent protrudes into the main vessel. A dilatation is then performed in the main vessel to open and stretch the stent struts extending across the lumen from the side-branch vessel. Thereafter, the main-vessel stent is implanted so that its proximal end overlaps with the side-branch vessel. One of the drawbacks of this approach is that the orientation of the stent elements protruding from the side-branch vessel into the main vessel is completely random. Furthermore the deployed stent must be recrossed with a wire blindly and arbitrarily selecting a particular stent cell. When dilating the main vessel stretching the stent struts is therefore random, leaving the possibility of restricted access, incomplete lumen dilatation, and major stent-distortion.

In another prior art device and method of implanting stents, a "T" stent procedure includes implanting a stent in the side-branch ostium of the bifurcation followed by stenting the main vessel across the side-branch ostium. In another prior art procedure, known as "kissing" stents, a stent is implanted in the main vessel with a side-branch stent partially extending into the main vessel creating a double-barrelled lumen of the two stents in the main vessel distal to the bifurcation. Another prior art approach includes a so-called "trouser legs and seat" approach, which includes implanting three stents, one stent in the side-branch vessel, a second stent in a distal portion of the main vessel, and a third stent, or a proximal stent, in the main vessel just proximal to the bifurcation.

All of the foregoing stent deployment assemblies suffer from the same problems and limitations. Typically, there is uncovered intimal surface segments on the main vessel and side-branch vessels between the stented segments. An uncovered flap or fold in the intima or plaque will invite a "snowplow" effect, representing a substantial risk for subacute thrombosis, and the increased risk of the development of restenosis. Further, where portions of the stent are left unapposed within the lumen, the risk for subacute thrombosis or the development of restenosis again is increased. The prior art stents and delivery assemblies for treating bifurcations are difficult to use, making successful placement nearly impossible. Further, even where placement has been successful, the side-branch vessel can be "jailed" or covered so that there is impaired access to the stented area for subsequent intervention. The present invention solves these and other problems as will be shown.

In addition to problems encountered in treating disease involving bifurcations for vessel origins, difficulty is also encountered in treating disease confined to a vessel segment but extending very close to a distal branch point or bifurcation which is not diseased and does not require treatment. In such circumstances, very precise placement of a stent covering the distal segment, but not extending into the ostium of the distal side-branch, may be difficult or impossible. The present invention also offers a solution to this problem.

References to distal and proximal herein shall mean: the proximal direction is moving away from or out of the patient and distal is moving toward or into the patient. These definitions will apply with reference to body lumens and apparatus, such as catheters, guide wires, and stents.

SUMMARY OF THE INVENTION

The invention provides for improved stent designs and stent delivery assemblies for repairing a main vessel and side-branch vessel forming a bifurcation, without compromising blood flow in other portions of the bifurcation, thereby allowing access to all portions of the bifurcated vessels should further interventional treatment be necessary. In addition, it provides an improved stent design and stent delivery system for repairing disease confined to the aorto-ostium of a vessel without protrusion into the aorta. The stent delivery assemblies of the invention all share the novel feature of containing, in addition to a tracking guide wire, a second positioning wire which affects rotation and precise positioning of the assembly for deployment of the stent.

The present invention includes a proximal angled stent for implanting in a side-branch vessel adjacent to a bifurcation. The cylindrical member can have substantially any outer wall surface typical of conventional stents used, for example, in the coronary arteries. The cylindrical member of the proximal angled stent has a distal end forming a first plane section that is substantially transverse to the longitudinal axis of the stent. The proximal end of the stent forms a second plane section that is at an angle, preferably an acute angle, relative to the longitudinal axis of the stent. The acute angle is selected to approximately coincide with the angle formed by the intersection of the side-branch vessel and the main vessel so that no portion of the stented area in the side-branch vessel is left uncovered, and no portion of the proximal angled stent extends into the main vessel.

A second stent is provided for implanting in the main vessel adjacent to a bifurcation in which a cylindrical member has distal and proximal ends and an outer wall surface therebetween, which can typically be similar to the outer wall surface of stents used in the coronary arteries. An aperture is formed in the outer wall surface of the apertured stent and is sized and positioned on the outer wall surface so that when the apertured stent is implanted in the main vessel, the aperture is aligned with the side-branch vessel and the proximal angled stent in the side-branch vessel, providing unrestricted blood flow from the main vessel through to the side-branch vessel. Deployment of the angled and apertured stents is accomplished by a novel stent delivery system adapted specifically for treating bifurcated vessels.

In one embodiment for implanting the proximal angled stent, a side-branch catheter is provided in which a tracking guide wire lumen extends within at least a portion of the side-branch catheter, being designed to be either an over-the-wire or rapid exchange-type catheter. An expandable member is disposed at the distal end of the side-branch catheter. A tracking guide wire is provided for slidable movement within the tracking guide wire lumen. A positioning guide wire lumen is associated with the catheter and the expandable member, such that a portion of the positioning guide wire lumen is on the outer surface of the catheter and it approaches the proximal end of the outer surface of the expandable member. A stent-positioning guide wire is provided for slidable movement within the positioning lumen. The proximal ends of the tracking and stent-positioning guide wires extend out of the patient and can be simultaneously manipulated so that the distal end of the stent-positioning guide wire is advanced in the main vessel distal to a side-branch vessel, and the distal end of the tracking guide wire is advanced into the side-branch vessel distal to the target area. In a preferred embodiment, the stent-positioning guide wire lumen includes an angulated section so that the stent-positioning guide wire advanced in the main vessel distal to the side-branch vessel results in rotation causing the proximal angled stent to assume the correct position in the side-branch vessel. The positioning lumen functions to orient the stent-positioning guide wire to rotate or torque the side-branch catheter to properly align and position the proximal angled stent in the side-branch vessel.

The side-branch catheter assembly is capable of delivering the proximal angled stent, mounted on the expandable member, in the side-branch vessel. The side-branch catheter could also be configured for delivering a self-expanding proximal angled stent.

The stent delivery system of the present invention further includes a main-vessel catheter for delivering a stent in the main vessel after the side-branch vessel has been stented. The main-vessel catheter includes a tracking guide wire lumen extending through at least a portion thereof, and adapted for receiving a tracking guide wire for slidable movement therein. An expandable member is positioned near the main-vessel catheter distal end for delivering and implanting a main-vessel (apertured) stent in the main vessel. The main-vessel stent includes an aperture on its outer surface which aligns with the side-branch vessel. A positioning guide wire lumen is associated with the expandable member, and is sized for slidably receiving the stent-positioning guide wire. The stent-positioning guide wire slides within the positioning guide wire lumen to orient the expandable member so that it is positioned adjacent to, but not in, the side-branch vessel with the stent aperture facing the side-branch ostium.

In a preferred embodiment, both the side-branch catheter and main-vessel catheter assemblies include the so-called rapid exchange catheter features which are easily exchangeable for other catheters while the tracking and positioning guide wires remain positioned in the side-branch vessel and the main vessel, respectively. In an alternate embodiment, both catheters may be of the "over-the-wire" type.

The present invention further includes a method for delivering the proximal angled and the main-vessel (apertured) stents in the bifurcated vessel. In a preferred embodiment of the side-branch catheter system (side-branch catheter plus proximal angled stent), the distal end of the tracking guide wire is advanced into the side-branch vessel and distal to the target area. The side-branch catheter is then advanced along the tracking guide wire until the distal end of the catheter is just proximal of entering the side-branch. The distal end of the integrated, stent-positioning guide wire is then advanced by the physician pushing the guide wire from outside the body. The distal end of the stent-positioning wire travels through the positioning guide wire lumen and passes close to the proximal end of the proximal angled stent and expandable member and exits the lumen. The wire is advanced in the main vessel until the distal end is distal to the side-branch vessel. The catheter is then advanced into the side branch until resistance is felt from the stent-positioning guide wire pushing up against the ostium of the side-branch vessel causing the proximal angled stent to rotate into position and arresting its advancement at the ostium. Thereafter, the proximal angled stent, mounted on the expandable member, is aligned across the target area and the angled proximal end of the stent is aligned at the intersection of the side-branch vessel and the main vessel (the ostium of the side-branch vessel) so that the stent completely covers the target area in the side-branch vessel, yet does not extend into the main vessel, thereby blocking blood flow. The expandable member is expanded thereby expanding and implanting the proximal angled stent in the sidebranch vessel. The positioning wire prevents forward movement of the expandable member and proximal angled stent during inflation. Thereafter, the expandable member is deflated and the side-branch catheter assembly is withdrawn from the patient in a known rapid-exchange manner. In this embodiment, the side-branch catheter is designed so that both the side-branch tracking guide wire and main-vessel positioning guide wire can be left in their respective vessels should sequential or simultaneous high pressure balloon inflation be required in each of the vessels in order to complete the stenting procedure. In other words, the integrated positioning wire can be unzipped from the proximal 100 cm of the catheter thereby allowing it to act as a rapid exchange wire. Preferably, high pressure balloons are inflated simultaneously in the main vessel and proximal angled stents in order to avoid deforming one stent by unopposed balloon inflation within the other one. This additional step of high pressure balloon inflation is a matter of physician choice. A further advantage of this embodiment is that by waiting to advance the integrated stent-positioning wire out of catheter only when the catheter distal end is near the target area, wire wrapping, encountered in an embodiment utilizing two non-integrated guide wires, is avoided.

Utilizing this preferred method, the side-branch vessel can be stented without the need for stenting the main vessel.

In an aorto-ostial application of the side-branch catheter assembly (side-branch catheter plus proximal angulated stent), the positioning wire is advanced into the aortic root while the tracking wire is advanced into the right coronary or vein graft whose angulated origin is to be stented. After advancement of the proximal-angled stent, mounted on the expanding member, it is aligned across the target area and the angled proximal end of the stent is aligned at the ostium.

In the event that the main vessel is to be stented (with the stent placed across the bifurcation site), the proximal end of the main-vessel guide wire is inserted into the distal end of the guide wire lumen of the main-vessel catheter. The side-branch wire would be removed from the side branch at this time. The main-vessel catheter would then be advanced into the body until the catheter is within one cm or so of the target site. The distal end of the second (integrated, stent-positioning) guide wire, which resides in the main-vessel catheter during delivery to the main vessel, is then advanced by having the physician push the positioning wire from outside the body. The distal end of the stent-positioning wire travels through the positioning guide wire lumen and passes underneath the proximal half of the stent until it exits at the site of the stent aperture or a designated stent cell where an aperture can be formed. The catheter is then advanced distally until resistance is felt from the stent-positioning guide wire pushing up against the ostium of the side-branch vessel indicating that the stent aperture is correctly facing the side-branch vessel ostium and is aligned with the proximal end of the proximal angled stent. Thereafter, the expandable member on the main-vessel catheter is inflated, thereby expanding and implanting the main-vessel stent into contact with the main vessel, with the aperture in the stent providing a flow path,for the blood from the main vessel through to the side-branch vessel without any obstructions. The expandable member is deflated and the main-vessel catheter is removed from the body. The main-vessel catheter is designed so that both the main-vessel guide wire and side-branch wire can be left in their respective vessels should sequential or simultaneous high pressure balloon inflation be required in each of the vessels in order to complete the stenting procedure. The presence of the stent-positioning wire in the stent aperture permits catheter access through this aperture into the side-branch vessel for balloon inflation to smooth out the aperture in the main-vessel stent. This additional step is a matter of physician choice.

Utilizing this preferred method, the main vessel can be stented without the need for stenting the side-branch vessel. An advantage of this embodiment is that a major side branch, not diseased and requiring treatment, exiting from a main vessel requiring stenting, may be protected by the positioning wire while the main vessel is stented. If "snow-plowing" compromise or closure of the side-branch vessel occurs with main-vessel stenting, then access is already present and guaranteed for stenting of the side-branch vessel over the wire already in place in the manner described above. This will allow confident stenting of a main vessel segment containing a major side branch. In this usage, only if compromise or occlusion of the side branch occurs, will additional stenting of the side branch be required.

In an alternative embodiment, a main-vessel stent that does not have an aperture on its outer surface is mounted on the main-vessel catheter and is implanted in the main vessel so that it spans the opening to the side-branch vessel. Thereafter, a balloon catheter is inserted through a targeted (non-random) stent cell of the main-vessel stent, which is centered precisely facing the side-branch ostium, so that the balloon partially extends into the side-branch vessel. This balloon has tracked over the positioning wire which has been left in place through the targeted stent cell during and after deployment of the main vessel stent. The balloon is expanded, forming an opening through the stent struts that corresponds to the opening of the side-branch vessel, providing a blood-flow path through the main vessel and main-vessel stent and into the side-branch vessel. A proximal angled stent mounted on a side-branch catheter is then advanced through the main-vessel stent and the opening formed in the targeted stent cell through to the side-branch vessel. The proximal angled stent is expanded and implanted in the side-branch vessel so that all portions of the side-branch vessel are covered by the stent in the area of the bifurcation. After the main-vessel stent and the side-branch vessel proximal angled stent are implanted, an uncompromised blood-flow path is formed from the main vessel through the main-vessel stent and opening into the side-branch vessel, and through the side-branch vessel proximal angled stent.

In another alternative embodiment, a stent having a distal angle is implanted in the main vessel. In portions of the main vessel having disease that approaches and is directly adjacent to the side-branch vessel, a distal angle stent is implanted using the novel catheter of the present invention so that the stent covers the diseased area, but does not jail or cover the opening to the side-branch vessel.

In another alternative embodiment, a Y-shaped catheter and Y-shaped stent are provided for stenting a bifurcated vessel. In this embodiment, a dual balloon catheter has a Y-shaped stent mounted on the balloons and the balloons are positioned side by side for easier delivery. The balloons are normally biased apart, but are restrained and held together to provide a low profile during delivery of the stent. A guide wire is first positioned in a main vessel at a point distal to the bifurcation. A second guide wire is retained in the catheter in a second guide wire lumen while the catheter is advanced over the tracking guide wire so that the balloons and stent are distal to the bifurcation. The tracking guide wire is then withdrawn proximally thereby releasing the balloons which spring apart. The catheter is withdrawn proximally until it is proximal to the bifurcation. As the catheter is withdrawn proximally, one of the two guide wires is left in the main vessel. The other guide wire is then advanced into the side-branch vessel. The catheter is then advanced over both guide wires until the balloons and stent are anchored in the bifurcation. The balloons are inflated and the stent expanded and implanted in the bifurcation.

In another embodiment two apertured stents are implanted to cover the bifurcated vessels. A main-vessel stent has a cylindrical shape having a heavy cell density on the distal half and light cell density on the proximal half, and an aperture on its outer surface at the junction at these two halves. A main-vessel stent is first implanted in the main vessel so that its aperture aligns with the ostium of the side-branch vessel, thereby covering the main vessel proximally with light cell density and distally with heavy cell density. A second main-vessel stent is then implanted over a tracking wire into the side branch so that the heavy cell density portion of the stent is implanted in the side-branch vessel, the light cell density is implanted in the main vessel and overlaps the light cell density of the proximal end of the main-vessel stent, and the aperture faces the main vessel as it departs from the side branch. Combined densities of proximal light cell portions proximal to the bifurcation are similar to the heavy cell densities in each limb distal to the bifurcation. Respective apertures of each of the two main-vessel stents are aligned with the respective ostia of both limbs of the bifurcation (main vessel and side branch).

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 7A is an elevational view, partially in section, of a side-branch catheter assembly depicting the distal end of the catheter with the expandable member and the second guide wire lumen attached thereto, for receiving the integrated stent-positioning guide wire, while the tracking guide wire is received by the main guide wire lumen.

FIG. 7B is an elevational view, partially in section, of the catheter assembly of FIG. 7A, in which the stent positioning guide wire is advanced out of the catheter.

FIG. 8 is an elevational view, partially in section, of a side-branch catheter assembly depicting an expandable balloon having an angled proximal portion corresponding to the angle of the proximal angled stent.

FIG. 9A is an elevational view of a bifurcated vessel in which a side-branch tracking guide wire has been advanced into a side-branch vessel, with the stent-positioning guide wire remaining within the catheter until the catheter assembly is just proximal to the side-branch vessel.

FIG. 9B is an elevational view of a bifurcation in which a side-branch tracking guide wire has been advanced through the patient's vascular system into a side branch, and a stent-positioning guide wire has been advanced through the patient's vascular system and into the main vessel distal to the ostium of the side-branch vessel.

FIG. 10A is an elevational view of a bifurcation in which the side-branch catheter assembly has been advanced in the patient's vasculature so that the proximal angled stent mounted on the expandable member is positioned in the target area of the side-branch vessel.

FIGS. 11A–11D are partial elevational views in which the side-branch catheter assembly of FIG. 10A is used to implant the proximal angled stent in the side-branch vessel where the proximal angled stent is rotated to be properly aligned for implanting in the vessel.

FIGS. 12A–12C depict an elevational view, partially in section, of a main-vessel catheter assembly in which the main vessel stent has an aperture on its outer surface.

FIGS. 12D–12F depict an elevational view, partially in section, of the main-vessel catheter of FIGS. 12A–12C with a ramp to help orient and advance the guide wire through the aperture in the main-vessel stent.

FIGS. 12G–12I depict an elevational view, partially in section, of an alternative embodiment of the main-vessel catheter of FIGS. 12A–12C in which the guide wire lumen is angled to pass under the stent and exit through the stent aperture.

FIGS. 13A–13E are elevational views, partially in section, depicting the main-vessel catheter assembly of FIG. 12A and the main-vessel stent in which two guide wires are used to correctly position the main vessel stent so that the aperture in the stent is aligned with the side-branch vessel.

FIGS. 16A–16D are elevational views, partially in section, of a main vessel catheter having the main vessel stent of FIG. 15 mounted thereon, and its relationship to the guide wire for advancing through a targeted stent cell.

FIGS. 19A–19C are elevational views of a bifurcation in which a main-vessel stent is first implanted in the main vessel and a catheter assembly next deploys a proximal angled stent in a side-branch vessel.

FIGS. 19D and 19E are cross-sectional views looking down the side-branch vessel at an expanded main vessel prior art stent in which a random, sub-optimal stent cell was entered and expanded.

FIG. 19F is a cross-sectional view looking down the side-branch vessel at an expanded main-vessel stent of the invention in which proper targeted stent cell was entered and expanded.

FIG. 20D is an elevational view, partially in section, depicting a main-vessel stent implanted in the main vessel without jailing or covering the side-branch vessel.

FIG. 20F is an elevational view, partially in section, of a distal angled stent being implanted in the main vessel without jailing the side-branch vessel.

FIG. 27A is an elevational view, partially in section, depicting an alternative embodiment in which a Y-shaped catheter assembly deploys a Y-shaped stent in the bifurcation.

FIG. 27B is an elevational view depicting an alternative embodiment in which a dual balloon catheter assembly deploys a Y-shaped stent in the bifurcation.

FIG. 28 is an elevational view depicting the Y-shaped catheter assembly of FIG. 27A in which the stent is mounted on the balloon portions of the catheter.

DETAILED DESCRIPTION OF THE PREFERRED EMBODIMENTS

Figure 1:
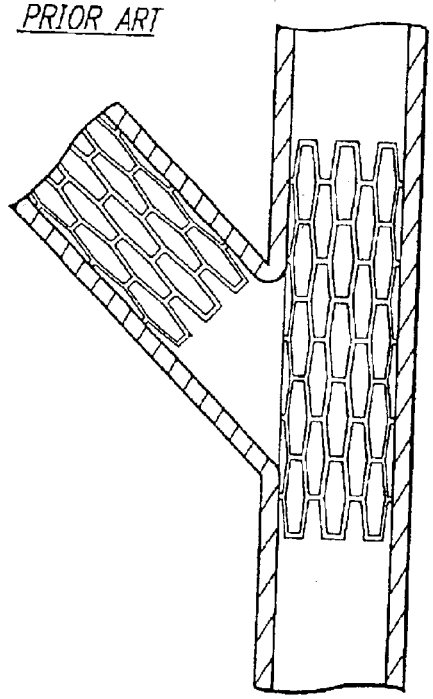
FIG. 1 is an elevational view of a bifurcation in which a prior art "T" stent is in a side-branch ostium followed by the stenting of the main vessel across the branch ostium.

The present invention includes an assembly and method for treating bifurcations in, for example, the coronary arteries, veins, arteries, and other vessels in the body. Prior art attempts at implanting intravascular stents in a bifurcation have proved less than satisfactory. For example, FIGS. 1–4 depict prior art devices which include multiple stents being implanted in both the main vessel and a side-branch vessel. In FIG. 1, a prior art "T" stent is implanted such that a first stent is implanted in the side branch near the ostium of the bifurcation, and a second stent is implanted in the main vessel, across the side-branch ostium. With this approach, portions of the side-branch vessel are left uncovered, and blood flow to the side-branch vessel must necessarily pass through the main-vessel stent, causing possible obstructions or thrombosis.

Figure 2:
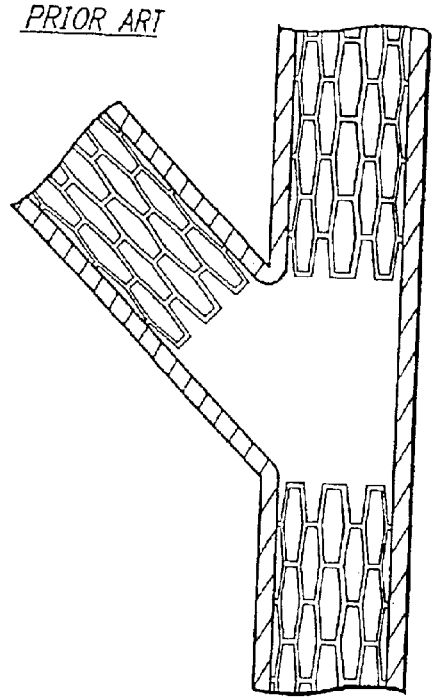
FIG. 2 is an elevational view of a bifurcation in which "touching" prior art stents are depicted in which one stent is implanted in the side branch, a second stent implanted in a proximal portion of the main vessel next to the branch stent, with interrupted placement of a third stent implanted more distally in the main vessel.
Figure 3:
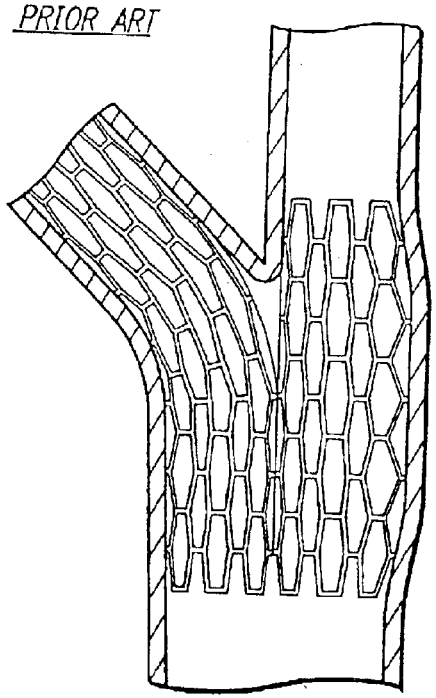
FIG. 3 is an elevational view of a bifurcation depicting "kissing" stents where a portion of one stent is implanted in both the side-branch and the main vessel and adjacent to a second stent implanted in the main vessel creating a double-barreled lumen in the main vessel distal to the bifurcation.
Figure 4:
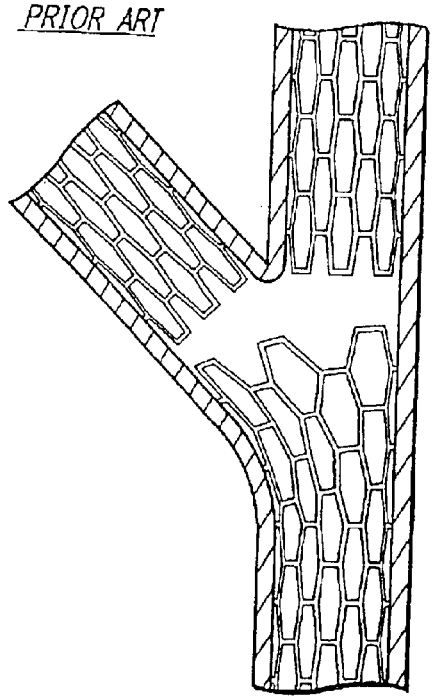
FIG. 4 is an elevational view of a prior art "trouser legs and seat" stenting approach depicting one stent implanted in the side-branch vessel, a second stent implanted in a proximal portion of the main vessel, and a close deployment of a third stent distal to the bifurcation leaving a small gap between the three stents of an uncovered luminal area.

Referring to FIG. 2, three prior art stents are required to stent the bifurcation. In FIG. 3, the prior art method includes implanting two stents side by side, such that one stent extends into the side-branch vessel and the main vessel, and the second stent is implanted in the main vessel. This results in a double-barreled lumen which can present problems such as thrombosis, and turbulence in blood flow. Referring to the FIG. 4 prior art device, a first stent is implanted in the side-branch vessel, a second stent is implanted in a proximal portion of the main vessel, and a third stent is implanted distal to the bifurcation, thereby leaving a small gap between the stents and an uncovered luminal area.

All of the prior art devices depicted in FIGS. 1–4 have various drawbacks which have been solved by the present invention.

Figure 5A:
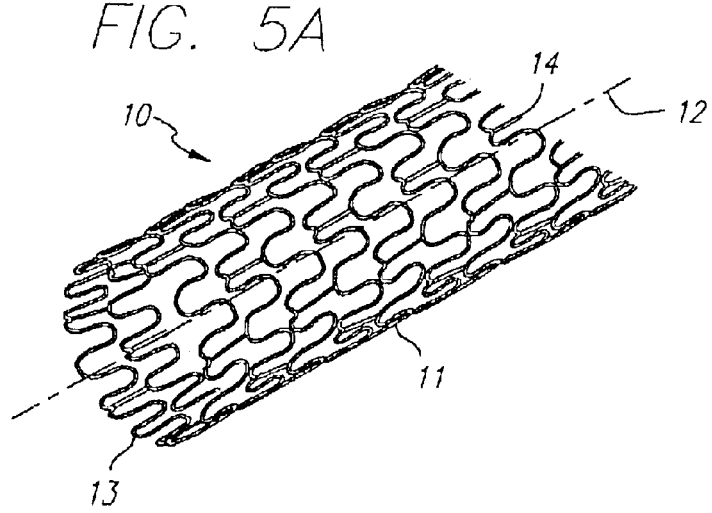
FIG. 5A is a perspective view of a stent of the present invention having an angled proximal end.
Figure 5B:
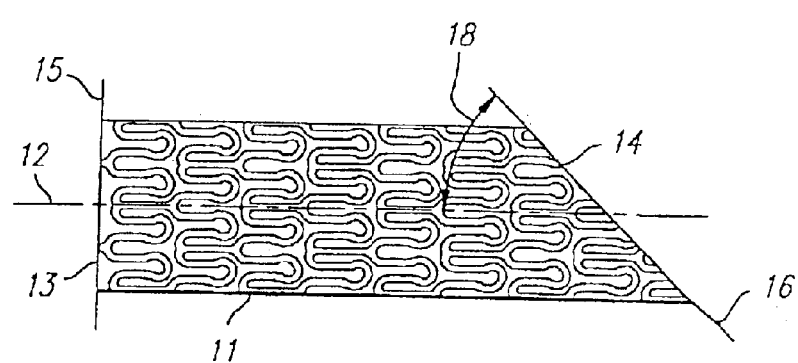
FIG. 5B is a side elevational view of the proximal angled stent of FIG. 5A depicting the distal end being transverse to the longitudinal axis of the stent, and the proximal end at an angle of less than 90°.
Figure 5C:
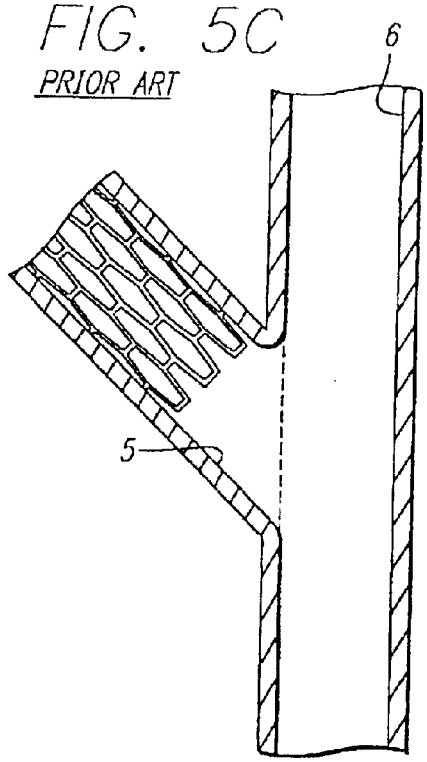
FIG. 5C is an elevational view of a bifurcation in which a prior art stent is implanted in the side-branch vessel.
Figure 5D:
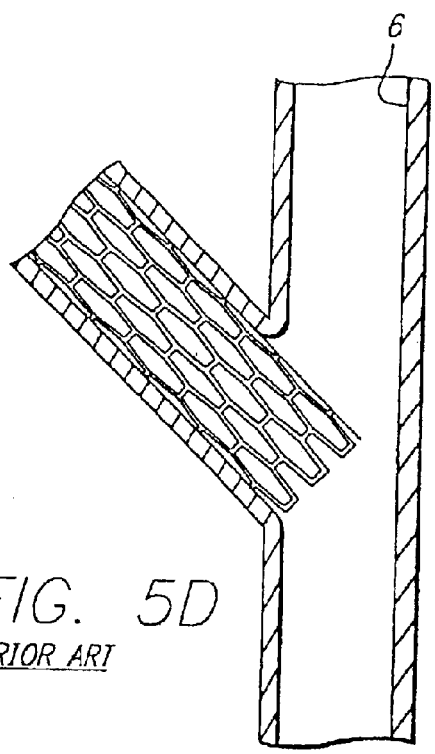
FIG. 5D is an elevational view of a bifurcation in which a prior art stent is implanted in the side-branch vessel, with the proximal end of the stent extending into the main vessel.
Figure 5E:
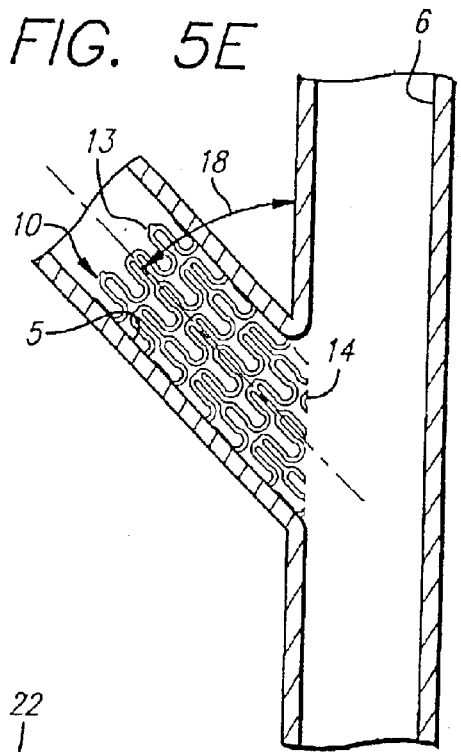
FIG. 5E is an elevational view of a bifurcation in which the proximal angled stent of the present invention, as depicted in FIGS. 5A and 5B, is implanted in the side-branch vessel.

In one preferred embodiment of the present invention, as depicted in FIGS. 5A, 5B and 5E, proximal angled stent 10 is configured for deployment in side-branch vessel 5. Proximal angled stent 10 includes a cylindrical member 11 having longitudinal axis 12 which is an imaginary axis extending through cylindrical member 11. Distal end 13 and proximal end 14 define the length of cylindrical member 11. First plane section 15 is defined by a plane section through distal end 13 of the cylindrical member, and second plane section 16 is defined by a plane section through proximal end 14 of the cylindrical member. Second plane section 16 defines acute angle 18, which is the angle between second plane section 16 and longitudinal axis 12.

In treating side-branch vessel 5, if a prior art stent is used in which there is no acute angle at one end of the stent to match the angle of the bifurcation, a condition as depicted in FIGS. 5C and 5D will occur. That is, a stent deployed in side-branch vessel 5 will leave a portion of the side-branch vessel exposed, or as depicted in 5D, a portion of the stent will extend into main-vessel 6. As depicted in FIG. 5E, proximal angled stent 10 of the present invention has an acute angle 18 that approximates the angle formed by the bifurcation 4 of side-branch vessel 5 and main-vessel 6. Thus, acute angle 18 is intended to approximate the angle formed by the intersection of side-branch 5 and main-vessel 6. The angle between side-branch vessel 5 and main-vessel 6 will vary for each application, and for purposes of the present invention, should be less than 90°. If there is a 90° angle between the side-branch vessel and the main vessel, a conventional stent having ends that are transverse to the stent longitudinal axis, would be suitable for stenting the side-branch vessel.

The proximal angled stent can be implanted in the side-branch vessel to treat a number of angulated ostial lesions including, but not limited to, the following:

1. The ostium of a left anterior descending artery (LAD) where there is a circumflex or trifurcation vessel at less than 90° in its departure from the LAD.
2. The ostium of the circumflex artery or a trifurcation in a similar situation as number 1.
3. The ostium of a sizeable diagonal.
4. The LAD just distal to, but sparing, the origin of a diagonal.
5. The ostium of a circumflex marginal artery with an angulated take-off.
6. Disease in the circumflex artery just distal to a marginal take-off, but sparing that take-off.
7. The aorta-ostium of a right coronary artery with an angled take-off.
8. The origin of an angulated posterior descending artery.
9. The origin of an LV extension branch just at and beyond the crux, sparing the posterior descending artery.
10. The ostium of an angulated vein graft origin.
11. Any of many of the above locations in conjunction with involvement of the bifurcation and an alternate vessel.

The proximal angled stent of the present invention typically can be used as a solo device to treat the foregoing indications, or it can be used in conjunction with the main vessel stent described herein for stenting the bifurcation.

Figure 6A:
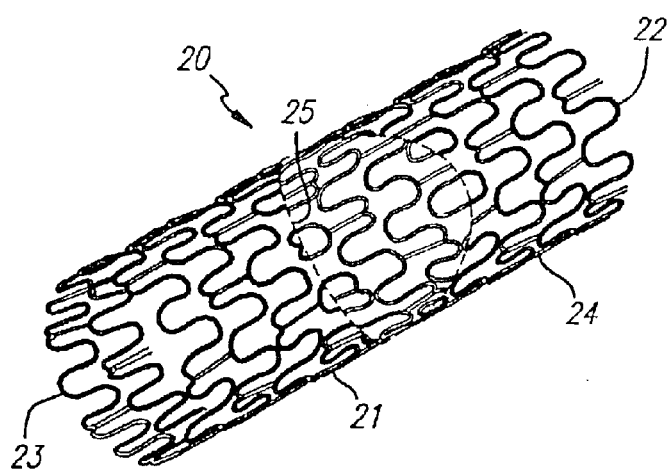
FIG. 6A is a perspective view depicting the main-vessel stent of the present invention in which an aperture is formed on the outer surface of at least a portion of the stent.
Figure 6B:
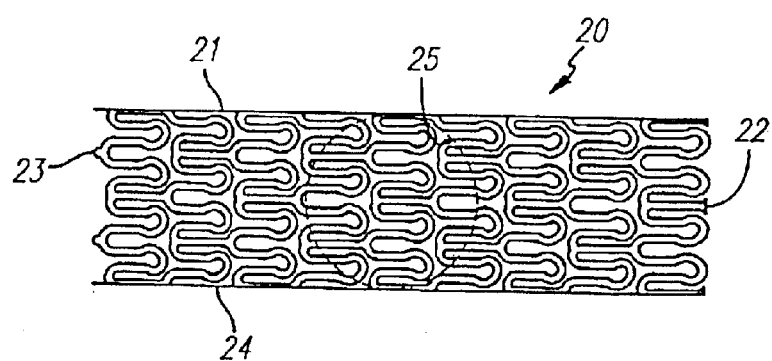
FIG. 6B is a side elevational view of the main-vessel stent of FIG. 6A.
Figure 10B:
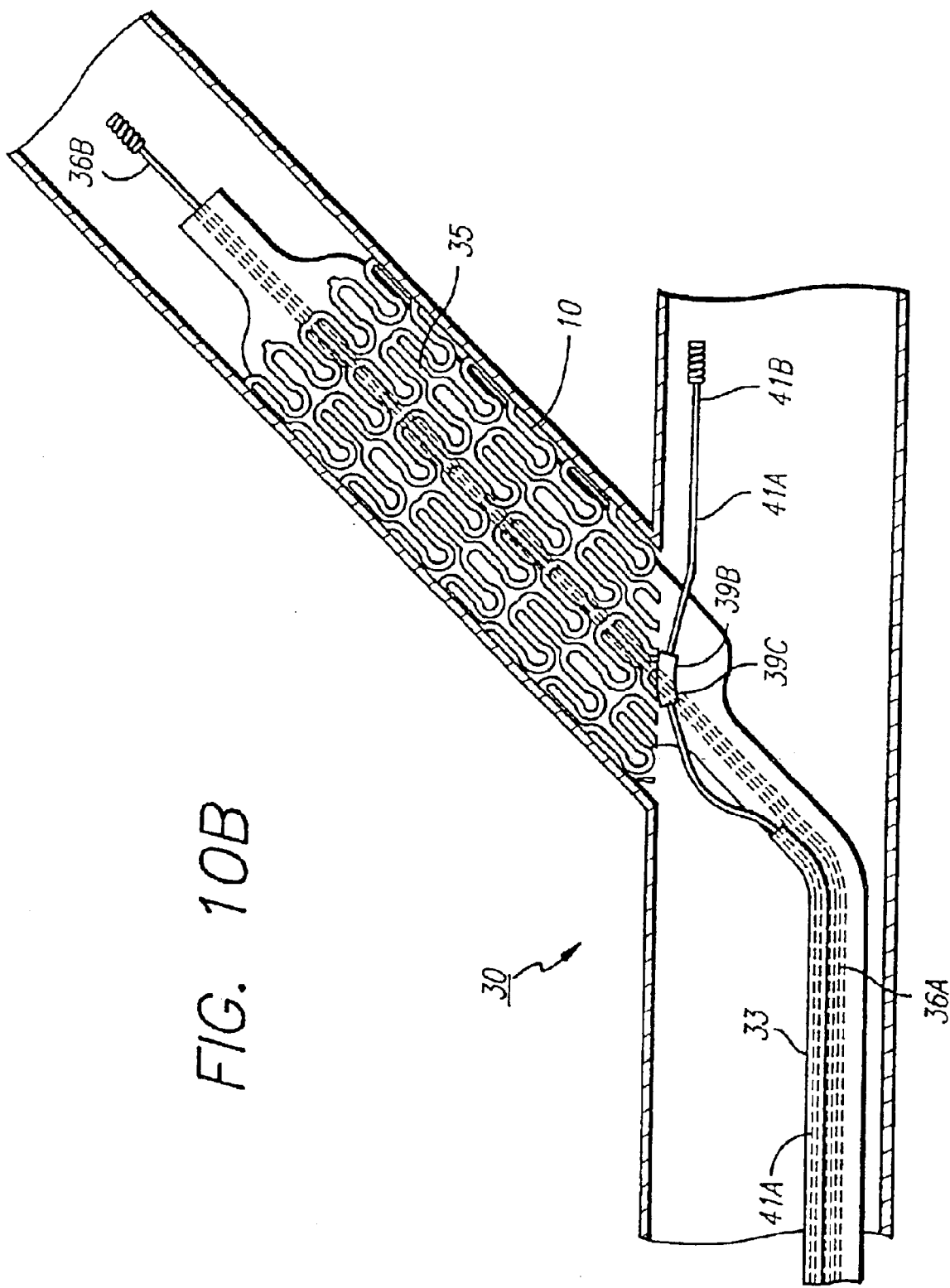
FIG. 10B is an elevational view of the side-branch catheter assembly of FIG. 10A in which the proximal angled stent has been expanded by the balloon portion of the catheter in the side-branch vessel.
Figure 11D:
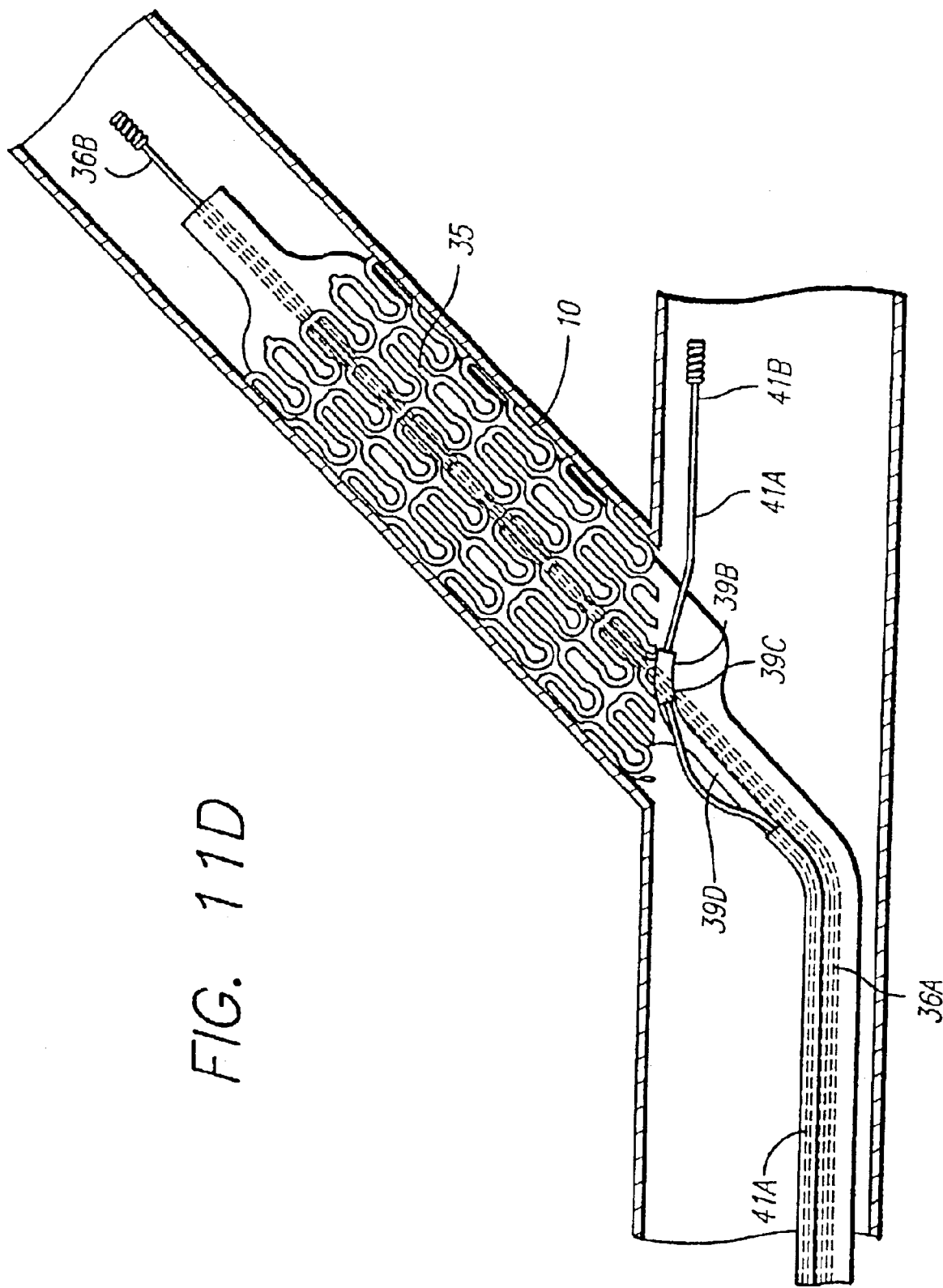

In keeping with the invention, as depicted in FIGS. 6A and 6B, main-vessel stent 20 is configured for deployment in main-vessel 6. Main-vessel stent 20 includes cylindrical member 21 having distal end 22 and proximal end 23. Main-vessel stent 20 includes outer wall surface 24 which extends between distal end 22 and proximal end 23 and incorporates aperture 25 on outer wall surface 24. Aperture 25 is configured so that, upon expansion, it approximates the diameter of expanded proximal end 14 of proximal angled stent 10. When main-vessel stent 20 is implanted and expanded into contact with main-vessel 6, aperture 25 is aligned with side-branch vessel 5 and proximal end 14 of proximal angled stent, thereby providing an unrestricted blood flow path from the side-branch vessel to the main vessel. Unlike the prior art, the main-vessel catheter allows selection and positioning of an aperture at the side-branch ostium. Furthermore, it provides for the positioning of a guide wire during main-vessel stent deployment which can be used for-additional intervention if necessary. In the prior art techniques access to a side-branch is through a randomly selected stent element ("cell") and is only possible after deployment of the stent. The precise positioning of aperture 25 is optional and aperture 25 could be positioned either closer to the proximal or distal end of stent 20.

Proximal angled stent 10 and main-vessel stent 20 can be formed from any of a number of materials including, but not limited to, stainless steel alloys, nickel-titanium alloys (the NiTi can be either shape memory or pseudoelastic), tantalum, tungsten, or any number of polymer materials. Such materials of manufacture are known in the art. Further, proximal angled stent 10 and main-vessel stent 20 can have virtually any pattern known to prior art stents. In a preferred configuration, proximal angled stent 10 and main-vessel stent 20 are formed from a stainless steel material and have a plurality of cylindrical elements connected by connecting members, wherein the cylindrical elements have an undulating or serpentine pattern. Such a stent is disclosed in U.S. Pat. No. 5,514,154 and is manufactured and sold in Europe only, at this time, by Advanced Cardiovascular Systems, Inc., Santa Clara, Calif. The stent is sold under the tradename MultiLink® Stent. Such stents can be modified to include the novel features of proximal angled stent 10 (the angulation) and main-vessel stent 20 (the aperture).

Proximal angled stent 10 and main-vessel stent 20 preferably are balloon-expandable stents that are mounted on a balloon portion of a catheter and crimped tightly onto the balloon to provide a low profile delivery diameter. After the catheter is positioned so that the stent and the balloon portion of the catheter are positioned either in the side-branch or the main vessel, the balloon is expanded, thereby expanding the stent beyond its elastic limit into contact with the vessel. Thereafter, the balloon is deflated and the balloon and catheter are withdrawn from the vessel, leaving the stent implanted. Deployment of the angled and main-vessel stents is accomplished by a novel stent delivery system adapted specifically for treating bifurcated vessels. The proximal angled stent and the main-vessel stent could be made to be either balloon expandable or self-expanding.

In one preferred embodiment for delivering the novel stents of the present invention, as depicted in FIGS. 7A and 7B, side-branch stent delivery assembly 30 is provided and includes side-branch catheter 31. The side-branch catheter includes distal end 32 which is configured for delivery in the patient's vasculature and proximal end 33 which remains outside the patient. First guide wire lumen 34A extends through at least a portion of side-branch catheter 31 depending on the type of catheter desired for a particular application. First guide wire lumen 34A preferably is defined by distal end 34B and side port 34C, which is typical of the so-called rapid-exchange-type catheters. Typically, a slit (not shown) extends from side port 34C to just proximal of the balloon portion of the catheter so that the catheter can be rapidly exchanged during a medical procedure, as is known.

The expandable member 35, which is typically a non-distensible balloon, has a first compressed diameter for delivery through the vascular system, and a second expanded diameter for implanting a stent. The expandable member 35 is positioned near distal end 32, and in any event between distal end 32 of first catheter 31 and side port 34C.

Referring to FIGS. 7A and 7B, tracking guide wire 36A, distal end 36B, and proximal end 36C all extend through first guide wire lumen 34A. Tracking guide wire 36A preferably is a stiff wire having a diameter of 0.014 inch, but can have a different diameter and stiffness as required for a particular application. A particularly suitable guide wire can include those manufactured and sold under the tradenames Sport® and Ironman®, manufactured by Advanced Cardiovascular Systems, Inc., Santa Clara, Calif. Tracking guide wire 36A is sized for slidable movement within first guide wire lumen 34A.

Stent delivery assembly 30 further includes second guide wire lumen 39A which is associated with expandable member 35. Second guide wire lumen 39A includes angle portion 39B and straight portion 39C, and is firmly attached to outer surface 40 of catheter 31, at a point just proximal to expandable member 35. Integrated stent-positioning guide wire 41A is sized for slidable movement within second guide wire lumen 39A. A slit 39D is formed in lumen 39A near its distal end so that the stiff guide wire 41A can bow outwardly as shown in FIG. 7B. The portion of guide wire 41A that bows out of slit 39D will limit the advancement of catheter 31 as will be further described infra. Integrated stent-positioning guide wire 41A has distal end 41B, and proximal end 41C which extends out of the patient. Again, it is preferred that integrated stent-positioning guide wire 41A be a fairly stiff wire as previously described, for the reasons set forth below in delivering and implanting the stents in the bifurcation.

In an alternative embodiment, catheter 31 can have an angled expandable member 42 as depicted in FIG. 8. The proximal end of the expandable member is angled to coincide with the angle of proximal angled stent 10 (not shown in FIG. 8 for clarity). This embodiment is particularly useful in delivering the angled stent since the second guide wire lumen 39A, and its angled portion 39B, have the same angle as the stent and the proximal end of the expandable member.

In further keeping with the invention, as depicted in FIGS. 9A–11D, proximal angled stent 10 is mounted on side-branch catheter 31 and implanted in side-branch vessel 5. The method of achieving proximal angled stent implantation is as follows.

In keeping with the preferred method of the invention, proximal angled stent 10 first is tightly crimped Angled portion 39B of second guide wire lumen 39A is angled to assist in rotating the side-branch catheter into proper position into the side-branch vessel. If the stent approaches side-branch vessel 5 in the incorrect position, as depicted in FIGS. 11A–11D, stent-positioning wire 41A would be forced to make a very acute angle. The wire stiffness, however, prevents this from happening and causes the wire to assume the position of least stress. To relieve this stress buildup, wire 41A creates a torque on angled portion 39B causing guide wire lumen 39A and side-branch catheter 31, with proximal angled stent 10, to rotate into the correct position. Preferably, slit 39D is formed on catheter 31 outer surface near angled portion 39B so that stent-positioning guide wire 41A can bow outwardly out of slit 39D thereby increasing the ability to torque the catheter and the proximal angled stent.

Thereafter, proximal angled stent 10 mounted on the expandable member 35 is aligned across the target area, and viewed under fluoroscopy, the acute angle 18 on the proximal end of the proximal angled stent is aligned at the intersection of side-branch vessel 5 and main-vessel 6 (the ostium of the side-branch vessel) so that the proximal angled stent completely covers the target area in side-branch vessel 5, yet does not extend into the main-vessel 6, thereby compromising blood flow. The expandable member 35, which is typically a non-distensible balloon, is expanded by known methods, thereby expanding the proximal angled stent into contact with side-branch vessel 5, and thereby implanting the proximal angled stent in the side-branch vessel. Thereafter, expandable member 35 is deflated and side-branch catheter assembly 31 is withdrawn from the patient's vasculature. The side-branch catheter 31 is designed so that both tracking guide wire 36A and stent-positioning guide wire 41A can be left in their respective vessels should sequential or simultaneous high pressure balloon inflation be required in each of the vessels in order to complete the stenting procedure. In other words, the integrated positioning wire can be unzipped through the slit (not shown) from the proximal 100 cm of the catheter thereby allowing it to act as a rapid exchange wire. Preferably, high pressure balloons are inflated simultaneously in the main vessel and proximal angled stents in order to avoid deforming one stent by unopposed balloon inflation within the other one. This additional step is a matter of physician choice. Utilizing this preferred method, side-branch vessel 5 can be stented without the need for stenting the main vessel, as shown in FIGS. 11A–11D.

If necessary, main-vessel 6 also can be stented after stenting the side-branch vessel. In that regard, and in keeping with the invention, main-vessel catheter assembly 50 is provided for implanting main-vessel stent 20, as depicted in FIGS. 12A to 13E. In one preferred embodiment, as shown in FIGS. 12A–12C, main-vessel catheter 50 includes distal end 51 which is configured for advancement within the patient's vasculature, and proximal end 52 which remains outside the patient. The main-vessel catheter includes guide wire lumen 53A having distal end 53B and side port 53C, which is proximal to the balloon portion of the catheter. Side port 53C is provided in a so-called rapid-exchange catheter system which includes a slit (not shown) as is known in the art. Expandable member 54 is located near distal end 51 of main-vessel catheter 50. Typically, expandable member 54 is a non-distensible balloon of the type known in the art for delivering and expanding stents.

In further keeping with the invention, positioning guide wire lumen 55A is positioned partly on the catheter shaft and partly on expandable member 54, and is configured for slidably receiving integrated stent-positioning guide wire 56A. Prior to stent delivery, guide wire 56A resides in guide wire lumen 55A and only during stent delivery is it then advanced into and through angled portion 55B of the lumen.

Other preferred embodiments for implanting main-vessel stent 20 in main-vessel 6 are depicted, for example, in FIGS. 12D–12F. This embodiment is identical to that depicted in FIGS. 12A–12C, with the addition of ramp 57 which is mounted on balloon 35 and provides a slight incline for guide wire 56A as it exits guide wire, lumen 55A. As the guide wire slides along ramp 57, distal portion 56B of the guide wire will move radially outwardly which helps position the guide wire and orient it into the side-branch vessel. In another preferred embodiment for implanting the main-vessel stent in the main vessel, as depicted in FIGS. 12G–12I, guide wire lumen 55A passes underneath main-vessel stent 20 and on top of balloon 54. The distal end 55B curves along the balloon so that as guide wire 56B advances out of the distal end 55B of the lumen, it is travelling radially outwardly so that it can more easily locate and advance into the side-branch vessel 5.

Figure 12J:
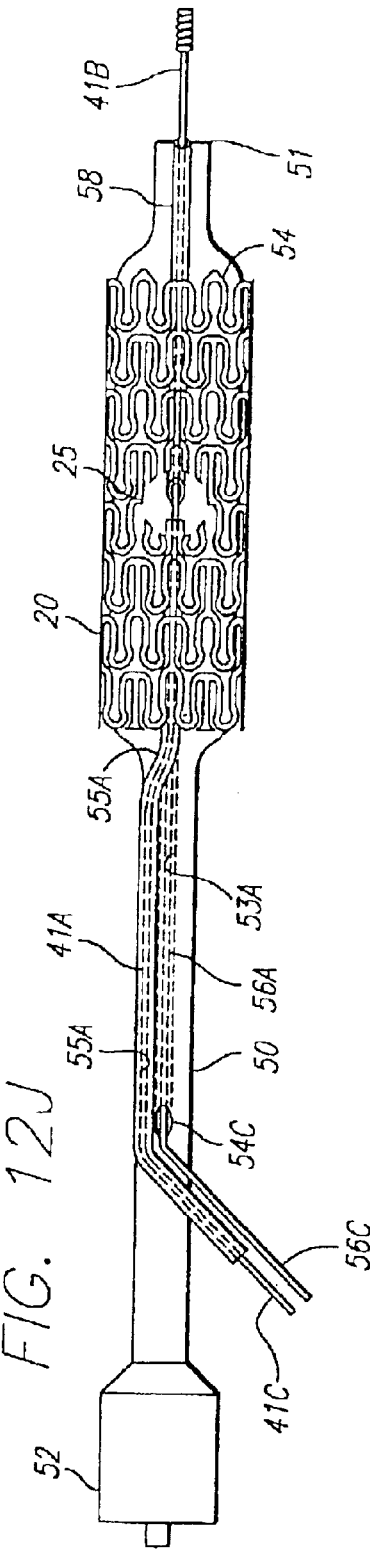
FIGS. 12J–12L depict an elevational view, partially in section, of an alternative embodiment of the main-vessel catheter of FIGS. 12A–12C in which a portion of the guide wire lumen passes under the stent.
Figure 12K:
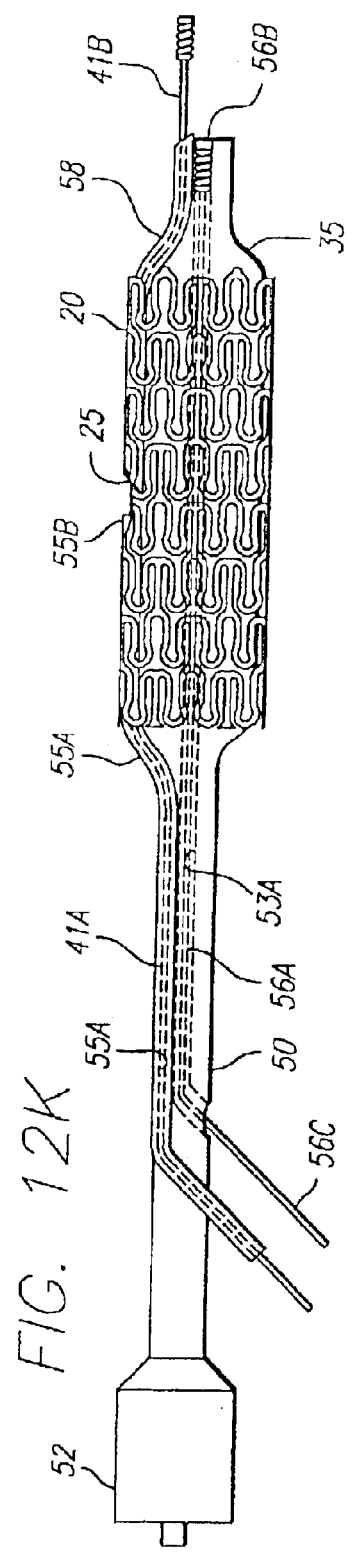
Figure 12L:
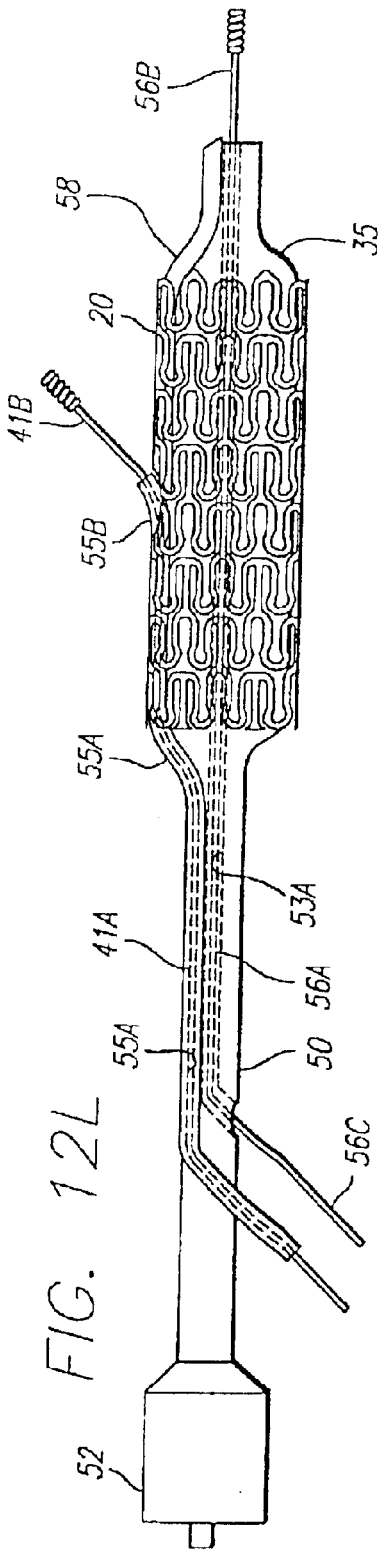
Figure 13C:
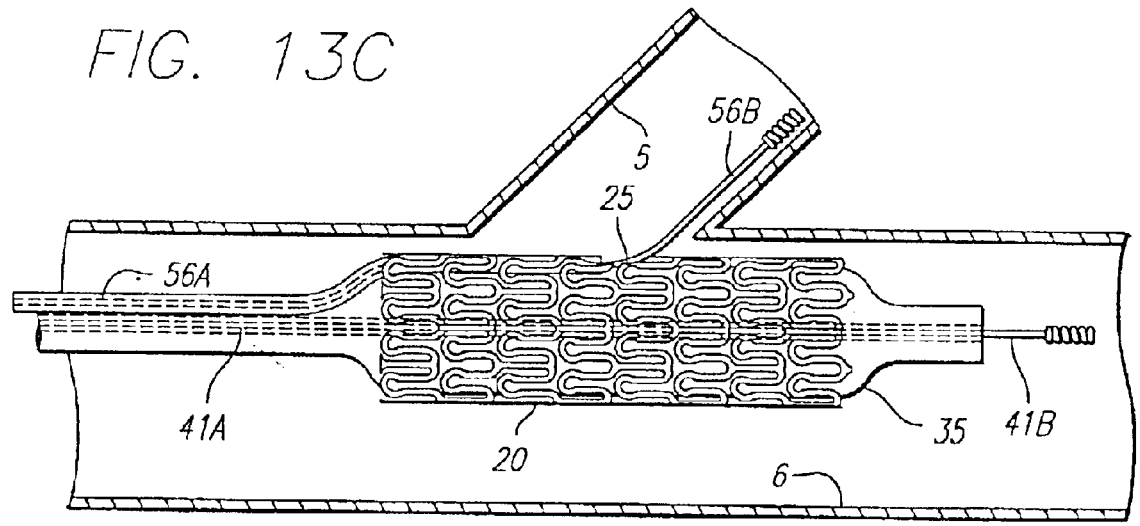
Figure 13D:
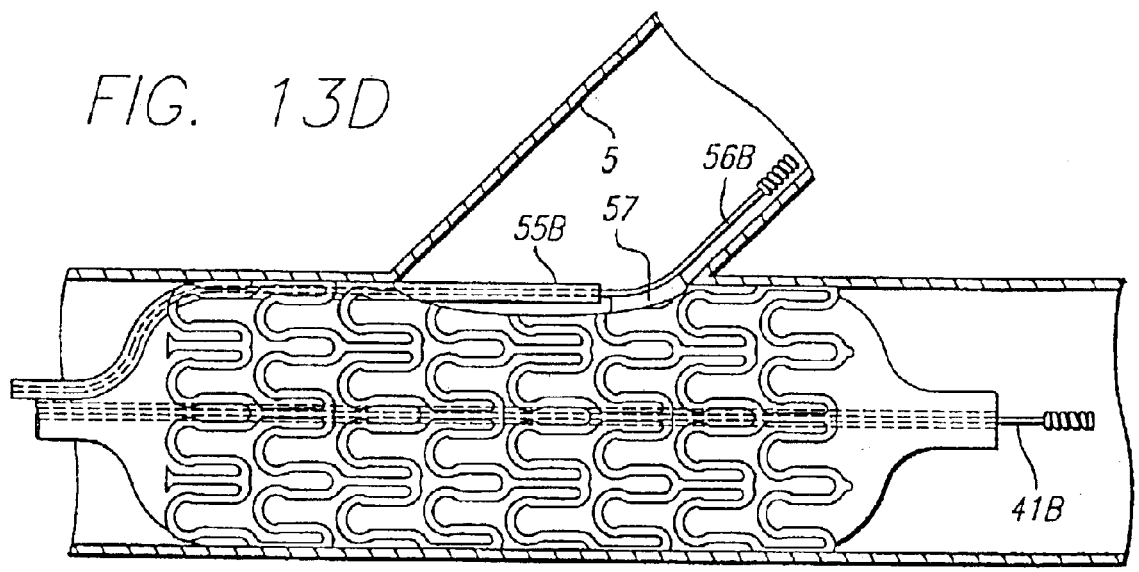
Figure 13E:
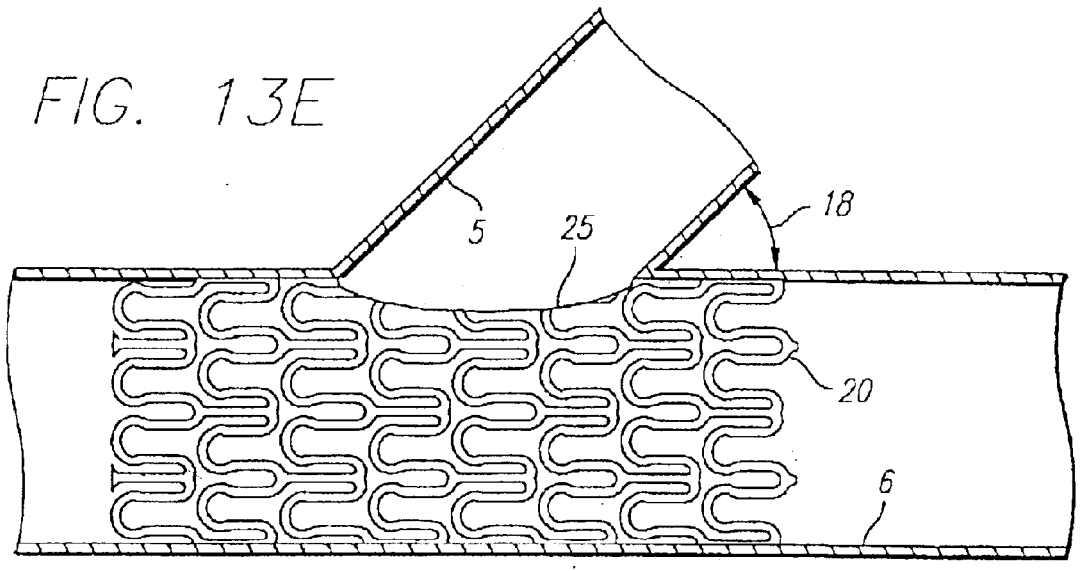

In still another preferred embodiment for implanting main-vessel stent 20 in the main-vessel 6, as depicted in FIGS. 12J–12L, guide wire lumen 55A is positioned under stent 20 and terminates at distal end 55B in the middle of aperture 25. The distal end 55B of the guide wire lumen will spring outwardly which facilitates advancing guide wire distal end 41B into the side branch vessel. A distal guide wire lumen 58 is attached to the balloon 54 outer surface and extends from aperture 25 to essentially the distal end of the catheter.

In one preferred method of implanting main-vessel stent 20 in main-vessel 6, as depicted in FIGS. 12A–12I and 13A–13D, guide wire 41A remains in position in main-vessel 6, while the side-branch guide wire 36A is withdrawn from the patient. Main-vessel catheter 50 is backloaded onto guide wire 41A by inserting proximal end 41C of the wire into the distal end of the catheter and into guide wire lumen 53A. Main-vessel catheter 50 is advanced over guide wire 41 A and viewed under fluoroscopy until main-vessel stent 20 is positioned in main-vessel 6, just proximal to side-branch vessel 5. The distal end 56B of the integrated stent-positioning guide wire 56A is then advanced by the physician pushing on proximal end 56C from outside the body. The distal end 56B of wire 56A advances into and through positioning guide wire lumen 55A and passes underneath the proximal end of the main-vessel stent 20 and exits the angled portion 55B of the lumen and enters side-branch vessel 5. The main-vessel catheter 50 is then advanced distally into the main vessel until resistance is felt from the stent-positioning guide wire 56A pushing up against the ostium of the side-branch vessel. The stiffness of stent-positioning guide wire 56A causes the main-vessel catheter 50, with main-vessel stent 20 thereon, to rotate so that aperture 25 is facing the side-branch vessel 5 ostium and proximal angled stent 10 already implanted.

Figure 14:
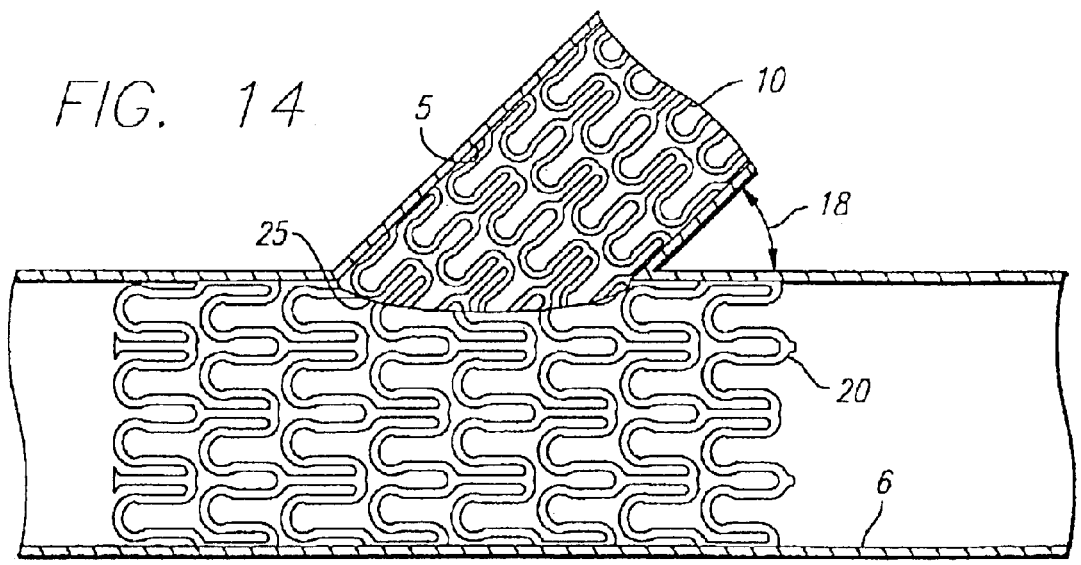
FIG. 14 is an elevational view of a bifurcated vessel in which the proximal angled stent is implanted in the side-branch vessel and a main vessel stent is implanted in the main vessel.

Expandable member 54, which is typically a non-distensible expandable balloon, is inflated thereby expanding main-vessel stent 20 into contact with main-vessel 6. Aperture 25 correspondingly expands and when properly aligned, provides a blood flow path between aperture 25 and proximal angled stent 10 implanted in side-branch vessel 5. As can be seen in FIGS. 12A–12I and 13A–13D, positioning guide wire lumen 55A is positioned on expandable member 54, such that when the expandable member is inflated, positioning guide wire lumen 55A does not interfere with implanting main-vessel stent 20. After the main-vessel stent is implanted in the main vessel, expandable member 54 is deflated, and main-vessel catheter 50 withdrawn from the patient. As seen in FIG. 14, the bifurcated vessel has been fully covered by the stents, side-branch vessel 5 is covered by proximal angled stent 10, and main-vessel 6 is covered by main-vessel stent 20, so that no portion of bifurcation 4 is left uncovered and there is no overlap in the implanted stents.

In an alternative method of implanting main-vessel stent 20 in main-vessel 6 as depicted in FIGS. 12J–12L, tracking guide wire 41A is advanced through guide wire lumen 55A and guide wire lumen 58 so that it advances distally of the distal end 51 of the catheter. Thus, guide wire distal end 41B is advanced into the main vessel so that it is distal of the side-branch vessel. Guide wire 56A, which until this point has remained within guide wire lumen 53A (see FIG. 12K), is advanced distally as depicted in FIG. 12L and advanced into the main vessel distally of the side-branch vessel. Guide wire 41A is then withdrawn proximally through guide wire lumen 58 until guide wire distal end 41B is able to exit guide wire lumen distal end 55B, as shown in FIG. 12L. Since guide wire lumen 55B is preformed and has bias, it will spring outwardly. Guide wire 41A can then be advanced into the side-branch vessel for further positioning. As the catheter 50 is advanced over the guide wires, distal portion 41B of the guide wire will push against the ostium of the side-branch vessel thereby insuring the location of main-vessel stent 20, and importantly aperture 25 will align with the opening to the side-branch vessel 5.

A non-angulated stent (see FIG. 15) can be implanted using the catheter system of FIGS. 7A–11D for stenting a side-branch vessel having an origin approaching 90° in its takeoff from the main vessel. In this circumstance the positioning wire serves solely to arrest the forward movement of the stent precisely at the origin of the vessel for more precise positioning. However, acute angle 18 is appropriate for a bifurcated vessel 4 in which the angulation is acute angle 18, or less than 90°. Thus, consideration could be given to standard 30°, 45°, and 60° angled stent designs for proximal angled stent 10, which should provide sufficient luminal wall coverage when keeping with the present invention. Proximal angled stent 10 has a wide range of applicability and can be used for stenting ostial side-branch lesions, ostial circumflex or left anterior descending (LAD) lesions where the bifurcation is an acute angle, or less than 90°, and ostial lesions involving the angulated origin of a right coronary or vein graft. Importantly, the stents of the present invention provide full coverage of the ostial intima without protruding into the main vessel or without compromising subsequent access to the distal portion of the main vessel.

In order to assist in properly aligning both proximal angled stent 10 and main-vessel stent 20 in side-branch vessel 5 and main-vessel 6, respectively, positioning guide wire lumen 39A, on side-branch catheter 31, and guide wire lumen 55A, on main-vessel catheter 50, can be radiopaque, or have a radiopaque marker associated therewith so that they are visible under fluoroscopy. Thus, when advancing side-branch catheter 31 and main-vessel catheter 50, the proper orientation can be more easily determined by viewing the position of positioning guide wire lumen 39A in connection with main-vessel 6 or positioning guide wire lumen 55A in connection with aligning aperture 25 with side-branch vessel 5. Additionally, positioning guide wire 56A for positioning main-vessel stent 20 and positioning guide wire 41A for positioning angled stent 10 are either radiopaque or have radiopaque portions, such as gold markers, to assist in positioning and orienting the catheters and stents during implantation and deployment.

While the foregoing description includes implanting proximal angled stent 10 in side-branch vessel 5 prior to implanting main-vessel stent 20 in main-vessel 6, in an alternative preferred embodiment, the implanting procedure can be reversed. However, it should be understood that by implanting main-vessel stent 20 in main-vessel 6, and subsequently implanting proximal angled stent 10 in side-branch vessel 5, aperture 25 must be carefully aligned with side-branch vessel 5 so that side-branch catheter 31 can be advanced through expanded main-vessel stent 20 and aperture 25 and into side-branch vessel 5 for implanting proximal angled stent 10.

While side-branch catheter 31 and main-vessel catheter 50 have been described herein as being of the rapid-exchange type, they also can be of a conventional over-the-wire-type catheter. In over-the-wire-type catheters, the guide wire lumen extends from the distal end of the catheter to the proximal end with no side port as is found in the rapid-exchange-type catheters. Typical of over-the-wire-type catheters is the type disclosed in U.S. Pat. Nos. 4,323,071 and B1 4,323,071, which are incorporated herein by reference, and are commonly assigned and commonly owned by Advanced Cardiovascular Systems, Inc., Santa Clara, Calif.

Figure 15:
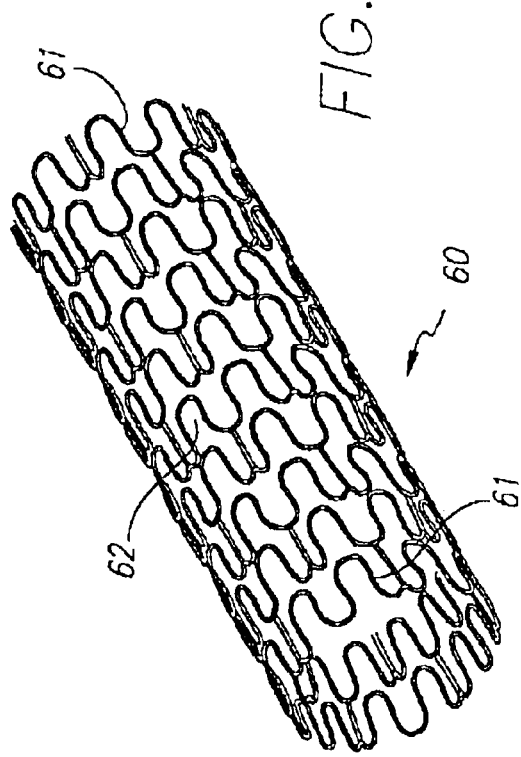
FIG. 15 is a perspective view of the main-vessel stent of the present invention for deployment in the main vessel, where a targeted stent cell provides an opening through which a guide wire can pass.
Figure 16A:
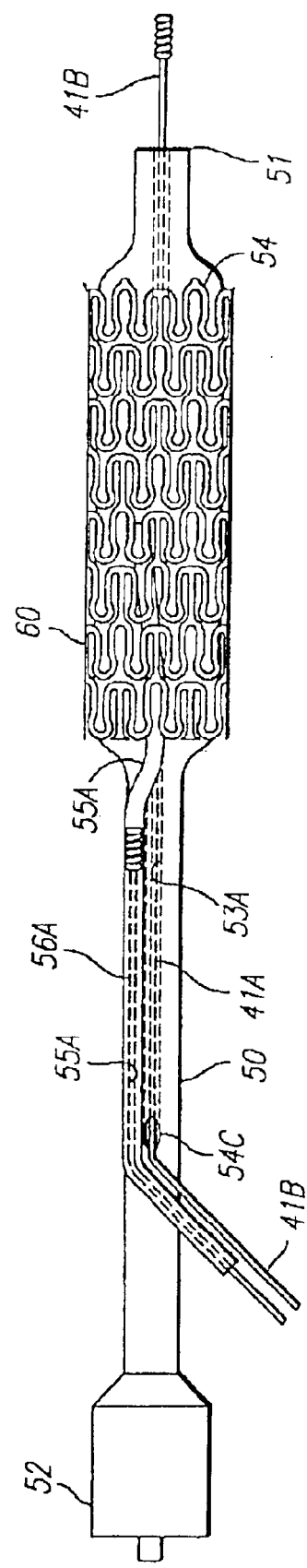
Figure 17:
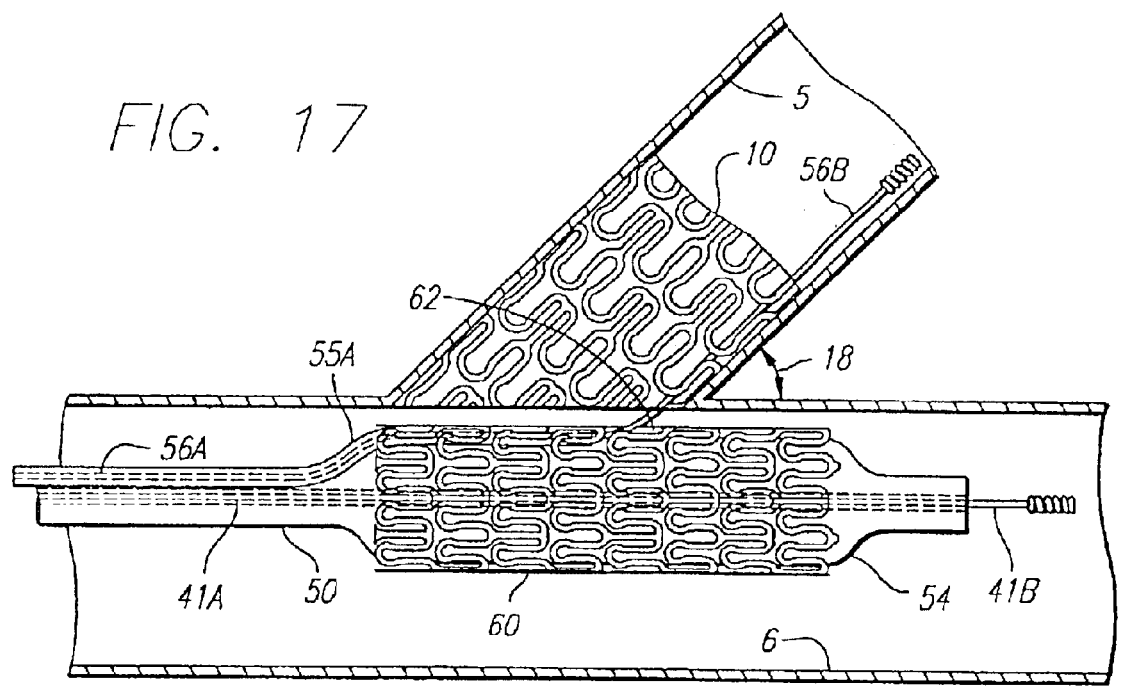
FIG. 17 is an elevational view of a bifurcation in which a main-vessel stent is positioned in a main vessel so that it spans the opening to the side-branch vessel.

In one preferred embodiment of the invention, as depicted in FIG. 15, main-vessel unmodified stent 60 can be configured without the side aperture 25 of stent 20. Upon expansion, the individual strut members 61 of unmodified stent 60 expand sufficiently to permit a balloon catheter to be inserted therethrough, and expanded, to form an aperture which corresponds to the opening to side-branch vessel 5.

In one preferred method of stenting the bifurcation, side-branch vessel 5 is first stented as described, for example, in the manner shown in FIGS. 9A through 11D. Thereafter, main-vessel 6 is stented with unmodified main-vessel stent 60, which does not have an aperture formed in the side of the stent. As shown in FIGS. 15–18, unmodified stent 60 is mounted on expandable portion 54 of main-vessel catheter 50. Main-vessel catheter 50 is backloaded onto the proximal end of guide wire 41A which is already in position in the main vessel. Main-vessel catheter 50 is advanced over the guide wire and viewed under fluoroscopy until stent 60 is positioned in the main vessel about one cm proximal to the side-branch vessel. The distal end 56B of integrated stent-positioning guide wire 56A is then advanced by the physician by pushing the proximal end 56C from outside the body. The distal end 56B of wire 56A travels through guide wire lumen 55A and passes underneath the proximal end of unmodified stent 60 and exits the angled end of the lumen 55B and enters side-branch vessel 5. The main-vessel catheter 50 is then advanced distally into the main vessel until resistance is felt from the stent-positioning guide wire 56A pushing up against the ostium of side-branch vessel 5. The stiffness of stent-positioning guide wire 56A causes the main-vessel catheter 50 with unmodified stent 60 to rotate so a stent cell 62 is precisely facing the side-branch vessel 5 ostium. Expandable member 54 is expanded by known means so that unmodified stent 60 expands into contact with main-vessel 6. Expandable member 54 is then deflated, catheter 50 is withdrawn from the patient's vascular system, leaving guide wire 56A in the side branch.

Figure 18:
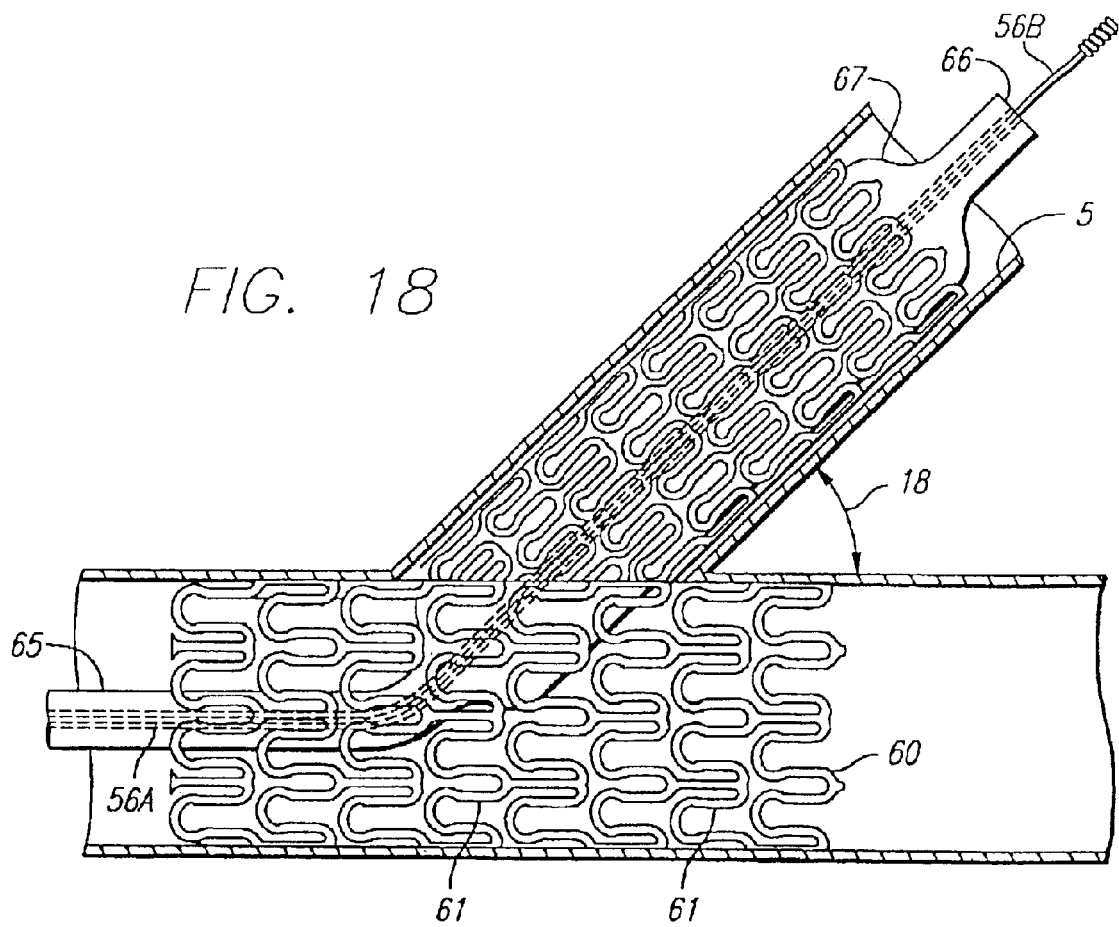
FIG. 18 is an elevational view of a bifurcation in which a main-vessel stent is implanted in the main vessel and a balloon catheter is partially inserted into a side-branch vessel to form an opening through the targeted stent cell of the main stent.

At this point, proximal angled stent 10 is implanted in the side-branch vessel and unmodified main-vessel stent 60 is implanted and extends across side-branch vessel 5. In order to provide an opening in unmodified main-vessel stent 60 that aligns with the opening to the side-branch vessel, third catheter 65, which can be a standard PTCA catheter, is backloaded onto guide wire 56A, already in side-branch vessel 5, and advanced within the patient's vascular system over the guide wire. As shown in FIG. 18, distal end 66 of catheter 65 is advanced over guide wire 56A until the distal end 66 of catheter 65 begins to pass through cell 62 of unmodified main-vessel stent 60 and enter side-branch vessel 5. Catheter 65 can be of a known type used in angioplasty, as described above, having a non-distensible member or balloon 67. Once balloon 67 is positioned through stent cell 62 and in the opening of side-branch vessel 5, it is expanded, thereby expanding some of struts 61 comprising unmodified stent 60 and forming a substantially circular opening from main-vessel 6 through unmodified stent 60 and into side-branch vessel 5. In essence, balloon 67 spreads apart some of the struts of unmodified stent 60 to form an opening in stent 60 that corresponds to the opening to side-branch vessel 5, thereby providing a clear blood flow path between the main vessel and the side-branch vessel.

Unmodified main-vessel stent 60 is positioned such that it crosses the opening to side-branch vessel 5. As set forth above, a particularly well suited stent for this embodiment includes a stent distributed under the tradename MultiLink® Stent, manufactured by Advanced Cardiovascular Systems, Inc., Santa Clara, Calif. By implanting unmodified main-vessel stent 60 in main-vessel 6 with an appropriate stent cell precisely aligned with the side-branch ostia, dilatation through this same cell over wire 56A assures a fully expanded and non-distorted cell at the ostium of side-vessel 5.

Figure 19A:
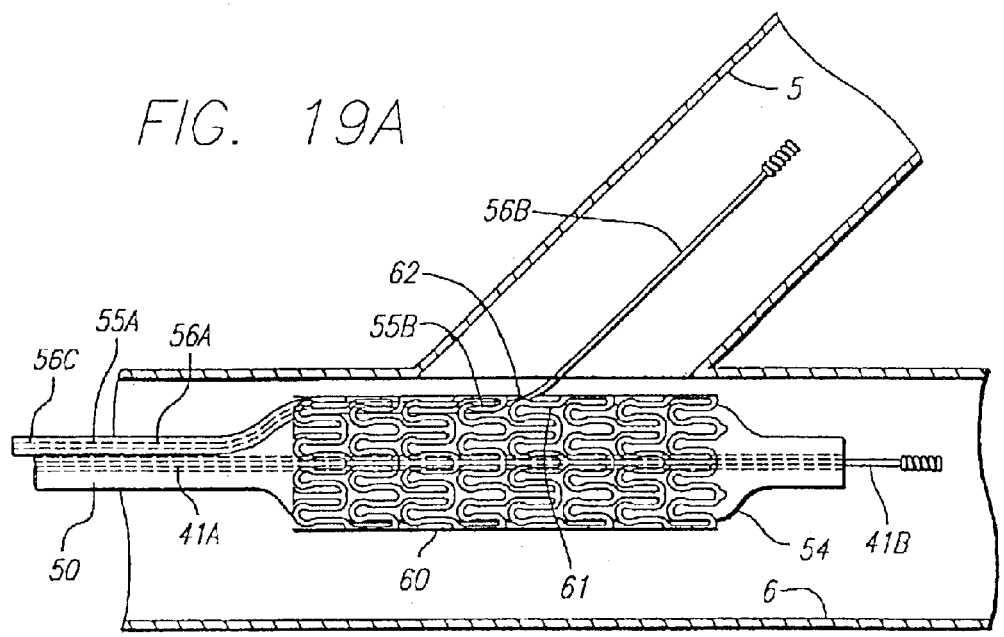
Figure 19B:
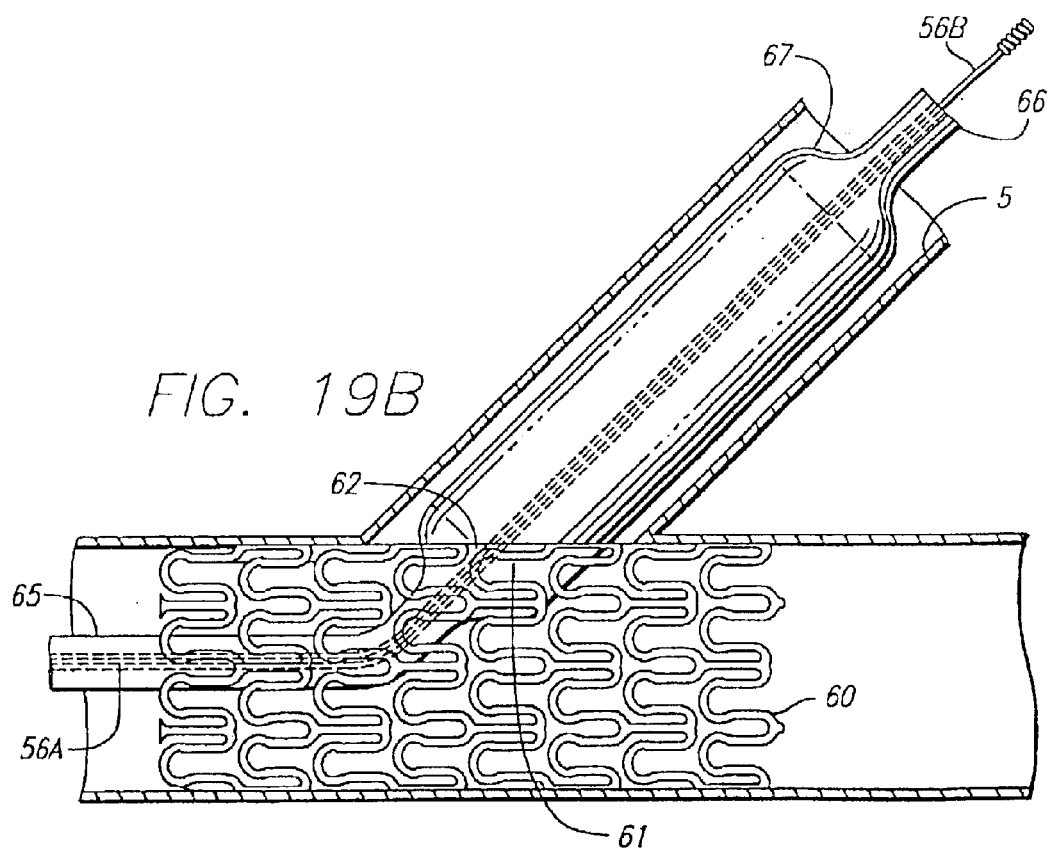

In an alternative embodiment, as shown in FIGS. 19A–19C, unmodified stent 60 is implanted first, then the side-branch proximal angled stent 10 is implanted. In the preferred method of deploying unmodified stent 60, the unmodified stent 60 can be mounted on expandable portion 54 of main-vessel catheter 50. Main-vessel catheter 50 is backloaded onto the proximal end of guide wire 41A. Main-vessel catheter 50 is advanced over guide wire 41A and viewed under fluoroscopy until unmodified stent 60 is positioned in main-vessel 6, proximal to side-branch vessel 5. The distal end of the integrated stent-positioning guide wire 56B is then advanced by the physician pushing the proximal end 56C from outside the body. The distal end 56B of wire 56A travels through second guide wire lumen 55A and passes underneath the proximal end of unmodified stent 60 and exits the angled end of the lumen 55B and enters sidebranch vessel 5. The main-vessel catheter 50 is then advanced distally into the main vessel until resistance is felt from the stent-positioning guide wire 56A pushing up against the ostium of the side-branch vessel 5. The stiffness of stent-positioning guide wire 56A causes the main-vessel catheter 50 with unmodified stent 60 to rotate so a stent cell 62 is precisely facing the side-branch vessel 5 ostium. Expandable member 54 is expanded by known means so that unmodified stent 60 expands into contact with main-vessel 6. Expandable member 54 is then deflated, and catheter 50 is withdrawn from the patient's vascular system, leaving guide wire 56A in side branch 5.

In further keeping with the preferred method of stenting, as shown in FIG. 19B, third catheter 65, which can be a standard PTCA catheter, is backloaded onto guide wire 56A already in side-branch vessel 5 and advanced within the patient's vascular system over the guide wire. Distal end 66 of catheter 65 is advanced over guide wire 56A until the distal end 66 of the catheter begins to pass through struts 61 of stent cell 62 of unmodified main-vessel stent 60 and enter side-branch vessel 5. Catheter 65 can be of a known type used in angioplasty, as described above, having a non-distensible member or balloon 67. Once balloon 67 is positioned through a stent cell 62 the opening of side-branch vessel 5, it is expanded, thereby expanding some of the struts comprising unmodified stent 60 and forming a substantially circular opening from main-vessel 6 through unmodified stent 60 and into side-branch vessel 5. In essence, balloon 67 spreads apart the struts 61 of unmodified stent 60 to form an opening in the unmodified stent that corresponds to the opening to side-branch vessel 5, thereby providing a clear opening for further stenting side-branch vessel 5.

With the main vessel now stented as depicted in FIGS. 19A–19C, side-branch vessel 5 is stented in the same manner as described in FIGS. 9–11. The only difference is that in FIG. 19, unmodified main-vessel stent 60, already is implanted when catheter 31 is advanced into side-branch vessel 5. Side-branch catheter 31 is backloaded onto guide wire 36A already in side-branch vessel 5. Side-branch catheter 31 is then advanced until the distal tip of side-branch catheter 31 just enters the side-branch vessel 5 ostium. The distal end 41B of the integrated guide wire 41A is then advanced by the physician pushing the proximal end 41C from outside the body. The distal end 41B of the integrated-stent-positioning guide wire travels through second guide wire lumen 39A and angled portion 39B and passes close to the proximal end of proximal angled stent 10 and expandable member 35 and exits lumen 39B. The stent-positioning guide wire 41A is advanced until the distal end 41B is distal to side-branch vessel 5. The catheter is then advanced into the side-branch vessel until resistance is felt from the stent-positioning guide wire 41A pushing up against the ostium of the side-branch vessel. As previously described, stent-positioning wire 41A is relatively stiff, as is tracking guide wire 36A, so that they can properly orient side-branch catheter 31 as it is advanced into the side-branch vessel. Angled portion 39B of second guide wire lumen 39A is angled to assist in rotating the side-branch catheter into proper position into side-branch vessel 5. If the stent approaches the side-branch vessel in the incorrect position, the stent-positioning wire 41A would be forced to make a very acute angle. The wire stiffness, however, prevents this from happening and causes the wire to assume the position of least stress. To relieve this stress buildup, wire 41A creates a torque on angled portion 39B causing guide wire lumen 39A and side-branch catheter 31 with proximal angled stent 10 to rotate into the correct position. Once the proximal angled stent is positioned in side-branch vessel 5, expandable member 35 is expanded so that the proximal angled stent expands into contact with side-branch vessel 5, making sure that proximal end 14 of proximal angled stent 10 covers and is aligned with the side-branch vessel 5 at bifurcation 4. Proximal end 14 is aligned so that it coincides with acute angle 18, thereby ensuring that all portions of side-branch vessel 5 are covered by the proximal angled stent, where side-branch vessel 5 meets main-vessel 6. An unobstructed blood-flow path now exists between expanded unmodified stent 60 and main-vessel 6 through the opening previously formed and into side-branch vessel 5 and through implanted proximal angled stent 10.

Prior art devices that have attempted to first stent the main vessel and randomly select a stent cell to expand for alignment with the side-branch vessel, have generally failed. One such approach, known as the "monoclonal antibody" approach, as depicted in FIGS. 19D and 19E, depict what can happen when an inappropriate target stent cell is selected randomly and then expanded by a high pressure balloon. As shown in FIG. 19D, which is a view looking down side-branch vessel 5 in cross-section at a prior art stent 68, the physician randomly selects stent cell 69 which is a sub-optimal cell to expand with the balloon portion of a catheter. As-depicted in FIG. 19E, after balloon expansion in the suboptimal cell 69, entry into the cell with a catheter may be impossible or, if accomplished, expansion of the balloon may be incomplete. The aperture created will be inadequate and major distortion in the adjacent stent struts may occur. Consequences may include subacute thrombosis or restenosis. With the present invention, as shown in FIGS. 19A–19C, the target stent cell 62 is the optimal cell for expansion, and is preselected with a wire in place before stent deployment (that same wire remaining in place for subsequent access), and is oriented optimally with respect to the side-branch ostium prior to deployment. The resulting expansion as shown in FIG. 19F, guarantees an optimal aperture where the stent struts have been expanded providing a blood flow path from the main vessel to the side-branch vessel.

Figure 20A:
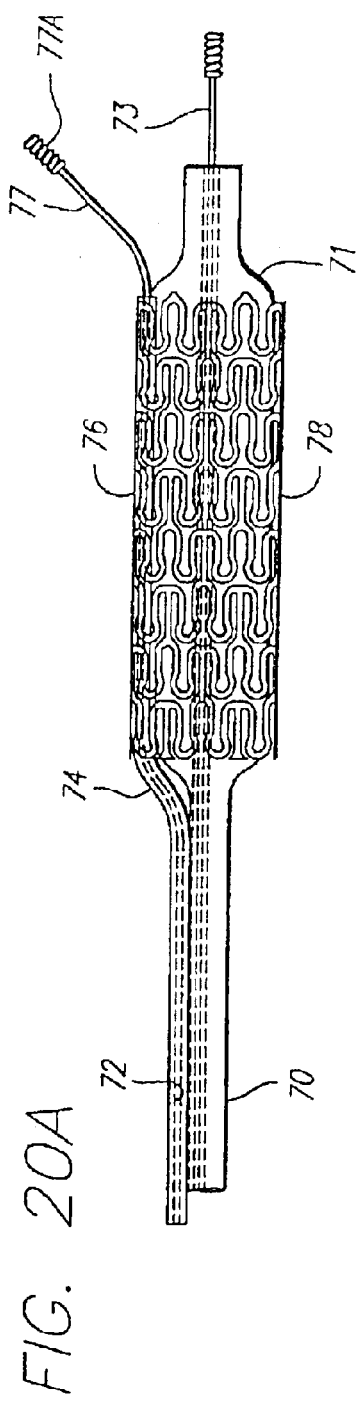
FIG. 20A is an elevational view, partially in section, depicting a main vessel catheter in which the main vessel stent is mounted over a positioning guide wire lumen.
Figure 20B:
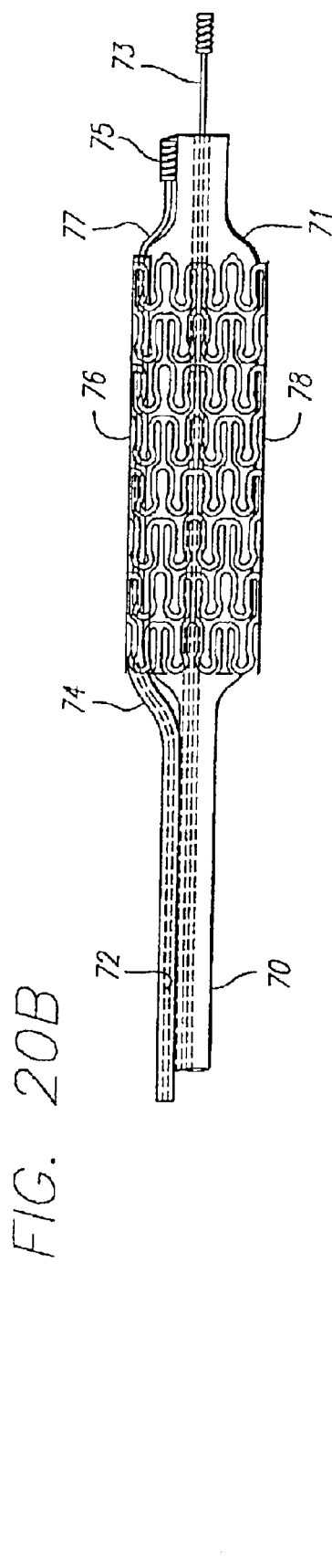
FIG. 20B is an elevational view, partially in section, of a main vessel catheter depicting the main vessel stent mounted over a section of the positioning guide wire lumen, with a distal portion of the guide wire lumen associated with the distal tip of the catheter.
Figure 20C:
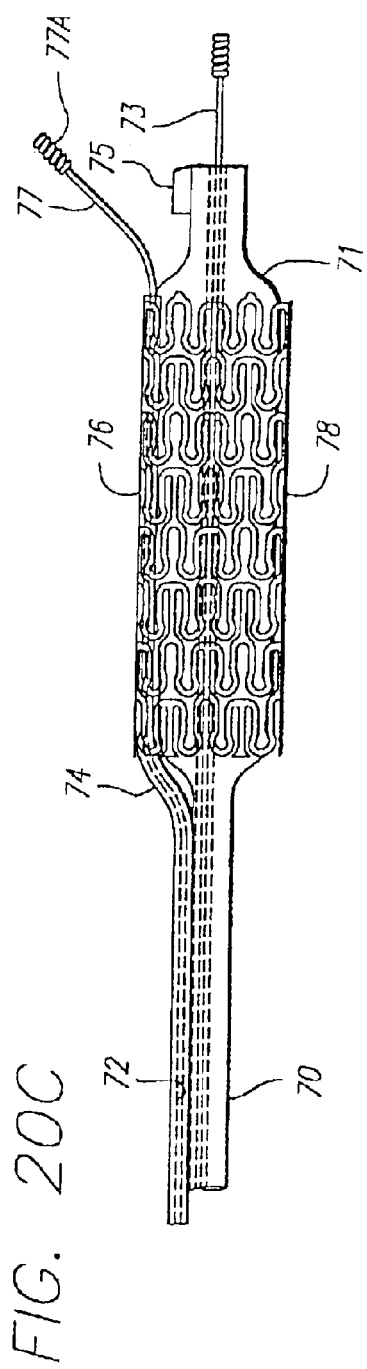
FIG. 20C is an elevational view, partially in section, of the catheter of FIG. 20B depicting the positioning guide wire advanced out of the positioning guide wire lumen.

In another alternative embodiment for stenting a bifurcation, as depicted in FIGS. 20A–20C, main-vessel catheter 70 includes expandable member 71 near its distal end, while the proximal end of the catheter (not shown) is similar to those previously described and can be either of the rapid-exchange or over-the-wire types. Catheter 70 includes tracking guide wire lumen 72 for slidably receiving tracking guide wire 73, lumen 72 extending at least partially through the catheter in the rapid-exchange configuration and all the way through the catheter in the over-the-wire configuration. The catheter also includes a positioning guide wire lumen 74 that is associated with the catheter outer surface and extends onto and is attached to at least a portion of expandable member 71. As shown in FIG. 20A, positioning guide wire lumen 74 extends along the expandable member and ends just at the distal taper of the expandable member. As depicted in FIGS. 20B and 20C, positioning guide wire lumen 74 can be formed of two sections, namely distal section 75 attached to the distal tip of the catheter, and proximal section 76 extending along and attached to the expandable member and the catheter. As previously described, guide wires 73,77 are intended to be relatively stiff wires so that they can more easily maneuver the catheter. In these embodiments, stent 78 is mounted on the expandable member and over positioning guide wire lumen 74. Positioning guide wire 77 is configured for slidable movement within positioning lumen 74.

In the preferred method of stenting a vessel just proximal to a bifurcation using main-vessel catheter 70, tracking guide wire 73 is first positioned within the main vessel as previously described. The catheter is then backloaded onto the guide wire by inserting the wire into the tracking guide wire lumen 72 and advancing the catheter into the patient's vascular system. At this point, positioning guide wire 77 resides within positioning guide wire lumen 74 and is carried into the main vessel where it will be released and advanced. Once the catheter has reached the target area, positioning guide wire 77 is advanced distally out of the positioning guide wire lumen (for FIG. 20A) or pulled back slightly out of distal section 75 of the positioning guide wire lumen (for FIGS. 20B and 20C). Once released by removal of the guide wire, distal section 75 will spring out so that the positioning guide wire can seek out and be advanced into the side-branch vessel. Once the positioning guide wire is advanced in the side-branch vessel, the catheter is again advanced and the stent is implanted in the main vessel in a manner similar to that described for other embodiments. The catheter of FIGS. 20A–20C is designed to allow deployment of a stent very near but not "snowplowing" a bifurcation or side branch and is configured for treating bifurcations as depicted in FIGS. 23A–25B. A commonly encountered situation in which catheter 70 would be used is an LAD that has disease right at and proximal to the diagonal take-off. After a careful look at multiple views, the physician should be convinced that the diagonal is spared, but the lesion is very close and or immediately adjacent to the diagonal take-off, as shown in FIG. 20D. It is very difficult to position a standard stent in the LAD and be certain that the lesion is fully covered and the diagonal is not snowplowed or jailed. The catheter 70, having one wire in the LAD (main vessel) and the other in the diagonal (side-branch vessel), would allow precise definition of the bifurcation and avoid these problems. Square stent 78A, which has both ends transverse to the stent axis, could be deployed just proximal to the carina, in which case the stent distal end may need to be flared a bit, or more likely, relaxed back to where the positioning guide wire 77 is resting against the proximal aspect of the ostium, visually defining the ostium in relationship to the stent and allowing precise deployment.

Figure 20E:
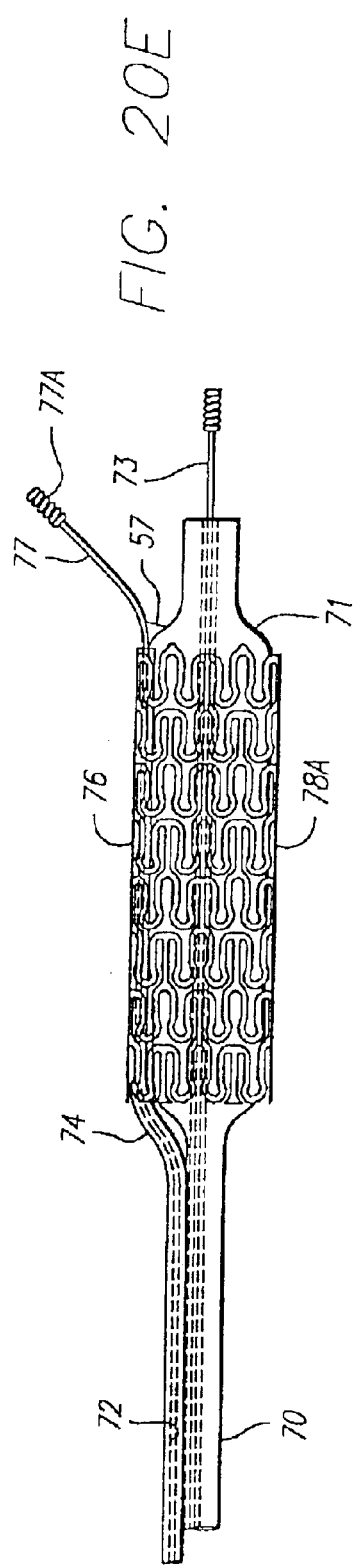
FIG. 20E is an elevational view, partially in section, depicting the main-vessel catheter of FIG. 20A having a ramp to assist in positioning the guide wire.
Figure 21:
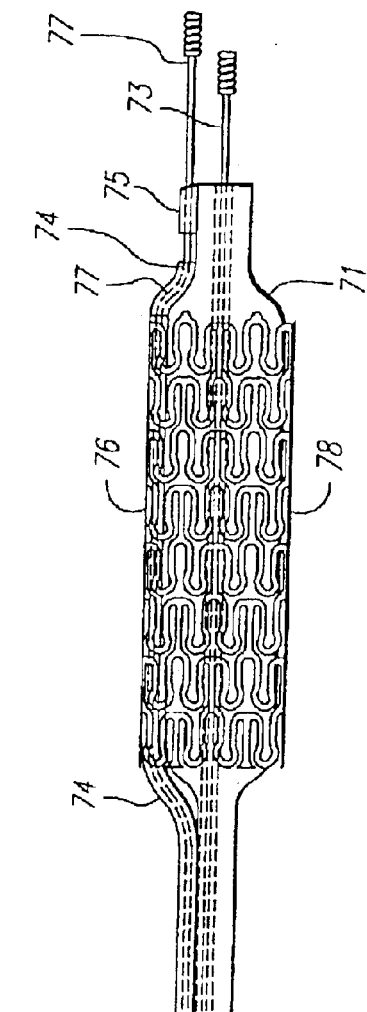
FIGS. 21 and 22 are elevational views, partially in section, depicting an alternative embodiment of the main-vessel catheter of FIG. 20B in which the distal end of the guide wire lumen springs away from the expandable balloon.
Figure 22:
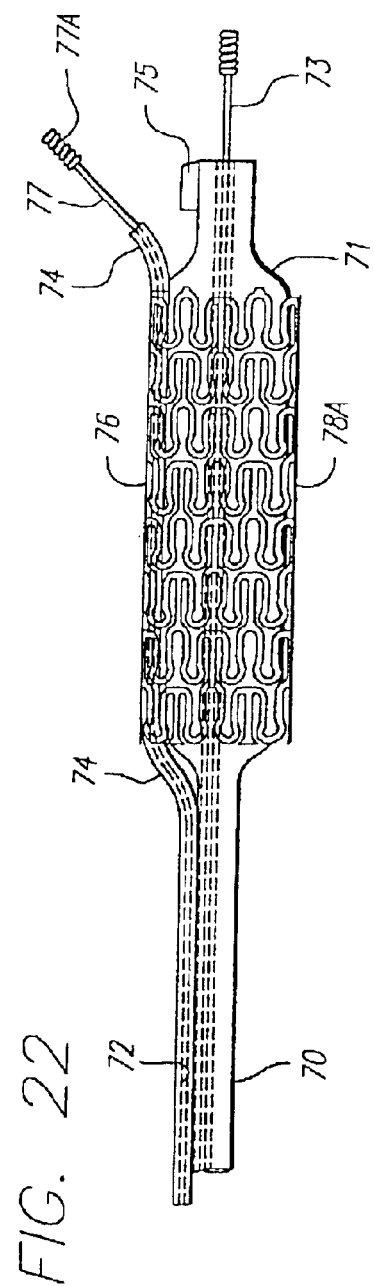
Figure 23A:
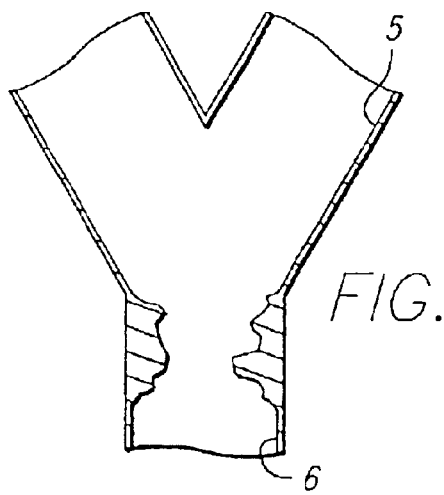
FIGS. 23A–23B, 24A–24B, 25A–25B, and 26A–26B, are elevational views of various bifurcations which are indicated for receiving main vessel and side-branch vessel stents deployed by the catheters of the present invention.
Figure 23B:
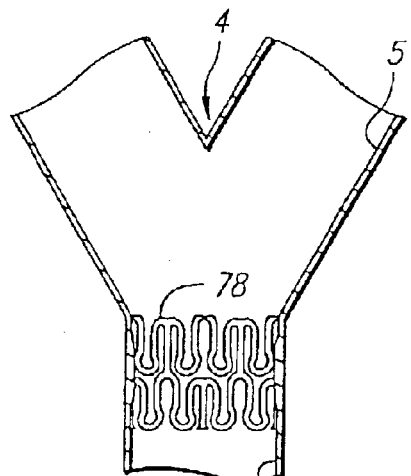
Figure 24A:
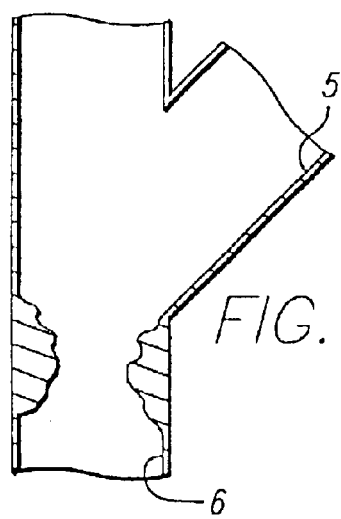
Figure 24B:
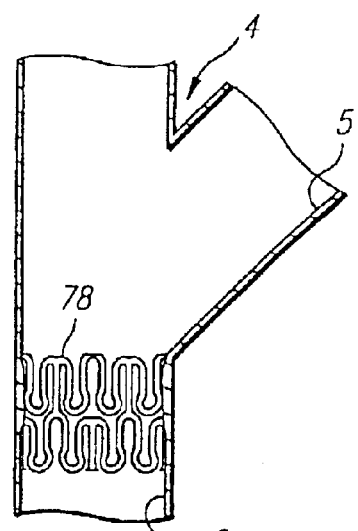
Figure 25A:
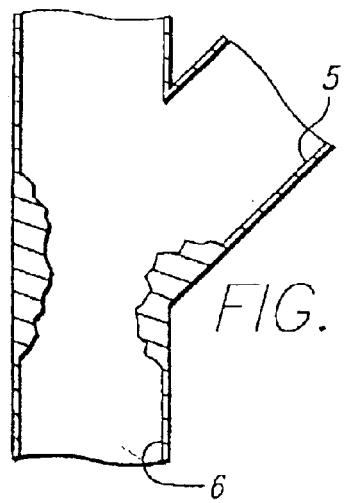
Figure 25B:
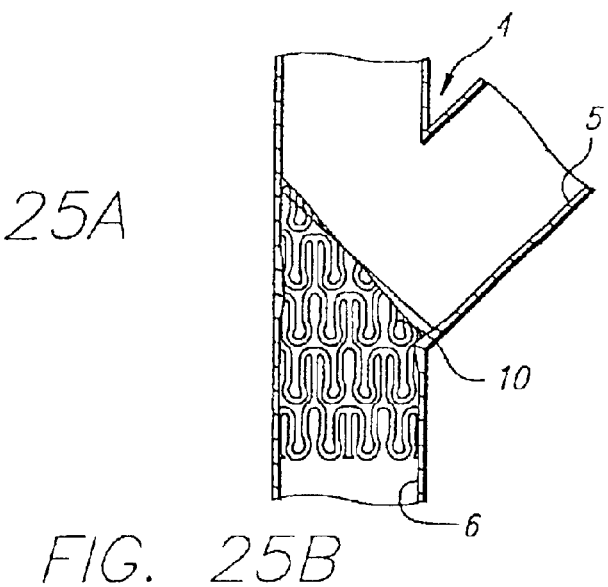
Figure 26A:
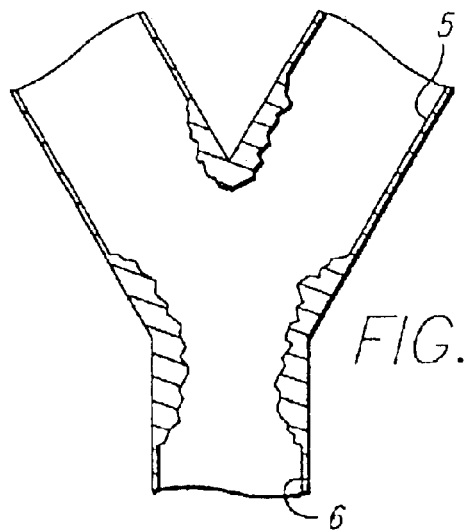
Figure 26B:
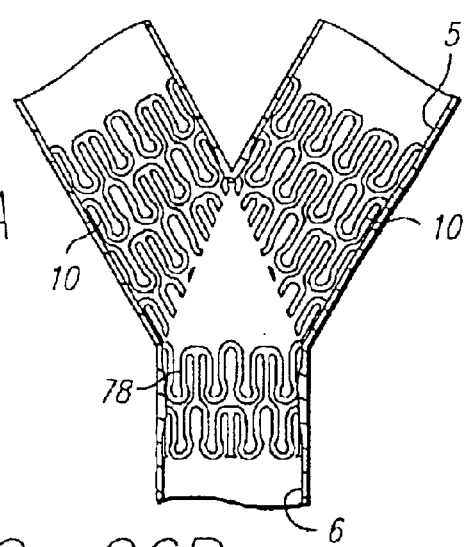
Figure 29A:
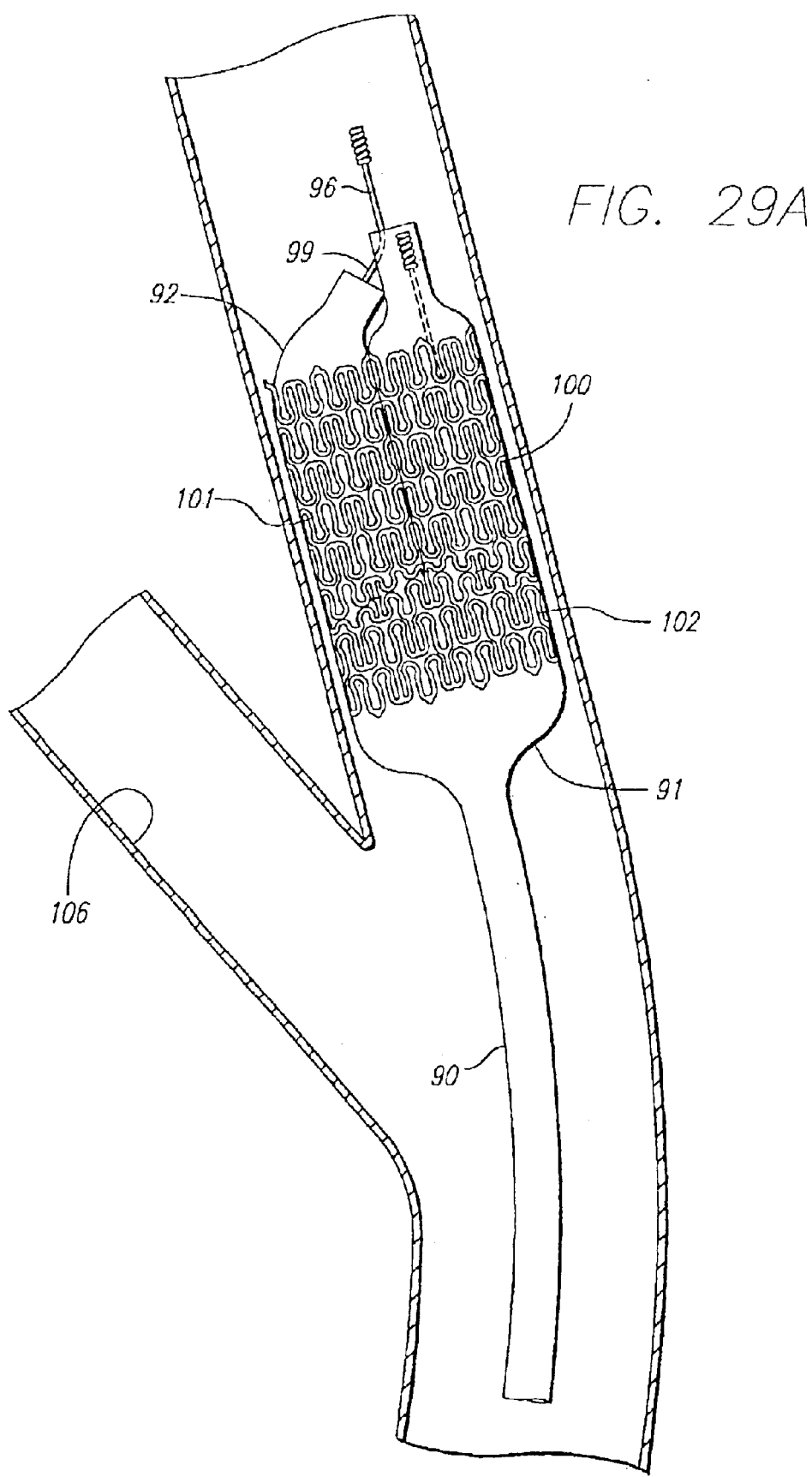
FIG. 29A is an elevational view, partially in section of a bifurcation in which the Y-shaped catheter of FIG. 27A is delivering the stent in the bifurcated area, tracking over the wire that joins the two tips together.
Figure 29B:
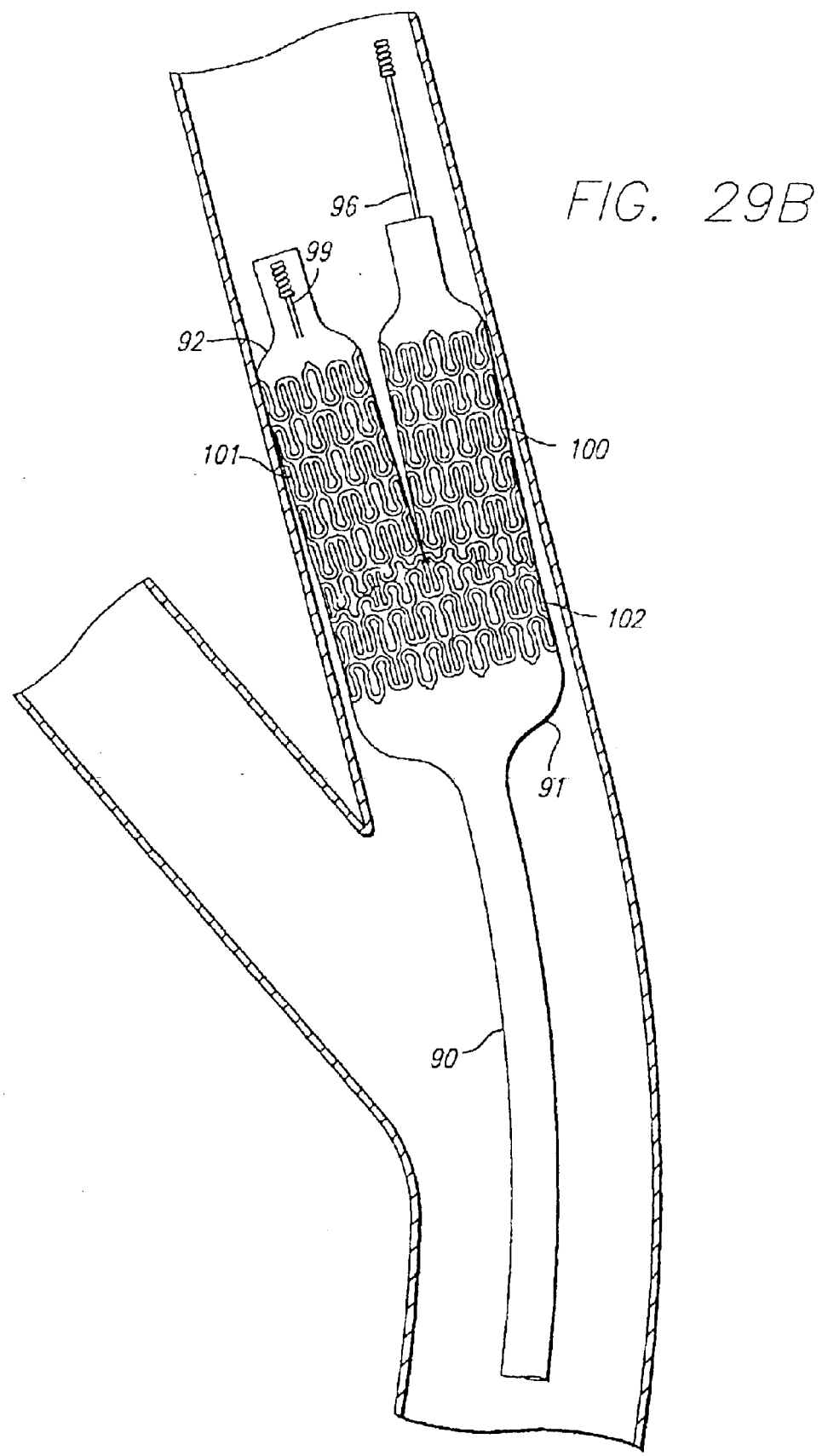
FIG. 29B is an elevational view, partially in section, of a bifurcation in which the delivered Y-shaped balloon components have been released and spread apart by withdrawal of the tracking wire from the other balloon tip lumen.
Figure 29C:
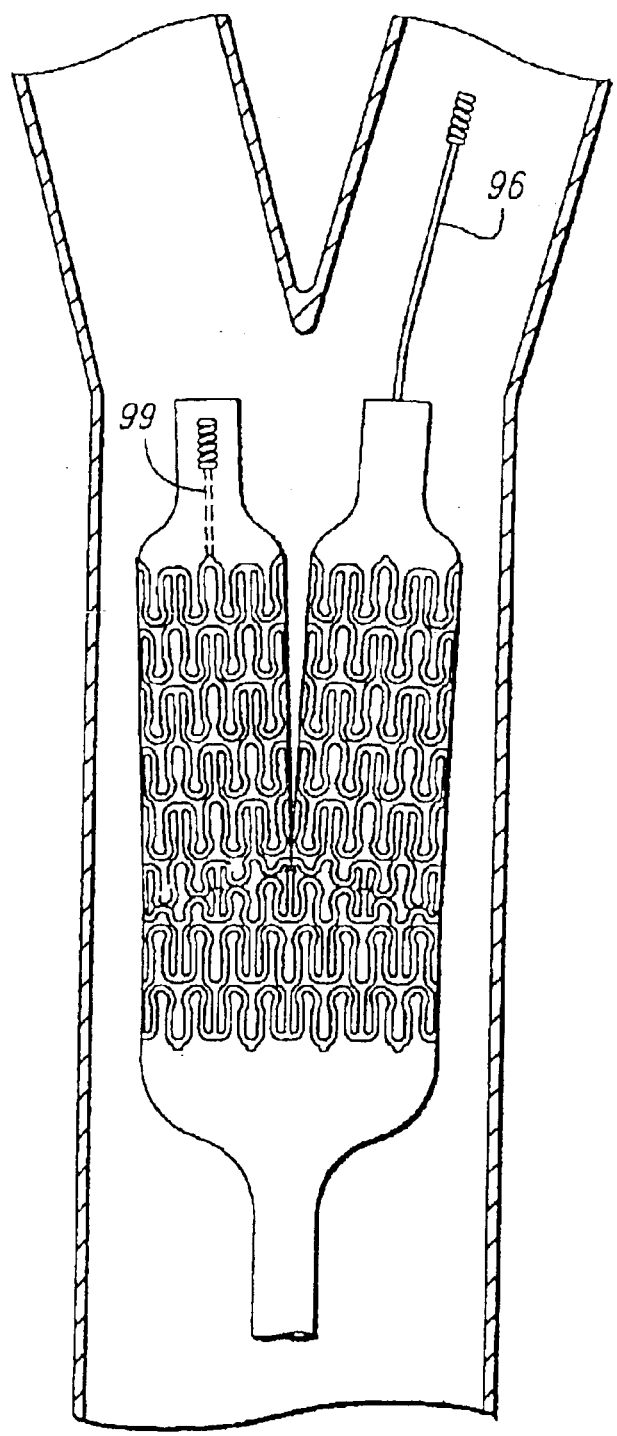
FIG. 29C is an elevational view, partially in section, of the Y-shaped delivery catheter of FIG. 27A in which the Y-shaped balloon has been withdrawn proximal to the bifurcation, leaving the first wire in the right branch.

Several alternative embodiments of main-vessel catheter 70 shown in FIG. 20A, are depicted in FIGS. 20E, 21 and 22. The catheter device shown in FIG. 20E is similar to that shown in FIG. 20A, with the exception that ramp 57 is employed just distal of the distal end of the guide wire lumen 74 so that as guide wire 77 exits the lumen, it will move outwardly along ramp 57 so that it more easily advances into the side-branch vessel. Likewise, as shown in FIGS. 21 and 22, which are similar to the catheter described and depicted in FIGS. 20B and 20C, it is intended that guide wire 77 move outwardly so that it can more easily be advanced into the side-branch vessel. In that regard, the distal end of guide wire lumen 74 is biased outwardly as shown in FIG. 22, so that as the guide wire 77 is pulled back from lumen 75, the distal end of guide wire lumen 74 will spring outwardly thereby assisting guide wire 77 in moving radially outwardly to be positioned in the side-branch vessel.

In order to implant a square main-vessel stent 78A in a main vessel, where the disease is at or just proximal to the side-branch vessel, catheter 70 as depicted in FIGS. 21 and 22 is well suited. For example, catheter 70 is advanced over wire 77 until the catheter is positioned just proximal of the side-branch vessel. Guide wire 73, which up to this point has been contained within catheter 70, is advanced into the main vessel so that it is distal of the side-branch vessel. Guide wire 77 is then withdrawn proximally so that its distal end 77A is withdrawn from lumen 75, whereupon wire 77 and the distal end of guide wire lumen 74 spring outwardly thereby assisting the positioning of guide wire 77 into the side-branch vessel. The wire is then advanced into the side-branch vessel and catheter 77 is advanced so that wire 77 rests on the proximal ostium of the side-branch vessel, wherein square stent 78A can then be expanded to cover the diseased portion, but not span or cover (jail) the opening to the side-branch vessel.

If the diseased portion of a main vessel is directly adjacent the opening to the side-branch vessel, as depicted in FIG. 20F then the catheter system as depicted in FIG. 20A can be incorporated only it would implant distal angled stent 78B. As shown in FIG. 20F, stent 78B has an angle at its distal end which coincides with the opening to the side-branch vessel so that the diseased portion of the main vessel is covered by the distal end of the stent, with the angle of the stent angled proximally so that the side-branch vessel is not covered or jailed. Various alternatives of square stent 78A and distal angled stent 78B are used for treating various conditions as depicted in FIGS. 23A through 26B.

In another alternative embodiment as depicted in FIGS. 27–33, a dual balloon Y-shaped catheter assembly is provided to stent a bifurcation. In this embodiment, a Y-shaped stent is implanted to cover the bifurcation. Catheter 90 includes first and second expandable members 91,92 that are configured to reside side by side (Y-shaped) for low profile delivery and to spring apart for implanting the stents. Locking ring 93 may be used to assist in holding the expandable members together until just prior to use, at which time it is removed. A guide wire lumen 95 extends at least through a portion of the catheter and slidably receives guide wire 96. Guide wire lumen 98 extends at least through a portion of the catheter and slidably receives guide wire 99. Guide wire lumen 98 includes distal section 98A and 98B. A Y-shaped stent 100 is mounted on the first and second expandable members 91, 92.

Figure 30:
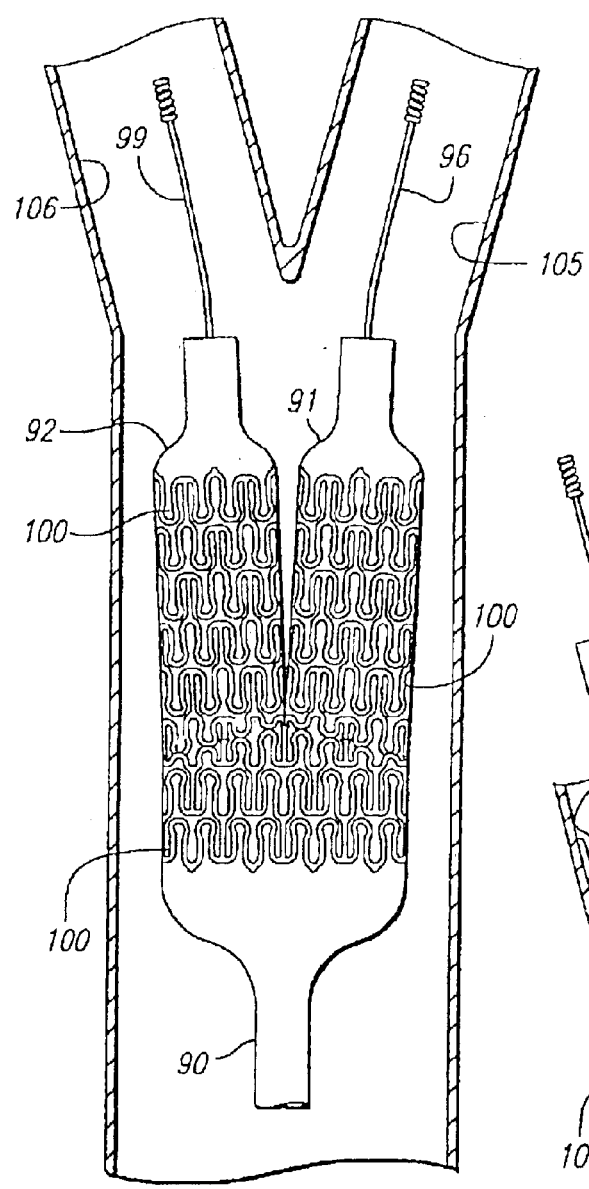
FIG. 30 is an elevational view, partially in section, of the Y-shaped delivery catheter of FIG. 27A in which the second guide wire is advanced into the left branch.
Figure 31:
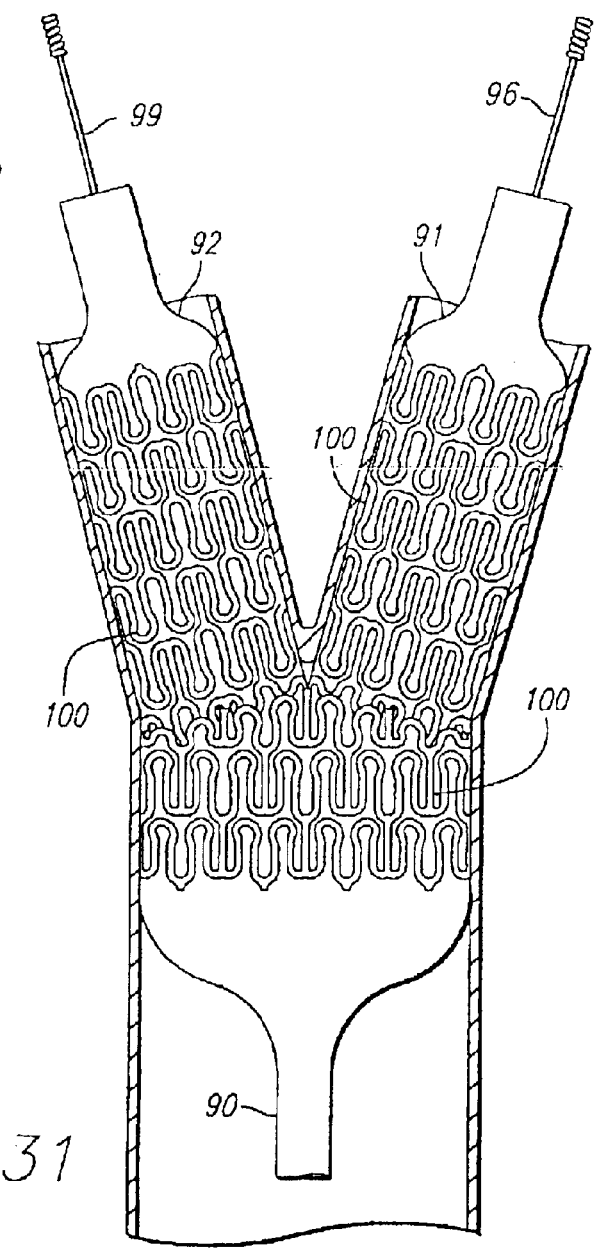
FIG. 31 is an elevational view depicting the Y-shaped catheter of FIG. 27A in which the Y-shaped stent is implanted in the side branch and main vessels of the bifurcation.
Figure 32:
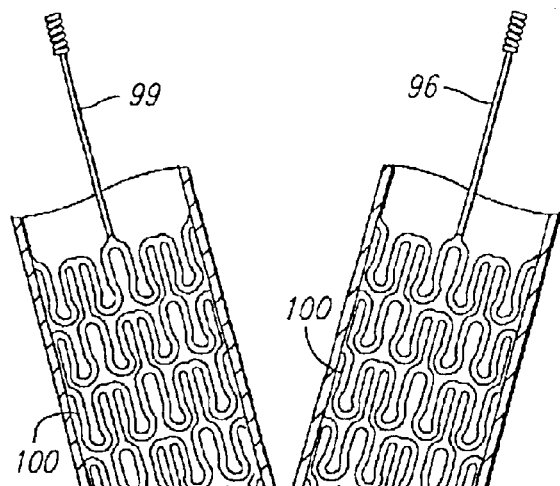
FIG. 32 is an elevational view, partially in section, depicting the Y-shaped catheter assembly of FIG. 27A in which the Y-shaped stent has been implanted and the balloon portions of the catheter have been deflated.
Figure 33:
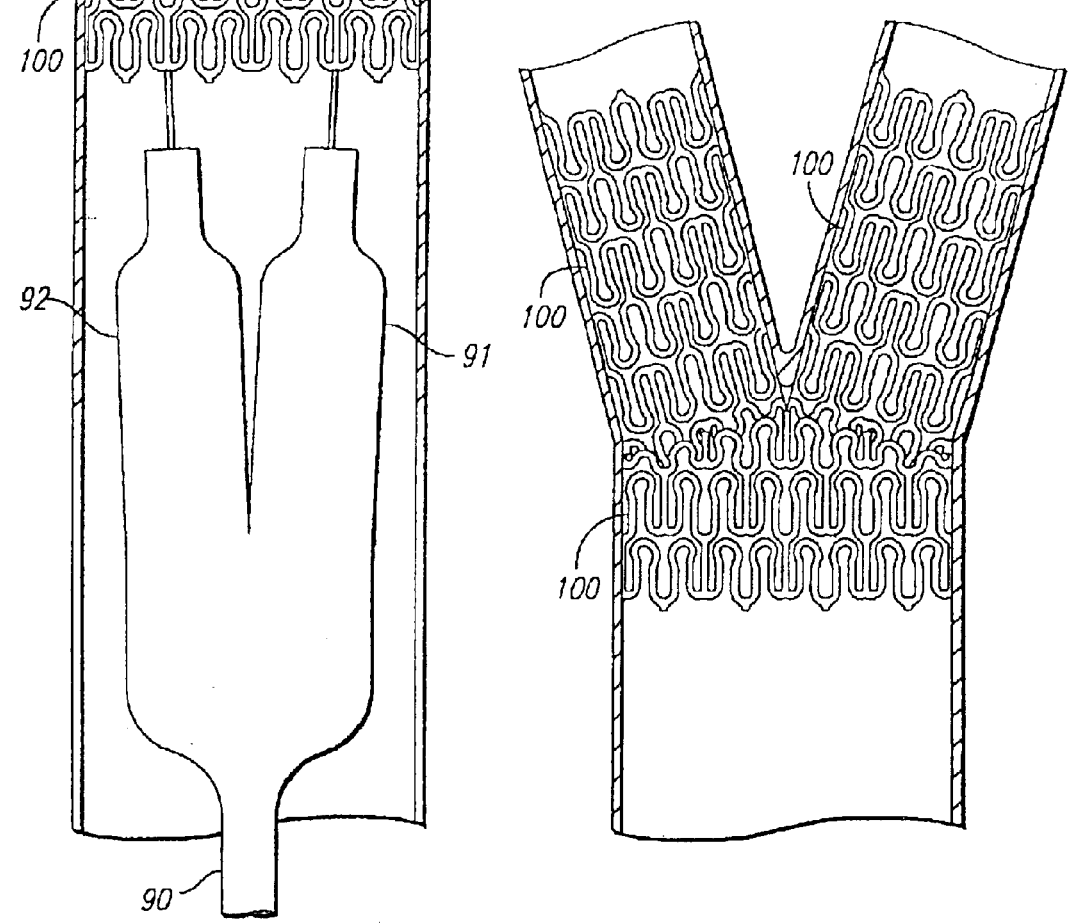
FIG. 33 is an elevational view depicting a bifurcated vessel in which the catheter of FIG. 27A has been withdrawn after implanting the Y-shaped stent.

In the preferred method of stenting the bifurcated vessels, as shown in FIGS. 29 to 33, guide wire 99, previously positioned distal to the bifurcation in one limb (perhaps the most vulnerable to problems for wire recrossing), is back loaded into lumens 98A and 98B and catheter 90 is advanced over wire 99 so that the catheter is advanced distally beyond the bifurcation. Guide wire 96 which has been contained in lumen 95 to this point, is carried in lumen 95 as the catheter is advanced along guide wire 99. Wire 99 is then withdrawn until its distal end pulls out of the distal section 98A. As guide wire 99 is pulled back (proximally), the first and second expandable members 91,92, which are normally biased apart, are released and now spring apart. The wire whose lumen is most distant (lateral) to the bifurcation (in this case wire 96) is then advanced into the distal vessel and the other wire (in this case 99) withdrawn as seen in FIG. 29B. The catheter is then withdrawn proximally so that the expandable members 91,92 are now proximal to the bifurcation as depicted in FIG. 29C and the other guide wire (in this case wire 99) advanced into the other limb of the bifurcation as shown in FIG. 30. Catheter 90 is then advanced distally over both guide wires 96 and 99, as shown in FIG. 31, until stent 100 is positioned in the bifurcation of the intersection of the vessels 105,106. Due to the appropriate wire selection, rotation of no more than 90° will be required. Stent 100 is implanted by inflating expandable members 91,92 in a known manner. The expandable members are then deflated, and the catheter is withdrawn from the patient. The novel arrangement of guide wires 96 and 99 and their respective lumens permit single unit transport of a Y stent to the distal target site without wire wrapping problems and it allows for minimal requirements of rotation of the device (less than 90°) for optimal deployment (allowing minimal twist deformity). The guide wires may be left in place for further intervention such as finishing the stents with simultaneous high pressure balloon inflation.

In an alternative embodiment of the invention, a pair of stents having varying stent cell density are implanted in a bifurcated vessel, as depicted in FIGS. 34–36C.

Figure 35:
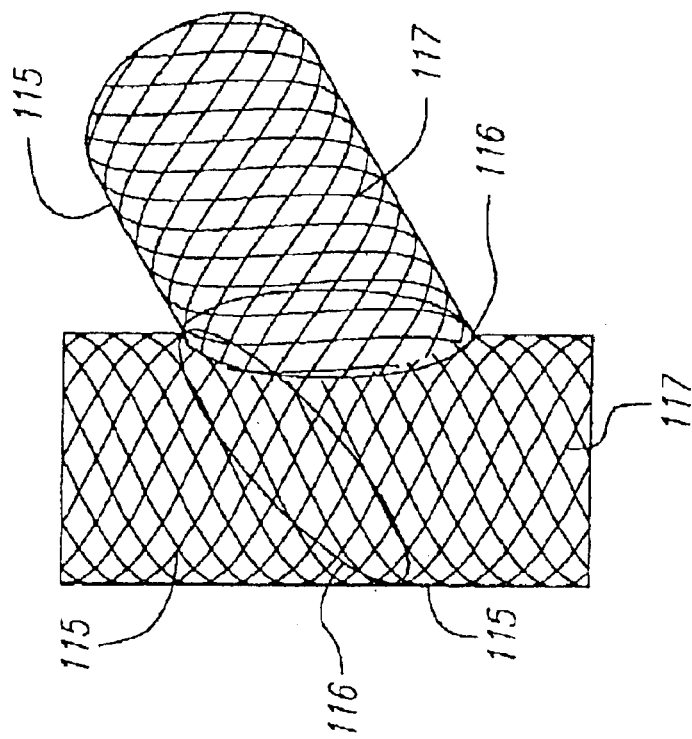
FIG. 35 is an elevational view depicting the stent of FIG. 34 combined to form a stent having a heavy stent cell density in all portions.
Figure 34:
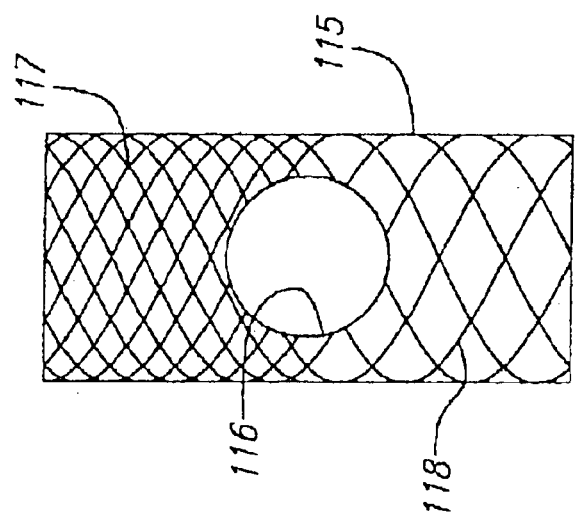
FIG. 34 is an elevational view depicting a modified stent having an aperture in its sidewall and in which half of the stent has a heavy stent cell density while the other half of the stent has a light stent cell density.

As shown in FIG. 34, apertured stent 115 is provided in which aperture 116 is positioned on its outer surface. Stent 115 includes heavy stent cell density 117 and light stent cell density 118 along its outer surface. As can be seen in FIG. 35, two stents 115 have been combined so that the light density of one overlaps the light density of the other causing the combined stents to create relatively uniform heavy cell density and thus providing relatively uniform heavy cell density over the entire bifurcated vessel wall.

Figure 36A:
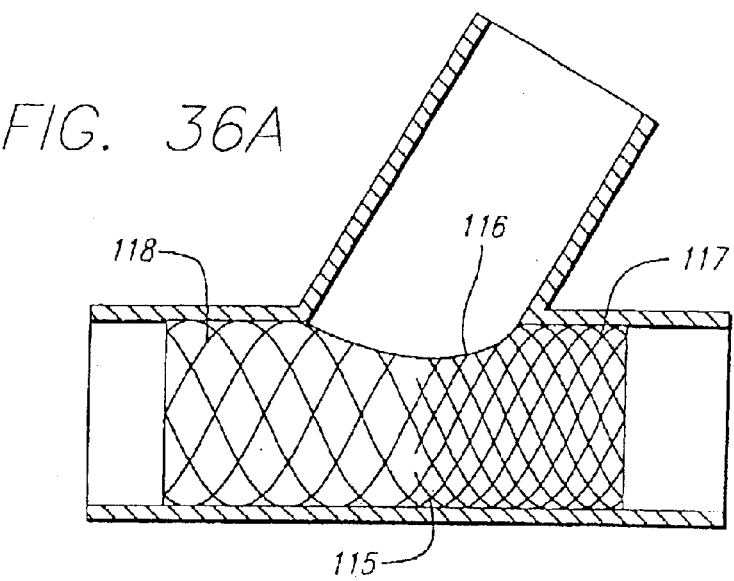
FIG. 36A is an elevational view depicting a bifurcation, in which the stent of FIG. 35 has been implanted so that the aperture corresponds to the side-branch vessel and the stent is implanted in the main vessel.
Figure 36B:
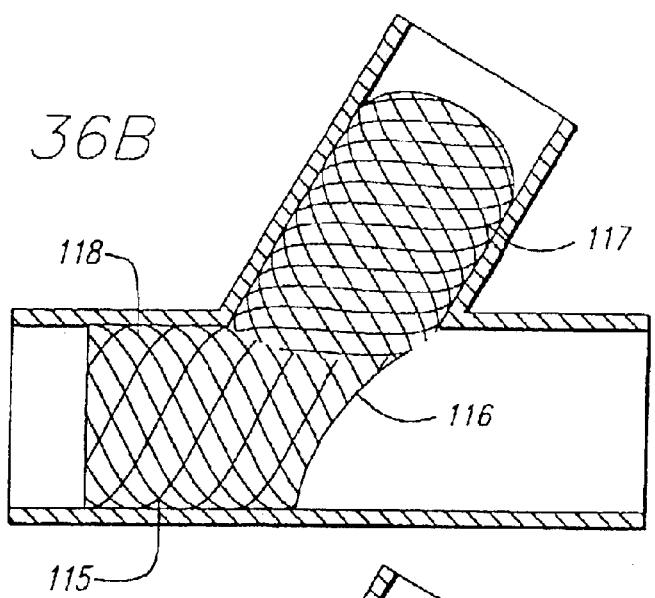
FIG. 36B is an elevational view depicting a bifurcating vessel in which the stent of FIG. 34 has been implanted so that the heavy stent cell density is in the side-branch vessel and the light cell density is in the main vessel. The aperture corresponds to the continuing lumen of the main vessel.
Figure 36C:
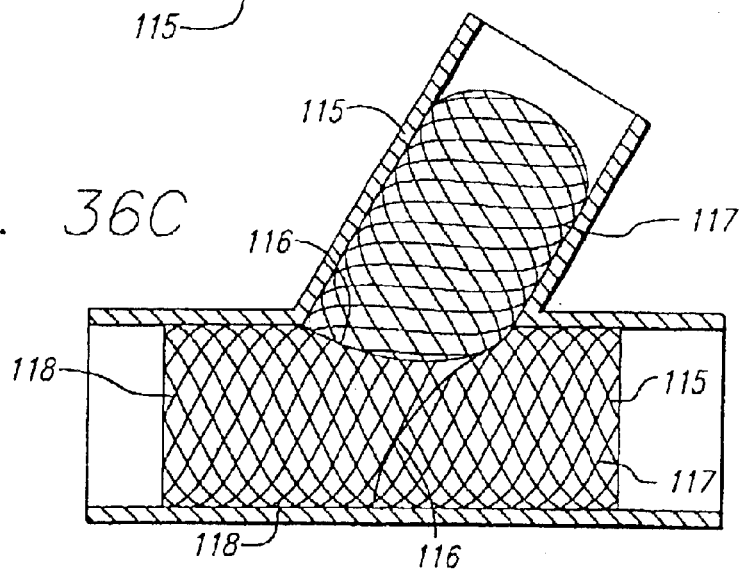
FIG. 36C is an elevational view depicting a bifurcated vessel in which two stents of FIG. 34 have been implanted in the side-branch vessel and the main vessel respectively so that the light stent cell density of each overlaps with the light cell density of the other thereby creating cell density proximal to the bifurcation similar to the heavy cell density present in each limb distal to the bifurcation.

As shown in FIGS. 36A to 36C, two stents 115 are implanted to stent the bifurcation. For sake of clarity, as shown in FIG. 36A, apertured stent 115 shown implanted in the main vessel such that aperture 116 spans and provides an opening to the side-branch vessel while heavy stent cell density 117 provides full coverage of the distal main vessel by stent 115. As depicted in FIG. 36B, apertured stent 115 is partially implanted in the side-branch vessel and partially implanted in the main vessel, in this case with aperture 116 facing the continuing lumen of the main vessel. More specifically, heavy stent cell density portion 117 is implanted in the side-branch vessel, while light stent cell density 118 is implanted in the main vessel, with aperture 116 providing an opening for blood flow through the main vessel. It is intended that stent 115 be implanted first as seen in FIG. 36A and that a second stent 115 subsequently be implanted as shown in 36B or, by physician preference, this sequence may be reversed. Thus, in FIG. 36C, both stents 115 have been implanted, and both apertures 116 provide openings so that blood flow is unimpaired through both main vessel and side-branch vessel and no stent struts are left unapposed. The light stent cell density portions 118 of both 115 stents overlap proximal to the bifurcation, thereby insuring that there is full coverage of the bifurcated area by heavy stent cell density. Both stents 115 are implanted with the catheter delivery system described herein which includes a positioning wire to accurately position and implant the stents in the bifurcated vessels.

While the invention herein has been illustrated and described in terms of an apparatus and method for stenting bifurcated vessels, it will be apparent to those skilled in the art that the stents and delivery systems herein can be used in the coronary arteries, veins and other arteries throughout the patient's vascular system. Certain dimensions and materials of manufacture have been described herein, and can be modified without departing from the spirit and scope of the invention.

What is claimed is:

1. A catheter assembly for treating bifurcated vessels having a side-branch vessel and a main vessel, comprising:
   a catheter having a proximal end and a distal end;
   an expandable member proximal to the distal end of the catheter;
   a tracking guide wire lumen extending within at least a portion of the catheter;
   a tracking guide wire having a distal end and a proximal end and sized for slidable movement within the tracking guide wire lumen;
   a positioning guide wire lumen associated with the expandable member wherein at least a portion of the positioning guide wire lumen is external to the catheter;
   a positioning guide wire having a distal end and a proximal end and sized for slidable movement within the positioning guide wire lumen;
   the positioning guide wire lumen having a distal section lumen for removably retaining the distal end of the positioning guide wire during delivery of the catheter through the vasculature to the bifurcated vessel; and
   the distal section lumen of the positioning guide wire lumen having a dead-end so that the distal end of the positioning guide wire does not extend distally through the distal section.

2. The catheter assembly of claim 1, wherein the distal section lumen of the positioning guide wire lumen is positioned adjacent to a distal end of the tracking guide wire lumen.

3. The catheter assembly of claim 1, wherein the distal section lumen of the positioning guide wire lumen is attached to an outer surface of the distal end of the catheter.

4. The catheter assembly of claim 1, wherein the distal section lumen of the positioning guide wire lumen is integrally formed with the distal end of the catheter.

5. The catheter assembly of claim 1, wherein the distal end of the positioning guide wire is biased so that when the positioning guide wire is withdrawn proximally from the distal section, the positioning guide wire distal end springs outwardly away from the catheter.

* * * * *

UNITED STATES PATENT AND TRADEMARK OFFICE
CERTIFICATE OF CORRECTION

PATENT NO. : 6,875,229 B2
DATED : April 5, 2005
INVENTOR(S) : W. Stan Wilson and Kevin M. Mauch It is certified that error appears in the above-identified patent and that said Letters Patent is hereby corrected as shown below:

Column 6,
Line 35, change "flow path, for" to -- flow path for --.

Column 13,
Line 16, change "used for-additional intervention" to -- used for additional intervention. --.
Line 18, change "is only possible after" to -- is only possible after --.

Column 14,
Line 52, after "tightly crimped" add -- onto expandable member 35 for low-profile delivery through the vascular system.
  In the preferred embodiment of the side-branch catheter system 30 (side-branch catheter plus proximal angled stent), distal end 36B of guide wire 36A is advanced into side-branch vessel 5 and distal to the target area, with proximal end 36C remaining outside the patient. The side-branch catheter 31 is then advanced within a guiding catheter (not shown) along tracking guide wire 36A until distal end 32 of the catheter is just proximal (about 1 cm) from entering side-branch vessel 5. Up to this point, guide wire 41A resides in second guide wire lumen 39A so that distal end 41B of the wire preferably is near, but not in, angled portion 39B of guide wire lumen 39A.
  This method of delivery prevents the two guide wires from wrapping around each other, guide wire 41A being protected by the catheter during delivery. The distal end 41B of integrated stent positioning guide wire 41A is then advanced by having the physician push proximal end 41C from outside the body. The distal end 41B of the integrated stent-positioning guide wire travels through guide wire lumen 39A and angled portion 39B and passes close to proximal end 14 of angled stent 10 and expandable member 35 and exits lumen 39B. As guide wire 41A is advanced into, through and out of lumen 39B, the stiffness of the wire causes it to bow outwardly through slit 39D in the distal portion of lumen 39A. Thus, as can be seen for example in FIGS. 9B, 10A, 10B, and 11B-11D, the positioning guide wire bows outwardly and due to its stiffness, provides a bumper against the ostium of the side-branch vessel to assist in positioning and deploying the stents.
  The stent-positioning guide wire 41A is advanced in the main vessel until distal end 41B is distal to side-branch vessel 5. The catheter is then advanced into side-branch vessel 5 until resistance is felt from the stent-positioning guide wire 41A pushing up against the ostium of side-branch vessel 5. As previously described, stent-positioning wire 41A is relatively stiff, as is tracking guide wire 36A, so that they can properly orient side-branch catheter 31 as it is advanced into side-branch vessel 5. Angled portion 39B of second guide wire lumen 39A is angled to assist in rotating the side-branch catheter into proper position into the side-branch vessel. If the stent approaches side-branch vessel 5 in the incorrect position, as depicted in FIGS. 11A-11D, stent-positioning wire 41A would be forced to make a very acute angle.

UNITED STATES PATENT AND TRADEMARK OFFICE
CERTIFICATE OF CORRECTION

PATENT NO. : 6,875,229 B2
DATED : April 5, 2005
INVENTOR(S) : W. Stan Wilson and Kevin M. Mauch It is certified that error appears in the above-identified patent and that said Letters Patent is hereby corrected as shown below:

Column 14 (cont'd),
The wire stiffness, however, prevents this from happening and causes the wire to assume the position of least stress. To relieve this stress buildup, wire 41A creates a torque on angled portion 39B causing guide wire lumen 39A and side-branch catheter 31, with proximal angled stent 10, to rotate into the correct position. Preferably, slit 39D is formed on catheter 31 outer surface near angled portion 39B so that stent-positioning guide wire 41A can bow outwardly out of slit 39D thereby increasing the ability to torque the catheter and the proximal angled stent. --.

Column 19,
Line 65, change "stent 60,already is" to -- stent 60 already is --.

Signed and Sealed this

Thirteenth Day of December, 2005

JON W. DUDAS
*Director of the United States Patent and Trademark Office*